(12) United States Patent
Jovanovich et al.

(10) Patent No.: US 7,138,254 B2
(45) Date of Patent: *Nov. 21, 2006

(54) METHODS AND APPARATUS FOR PERFORMING SUBMICROLITER REACTIONS WITH NUCLEIC ACIDS OR PROTEINS

(75) Inventors: Stevan Bogdan Jovanovich, Livermore, CA (US); Oscar Salas-Solano, San Francisco, CA (US); Jeng-Thun Li, Pleasanton, CA (US)

(73) Assignee: GE Healthcare (SV) Corp., Sunnyvale, CA (US)

( * ) Notice: Subject to any disclaimer, the term of this patent is extended or adjusted under 35 U.S.C. 154(b) by 471 days.

This patent is subject to a terminal disclaimer.

(21) Appl. No.: 10/361,481

(22) Filed: Feb. 7, 2003

(65) Prior Publication Data

US 2003/0224395 A1    Dec. 4, 2003

Related U.S. Application Data

(63) Continuation-in-part of application No. 10/262,476, filed on Sep. 30, 2002, now Pat. No. 6,927,045, which is a continuation of application No. 09/632,094, filed on Aug. 2, 2000, now Pat. No. 6,489,112, which is a continuation-in-part of application No. 09/577,199, filed on May 23, 2000, now Pat. No. 6,423,536.

(60) Provisional application No. 60/355,660, filed on Feb. 8, 2002, provisional application No. 60/355,648, filed on Feb. 8, 2002, provisional application No. 60/146,732, filed on Aug. 2, 1999.

(51) Int. Cl.
*C12P 19/34* (2006.01)
*C12Q 1/68* (2006.01)
*C07H 21/02* (2006.01)
*C07H 21/04* (2006.01)
*C07H 21/00* (2006.01)

(52) U.S. Cl. .............. 435/91.2; 435/6; 435/91.1; 536/23.1; 536/24.3; 536/24.33; 536/25.3; 536/25.32

(58) Field of Classification Search ............ 435/6, 435/91.1, 91.2, 183, 283.1, 287.1, 287.2; 436/94; 536/23.1, 24.3, 24.33, 25.3
See application file for complete search history.

(56) References Cited

U.S. PATENT DOCUMENTS 5,516,703 A    5/1996    Caldwell et al.

(Continued)

FOREIGN PATENT DOCUMENTS

WO    WO97/10331    3/1997

OTHER PUBLICATIONS

Amankwa et al., "On-Line Peptide Mapping by Capillary Zone Electrophoresis," *Analytical Chemistry* vol. 65: pp. 2693-2697 (1993).

(Continued)

*Primary Examiner*—Frank Lu
(74) *Attorney, Agent, or Firm*—Yonggang Ji

(57) ABSTRACT

Methods for preparing nanoscale reactions using nucleic acids or proteins are presented. Nucleic acids are captured saturably, yet reversibly, on the internal surface of the reaction chamber, typically a capillary. Excess nucleic acid is removed and the reaction is performed directly within the capillary. Proteins are captured specifically and saturably on the modified inner surface of the reaction chamber, typically a capillary. Excess protein is removed and the reaction is performed directly within the capillary. Devices for effecting the methods of the invention and a system designed advantageously to utilize the methods for high throughput reactions involving nucleic acids or proteins are also provided.

35 Claims, 42 Drawing Sheets

U.S. PATENT DOCUMENTS

| | | |
|---|---|---|
| 5,688,648 A | 11/1997 | Mathies et al. |
| 5,707,804 A | 1/1998 | Mathies et al. |
| 5,719,060 A | 2/1998 | Hutchens et al. |
| 5,720,923 A | 2/1998 | Haff et al. |
| 5,728,528 A | 3/1998 | Mathies et al. |
| 5,785,926 A | 7/1998 | Seubert et al. |
| 5,846,727 A | 12/1998 | Soper et al. |
| 5,853,992 A | 12/1998 | Glazer et al. |
| 5,869,225 A | 2/1999 | Yamaya |
| 5,897,842 A | 4/1999 | Dunn |
| 5,948,227 A | 9/1999 | Dubrow |
| 5,958,694 A | 9/1999 | Nikiforov |
| 5,965,410 A | 10/1999 | Chow et al. |
| 5,976,336 A | 11/1999 | Dubrow et al. |
| 6,028,190 A | 2/2000 | Mathies et al. |
| 6,042,710 A | 3/2000 | Dubrow |
| 6,068,752 A | 5/2000 | Dubrow et al. |
| 6,071,748 A | 6/2000 | Modlin et al. |
| 6,097,025 A | 8/2000 | Modlin et al. |
| 6,107,044 A | 8/2000 | Nikiforov |
| 6,124,137 A | 9/2000 | Hutchens et al. |
| 6,153,073 A | 11/2000 | Dubrow et al. |
| 6,174,675 B1 | 1/2001 | Chow et al. |
| 6,187,267 B1 | 2/2001 | Taylor et al. |
| 6,225,047 B1 | 5/2001 | Hutchens et al. |
| 6,235,175 B1 | 5/2001 | Dubrow et al. |
| 6,235,471 B1 | 5/2001 | Knapp et al. |
| 6,267,858 B1 | 7/2001 | Parce et al. |
| 6,274,337 B1 | 8/2001 | Parce et al. |
| 6,287,774 B1 | 9/2001 | Nikiforov |
| 6,290,995 B1 | 9/2001 | Xinxian |
| 6,297,018 B1 | 10/2001 | French et al. |
| 6,303,343 B1 | 10/2001 | Kopf-Sill |
| 6,306,590 B1 | 10/2001 | Mehta et al. |
| 6,306,659 B1 | 10/2001 | Parce et al. |
| 6,310,687 B1 | 10/2001 | Stumbo et al. |
| 6,316,201 B1 | 11/2001 | Nikiforov |
| 6,326,605 B1 | 12/2001 | Modlin et al. |
| 6,489,112 B1 | 12/2002 | Hadd et al. |
| 6,927,045 B1 * | 8/2005 | Hadd et al. ............... 435/91.2 |

OTHER PUBLICATIONS

Carlsson et al., "Protein Thiolation and Reversible Protein-Protein Conjugation N-Succinimidyl 3-(2-pyridyldithio) Propionate, a New Heterobifunctional Reagent," *Biochem J* vol. 173 No. 3: p. 723-737 (Sep. 1978).

Chen et al., "Recovery of DNA Segments from Agarose Gels," *Analytical Biochemistry* vol. 101 No. 2: pp. 339-341 (1980).

Clark et al., "Sniper: A Fully Automated, Fluorescence Platform Incorporating Rolling Circle Amplification for Scalable, High-Throughput SNP Scoring," *Life Science News* vol. 6 (2000).

Liu et al., "Automated Parallel DNA Sequencing on Multiple Channel Microchips," *Proc. Natl. Acad. Sci. USA* vol. 97 No. 10 (May 9, 2000).

Shi, M., "Enabling Large-Scale Pharmacogenetic Studies by High-Throughput Mutation Detection and Genotyping Technologies," *Clinical Chemistry* vol. 47 No. 2: pp. 164-172 (2001).

Vogelstein et al., "Preparative and Analytical Purification of DNA from Agarose," *Proc. Natl. Acad. Sci. USA* vol. 76 No. 2: pp. 615-619 (1979).

\* cited by examiner

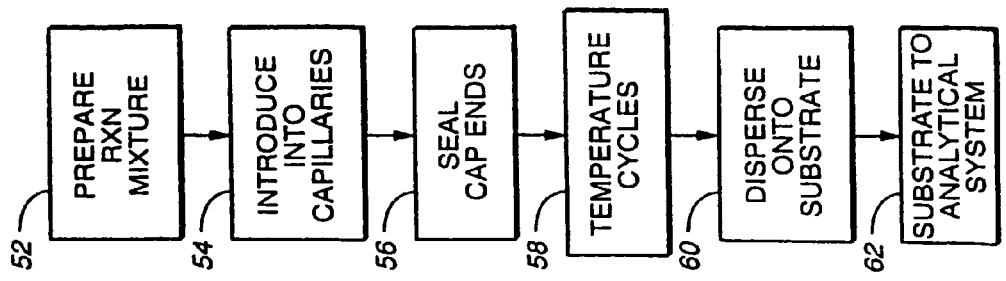
FIG._2
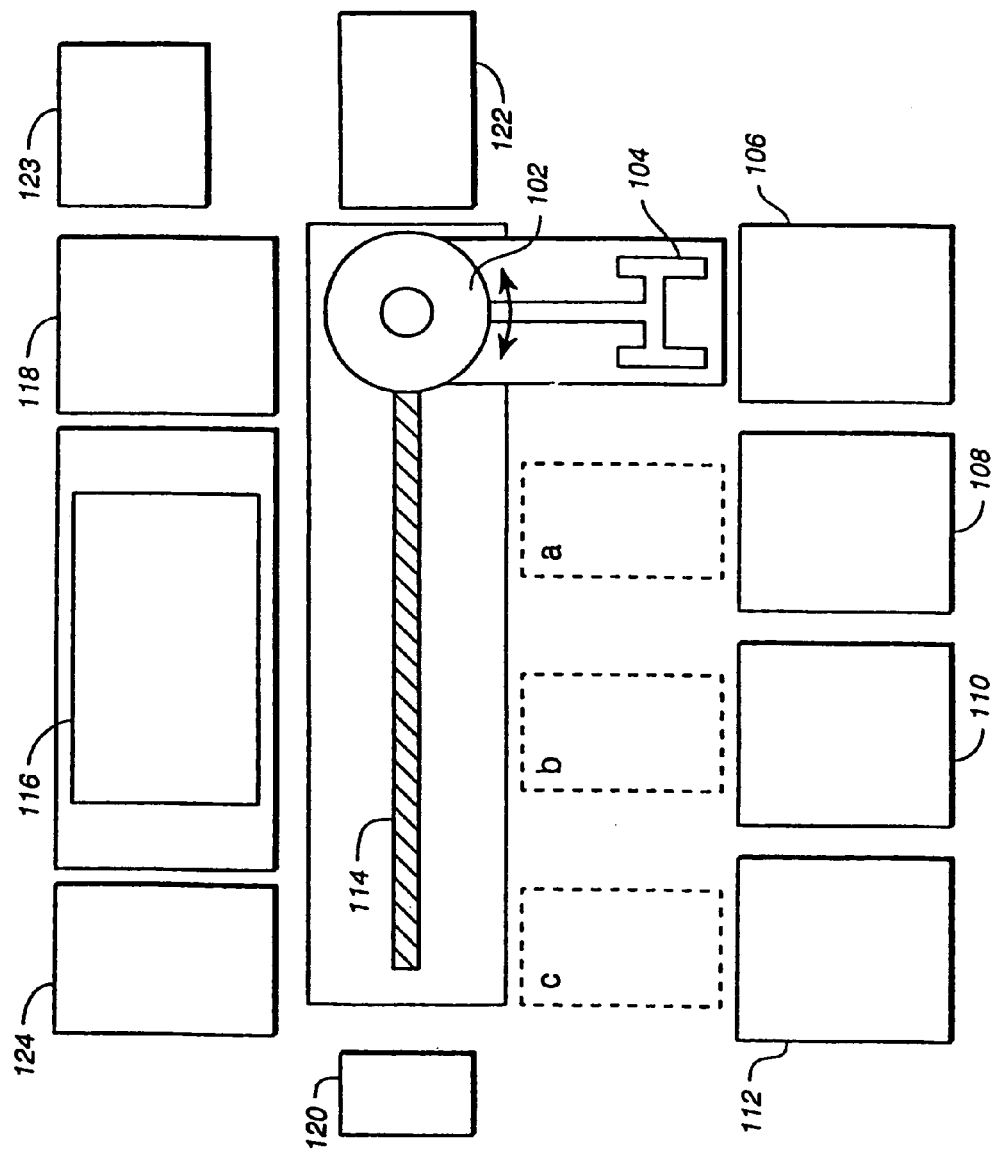
FIG._1

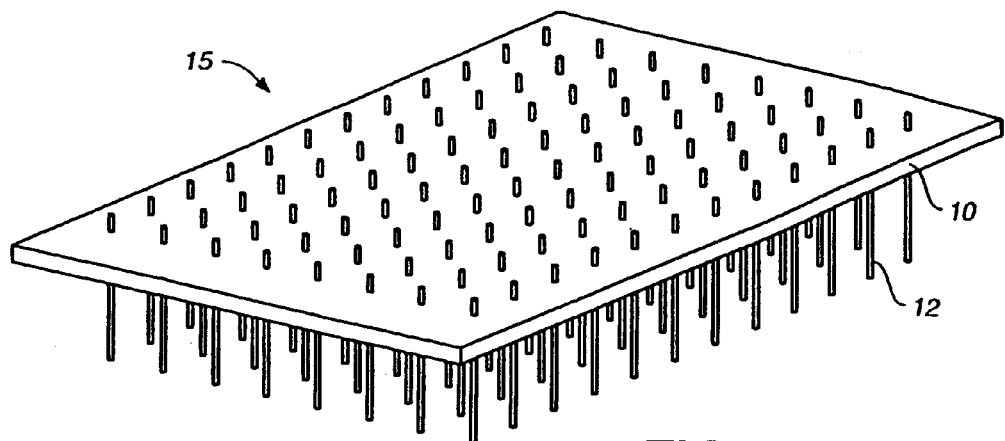
FIG._3A
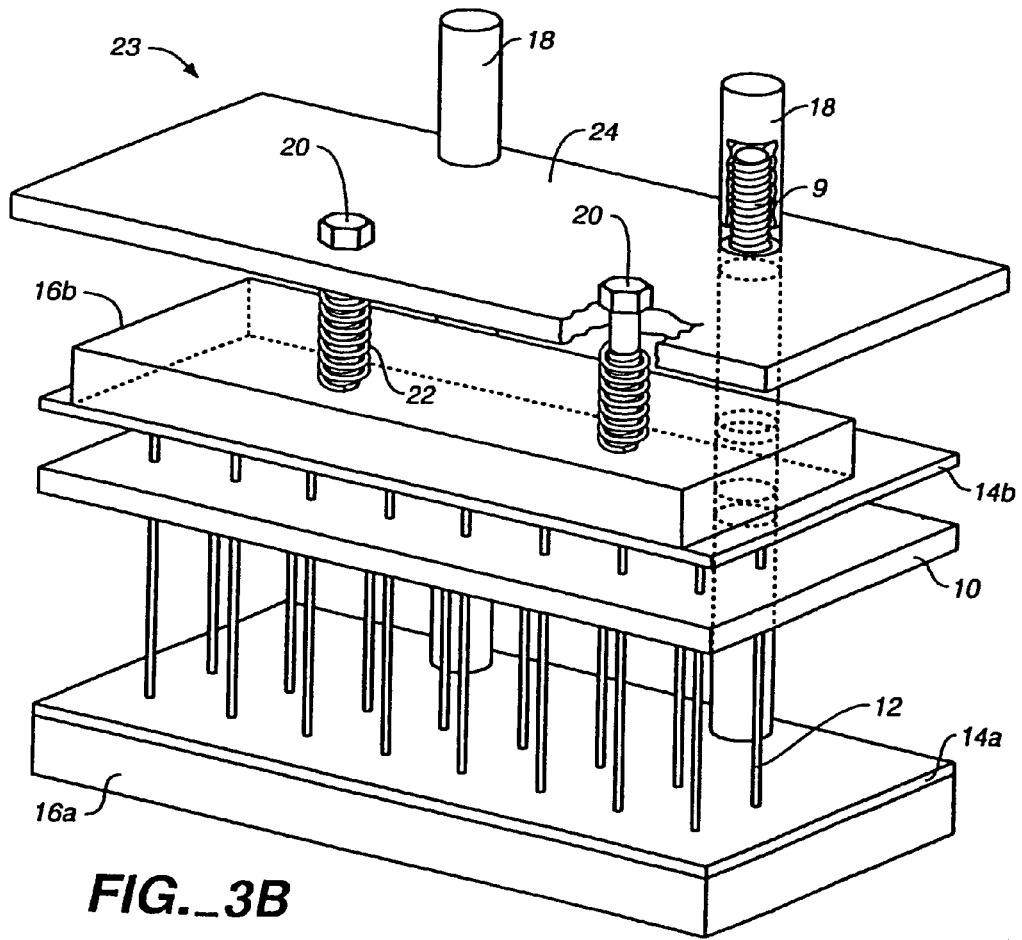
FIG._3B

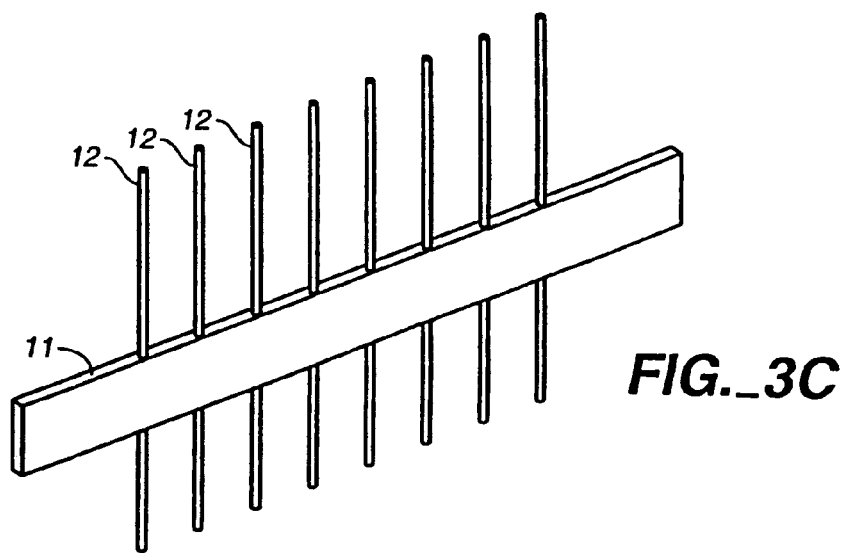
FIG._3C
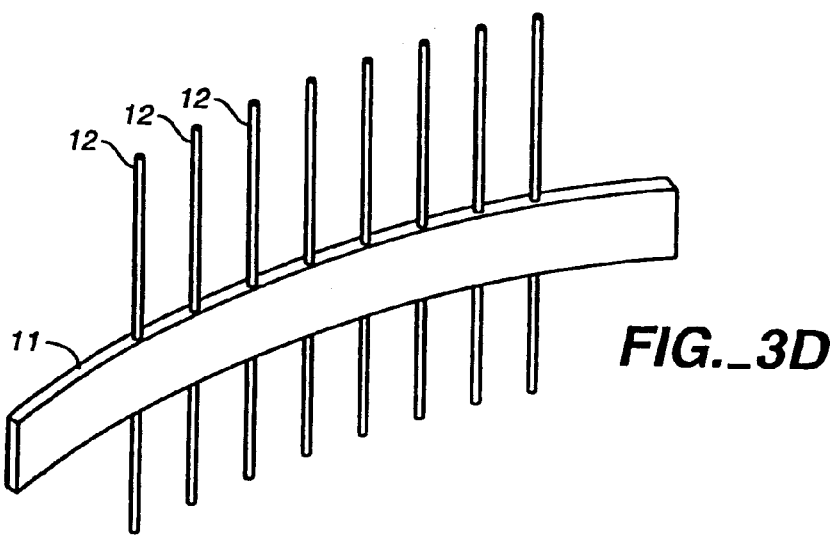
FIG._3D
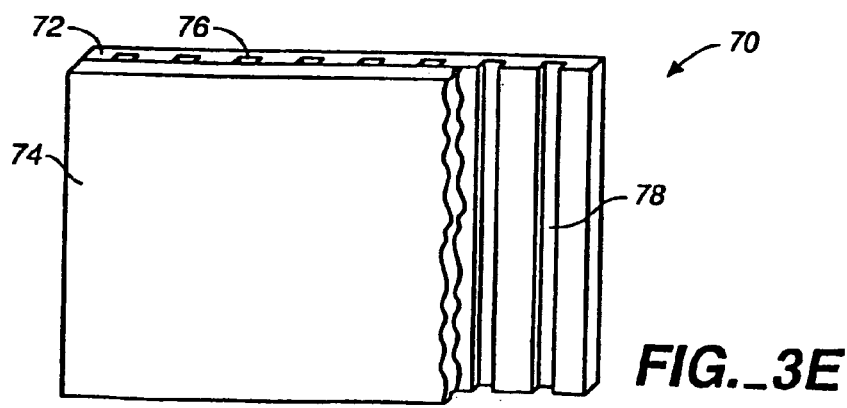
FIG._3E

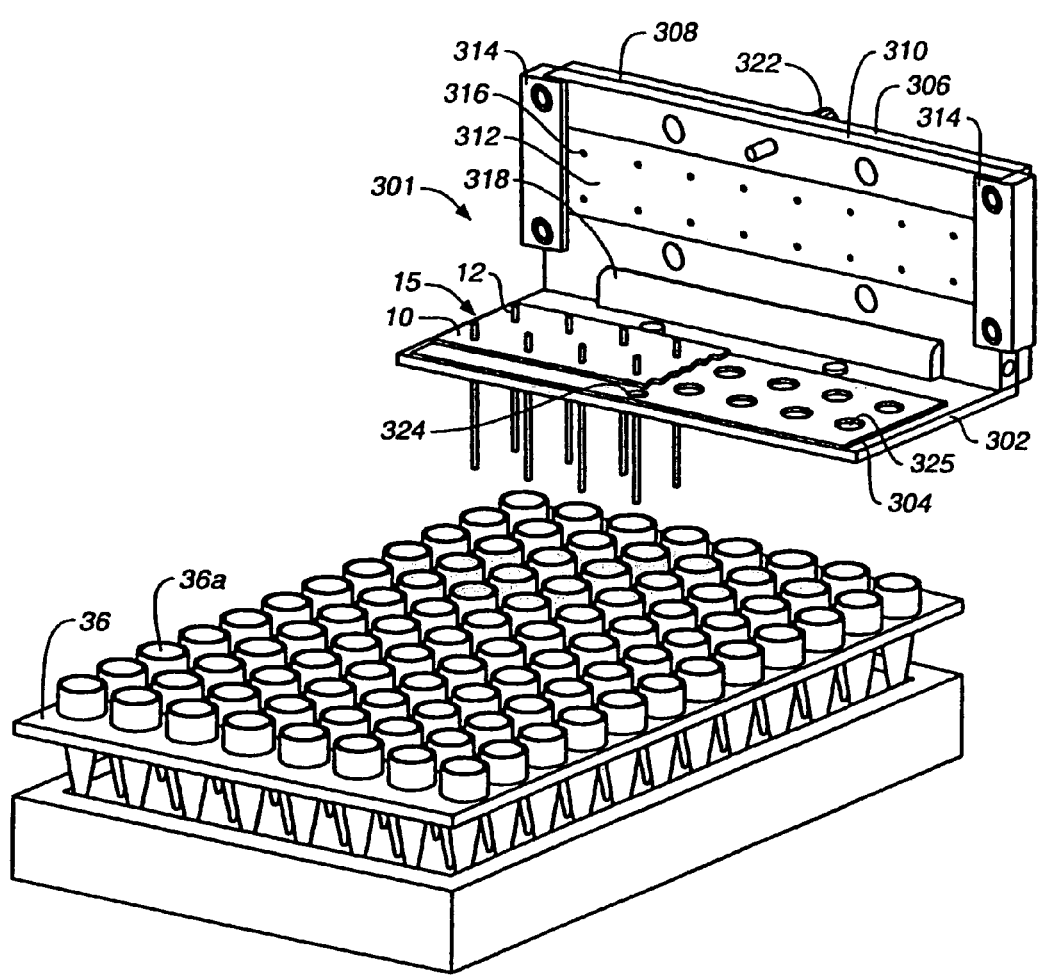
FIG._4A

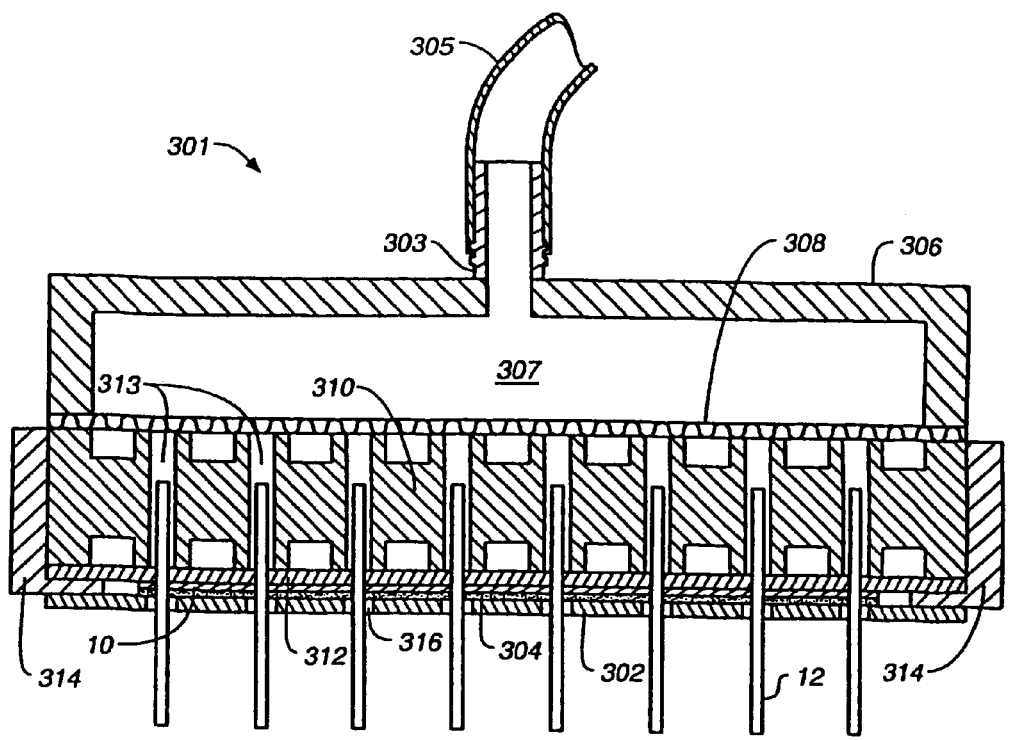
FIG._4B
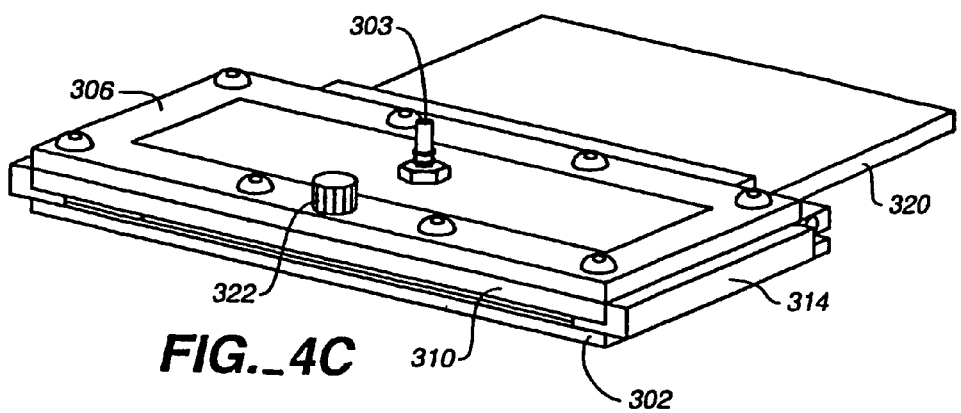
FIG._4C

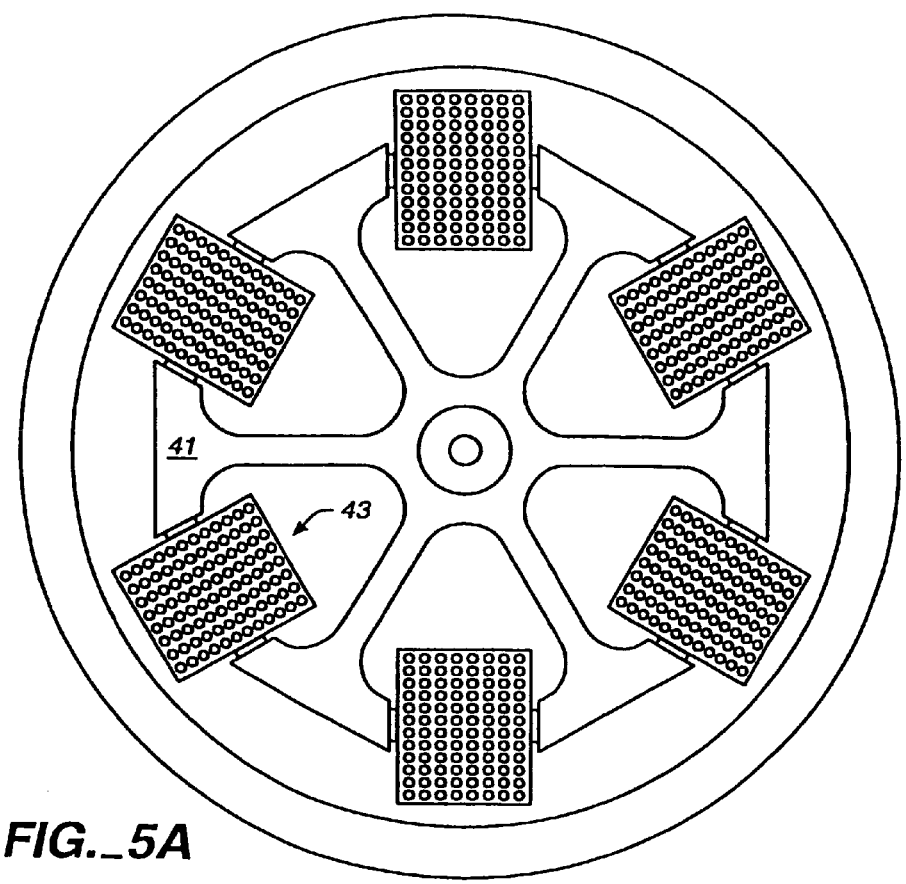
FIG._5A
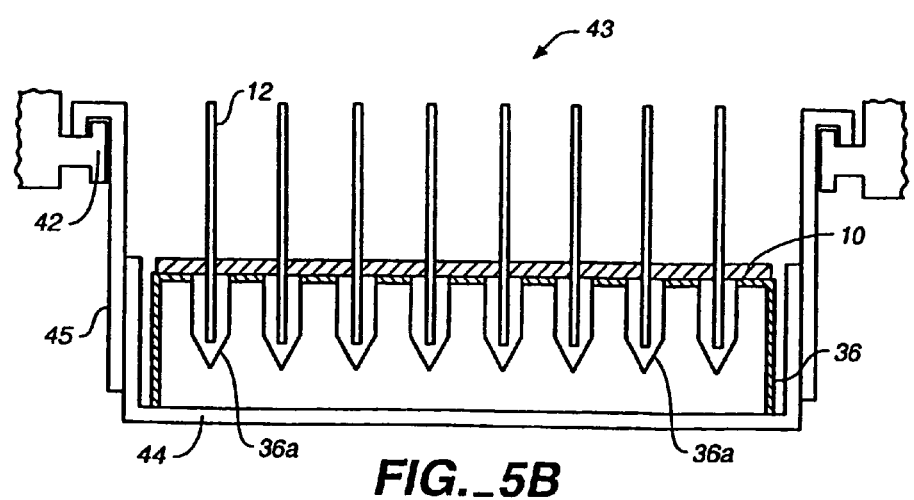
FIG._5B

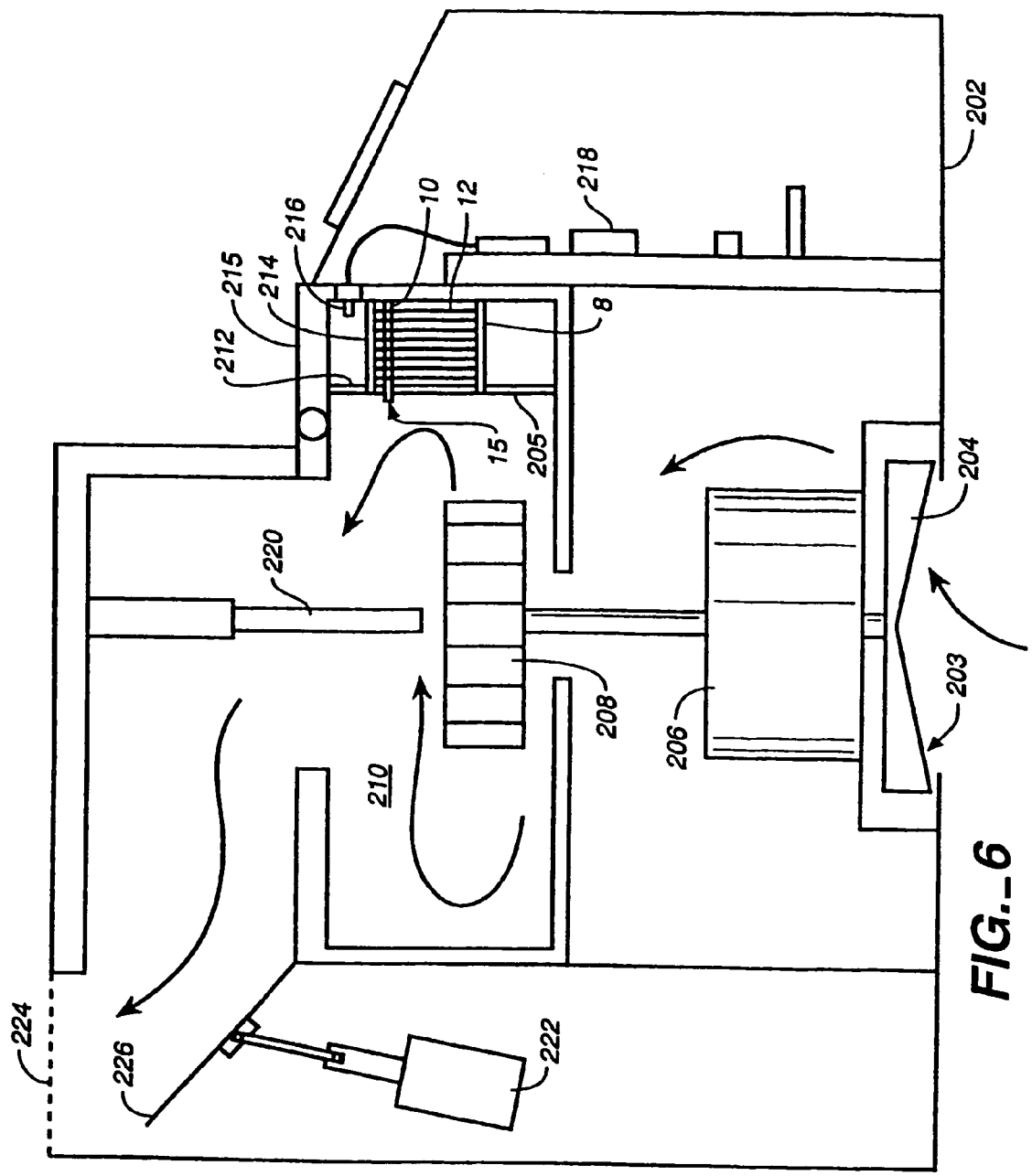
FIG._6

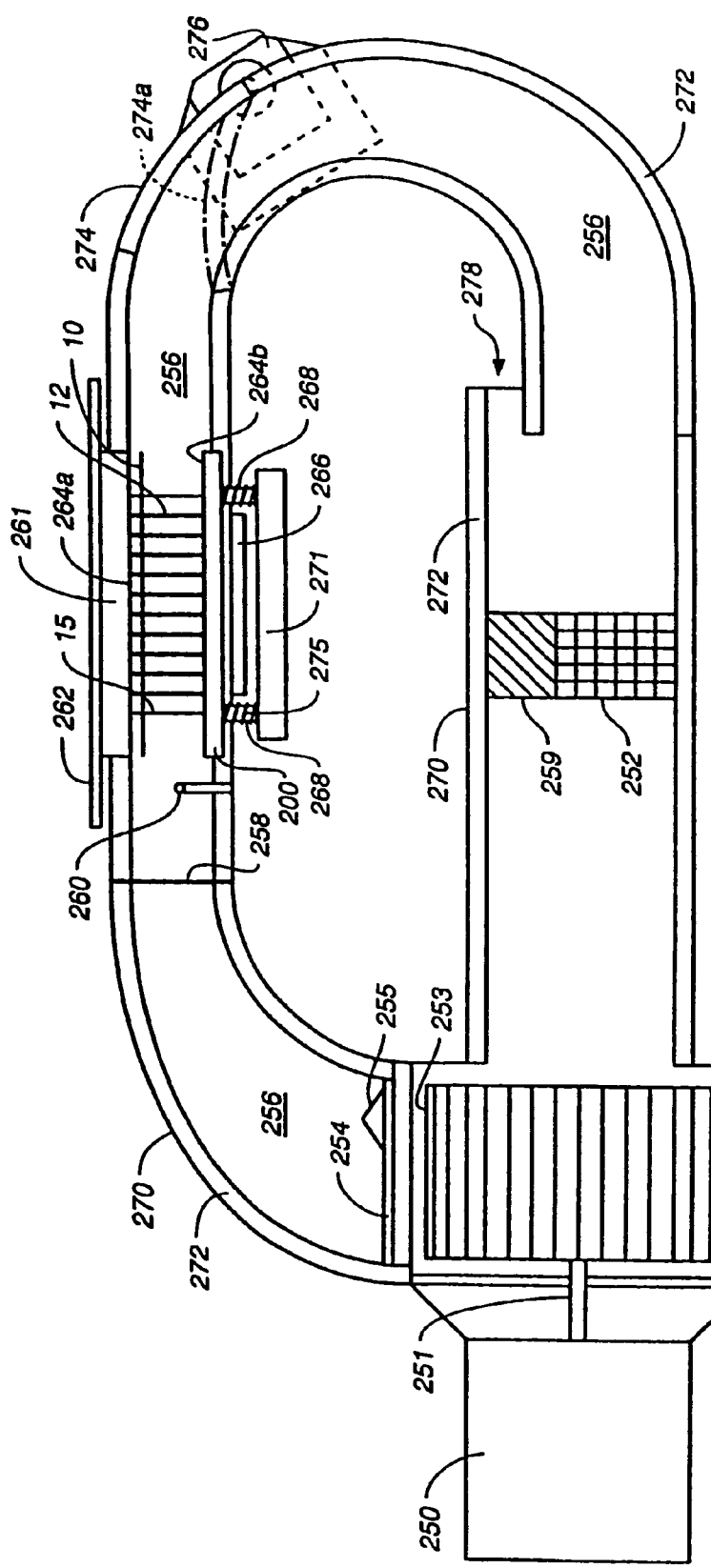

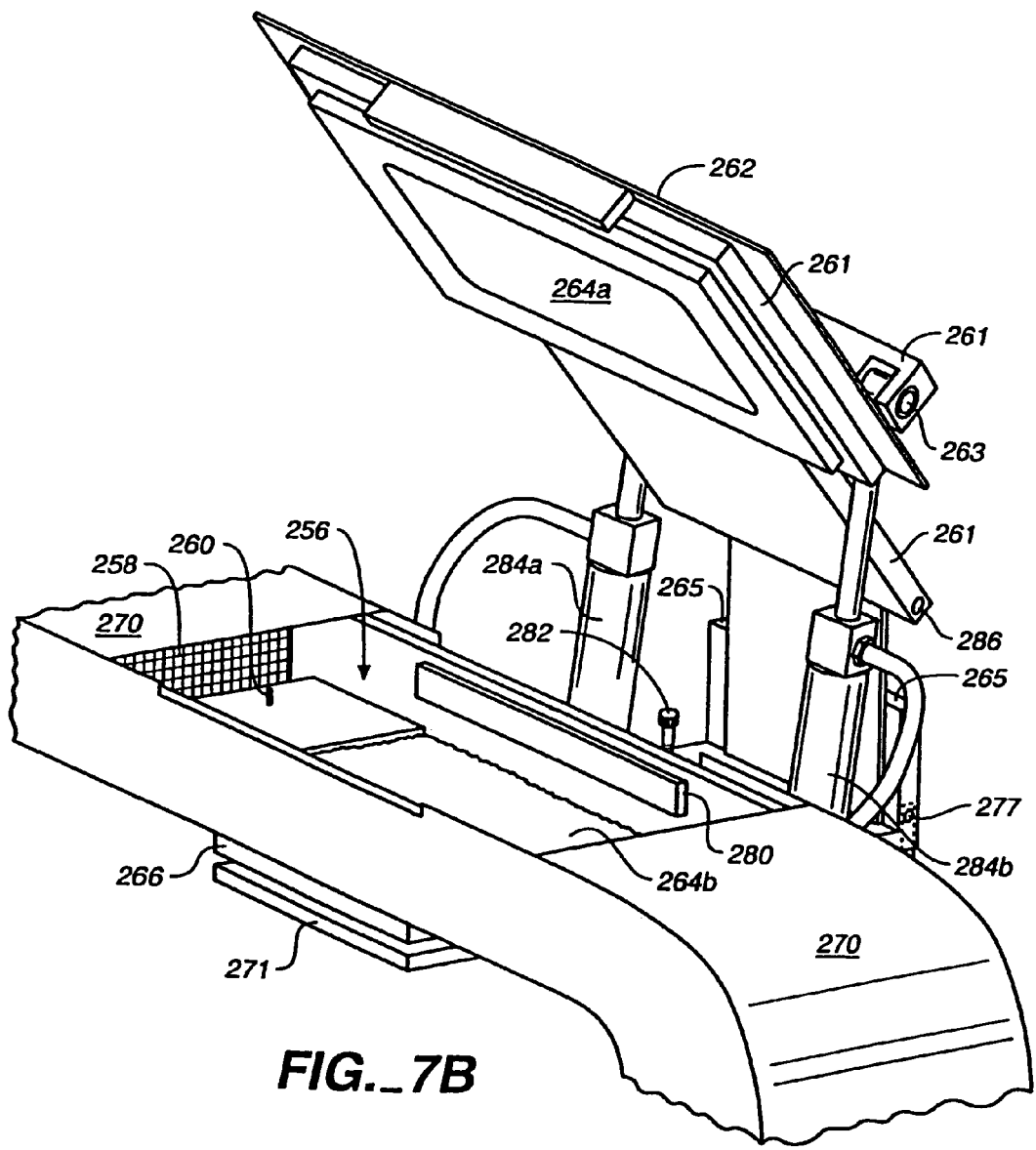
FIG._7B

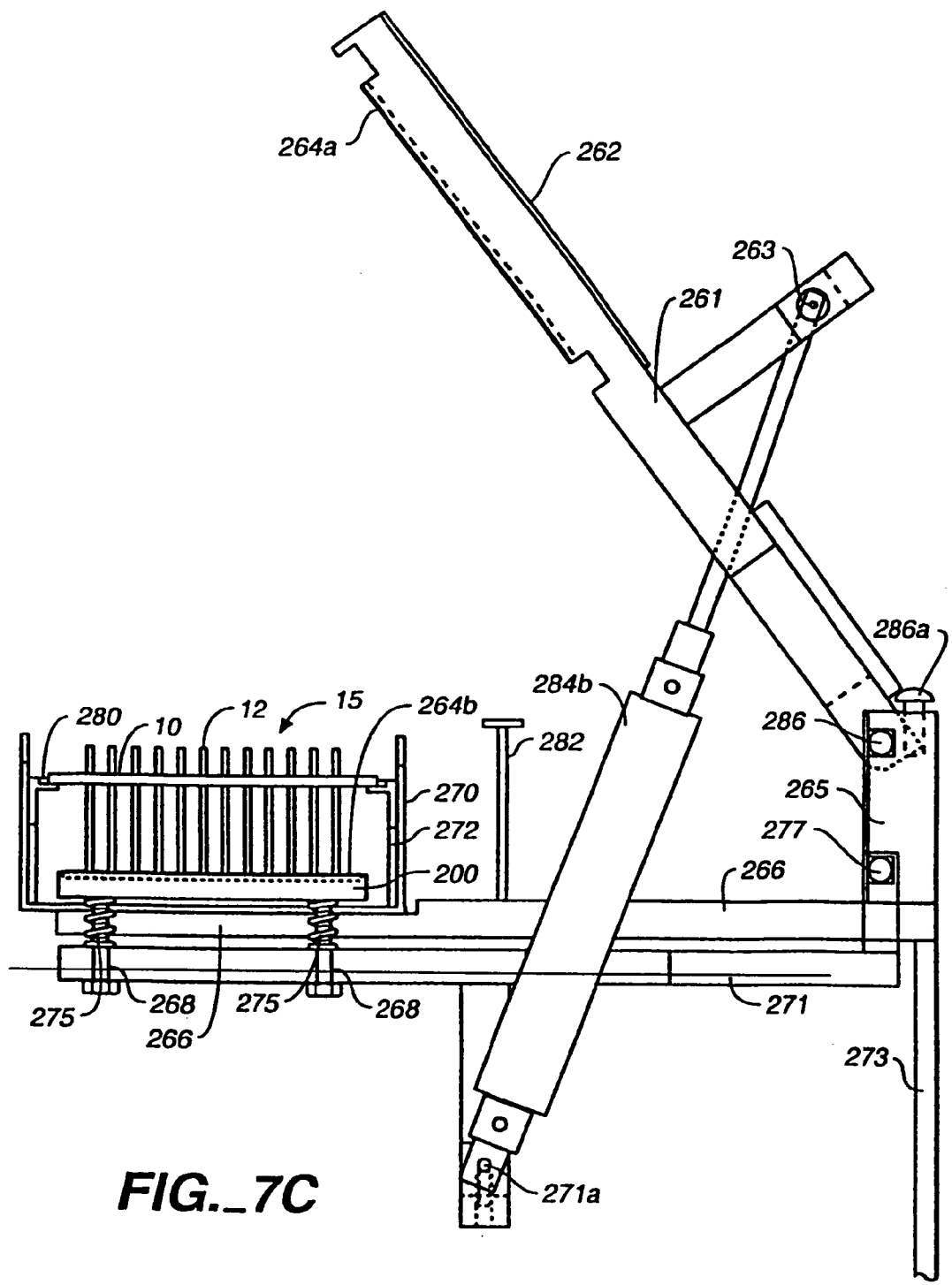
FIG._7C

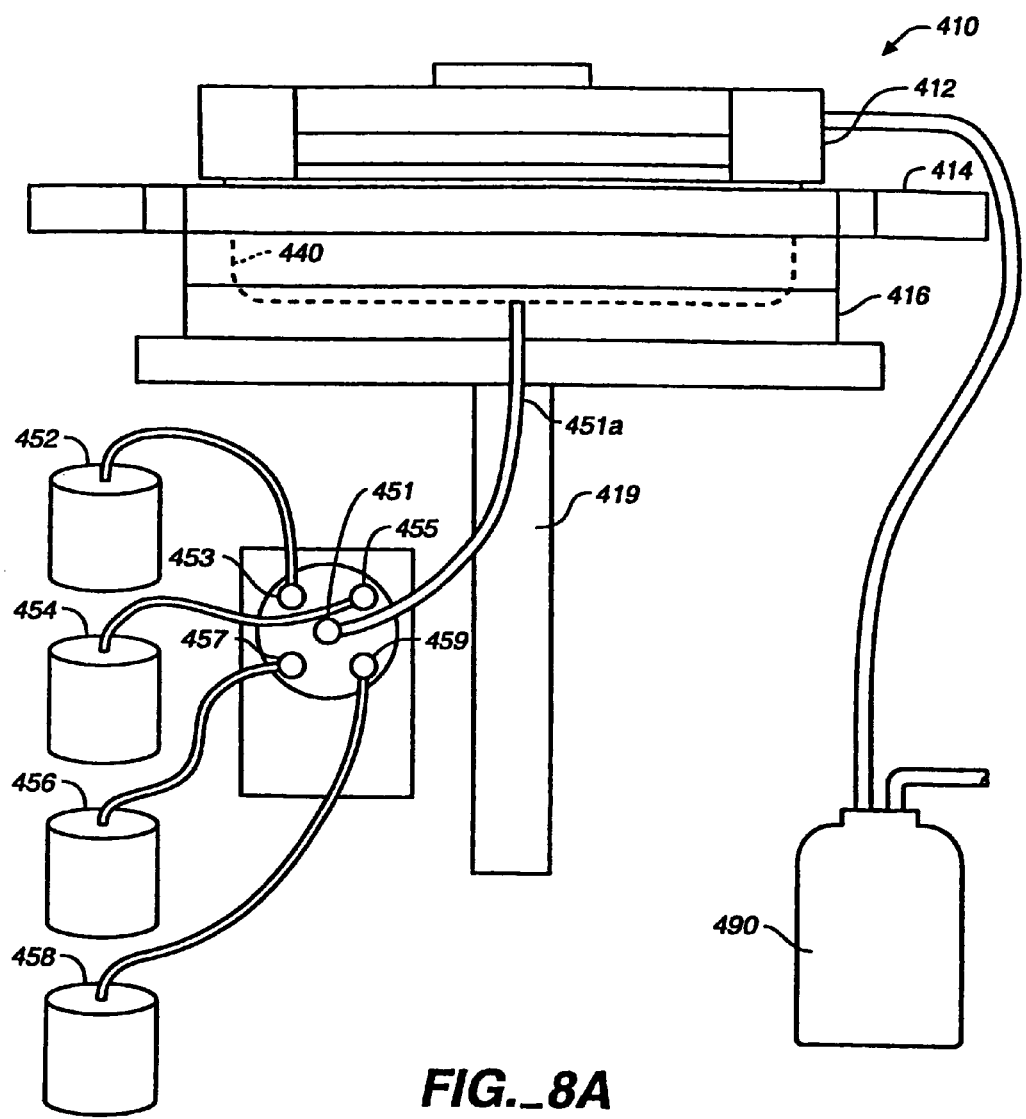
FIG._8A

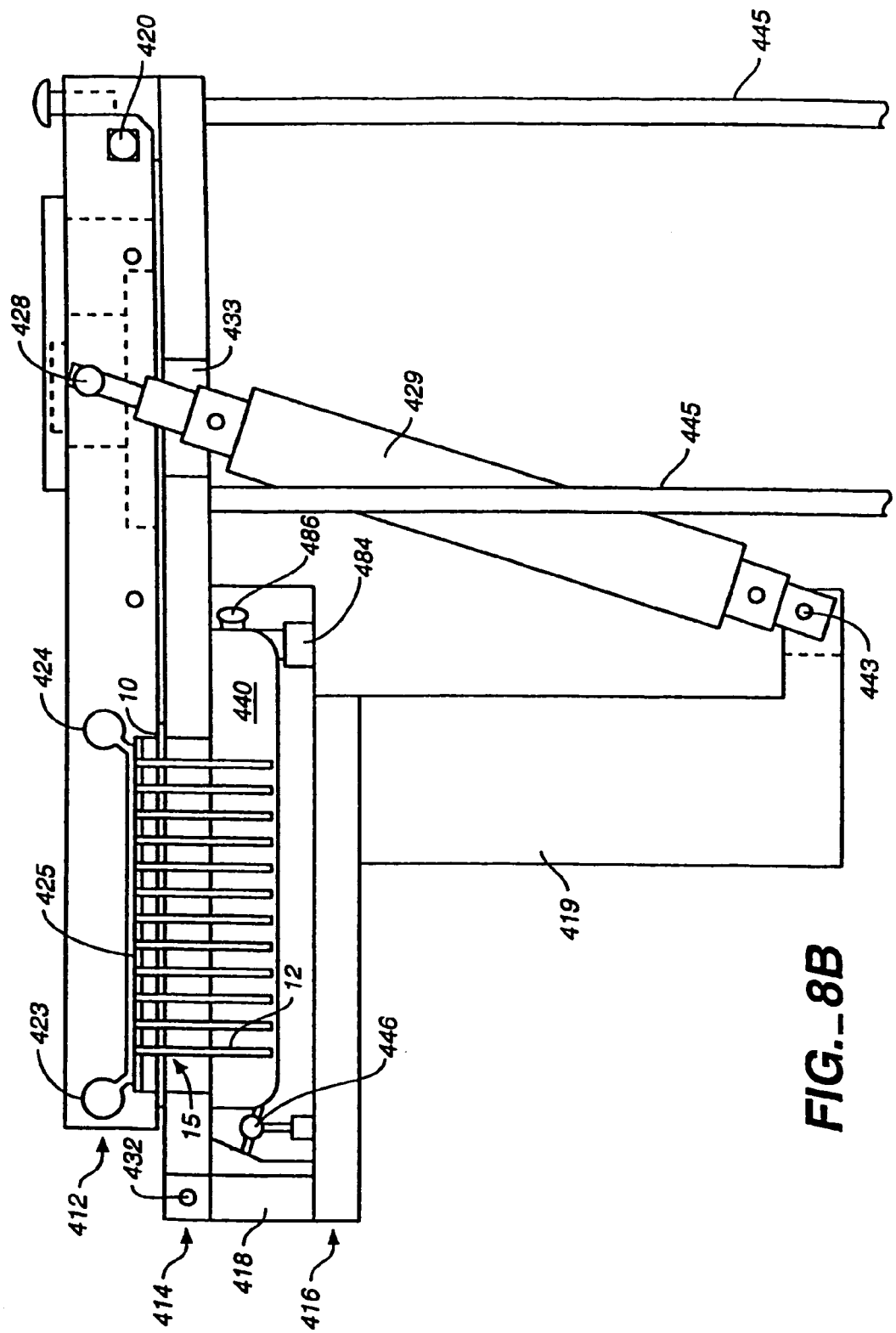

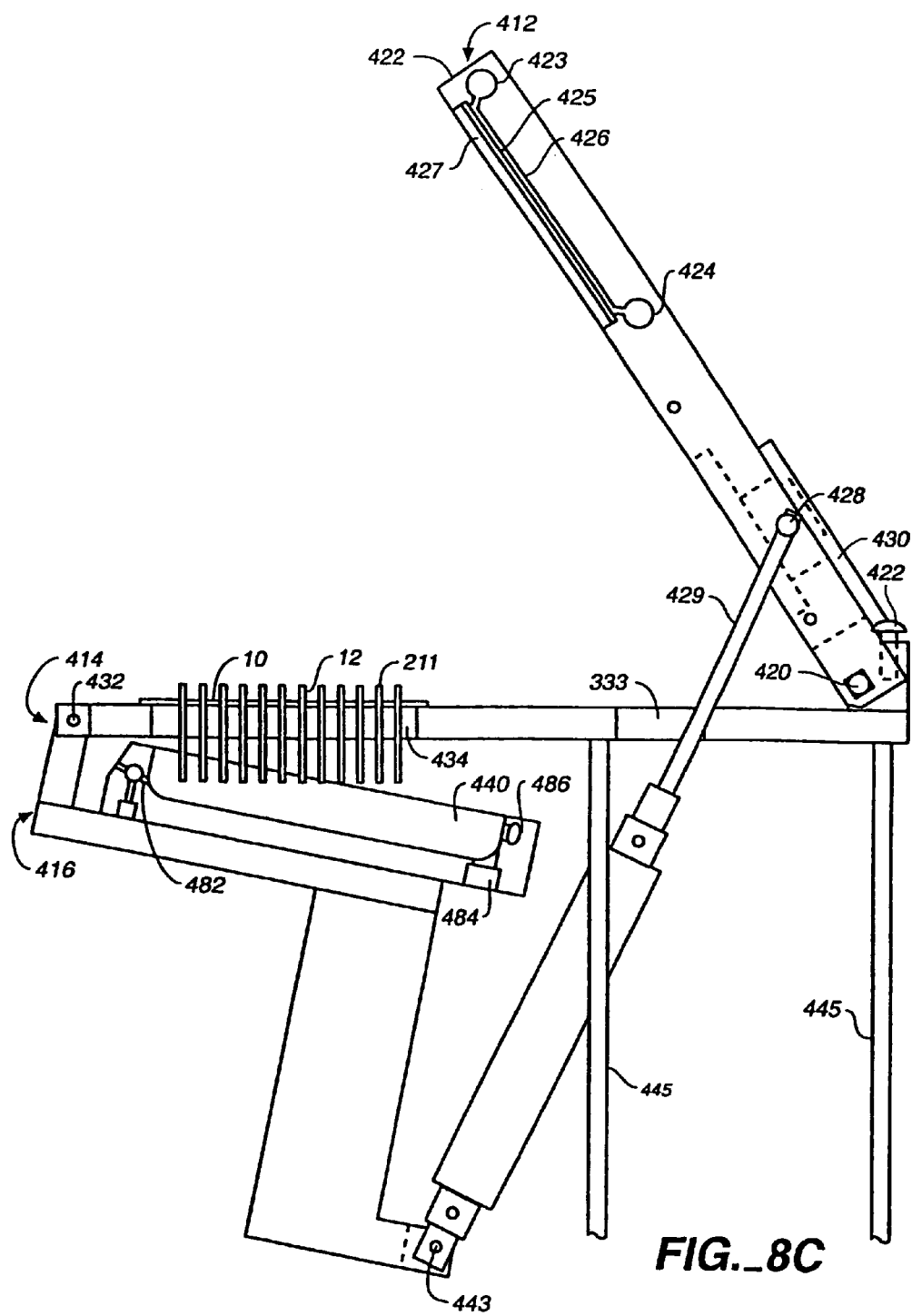
FIG._8C

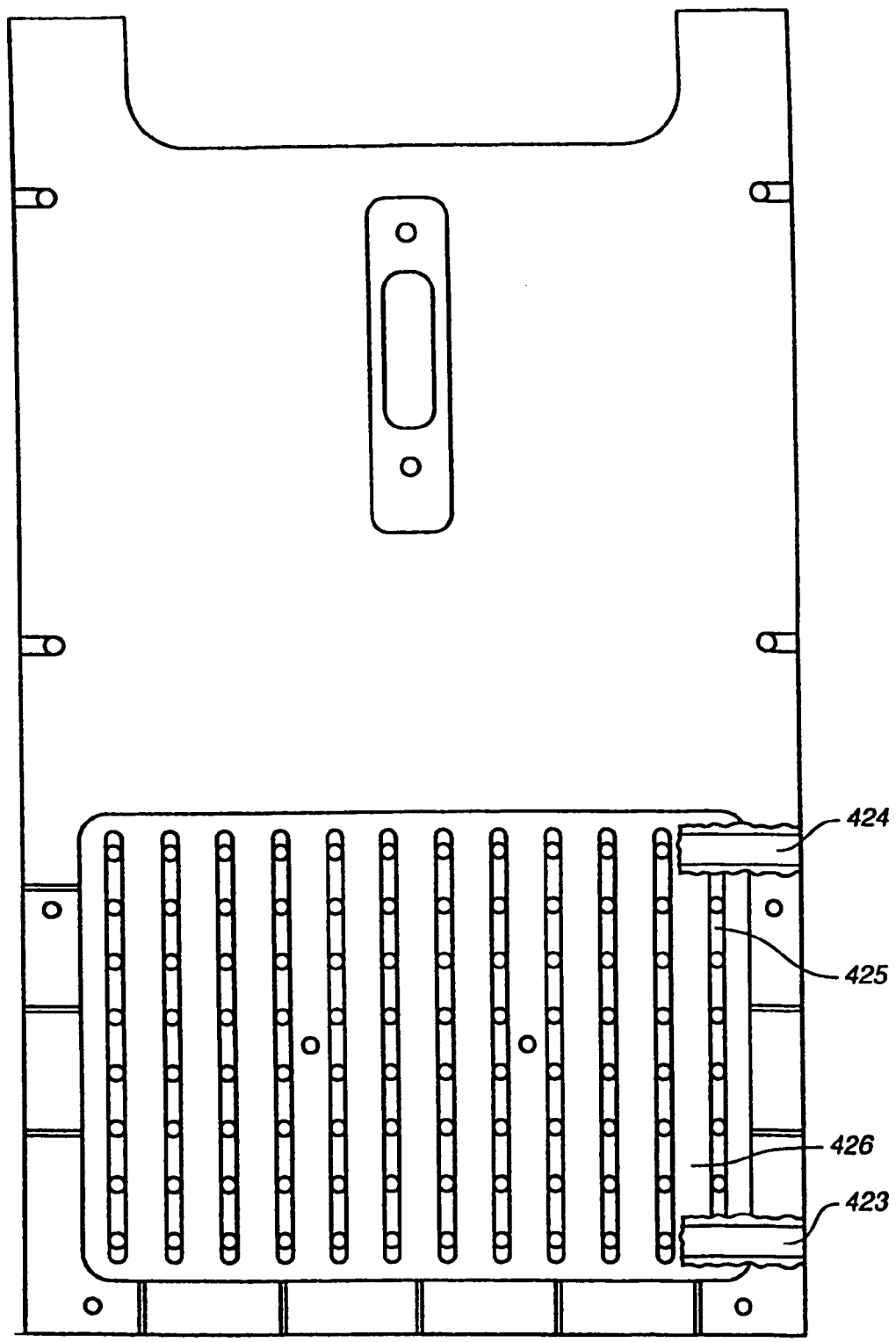
FIG._8D

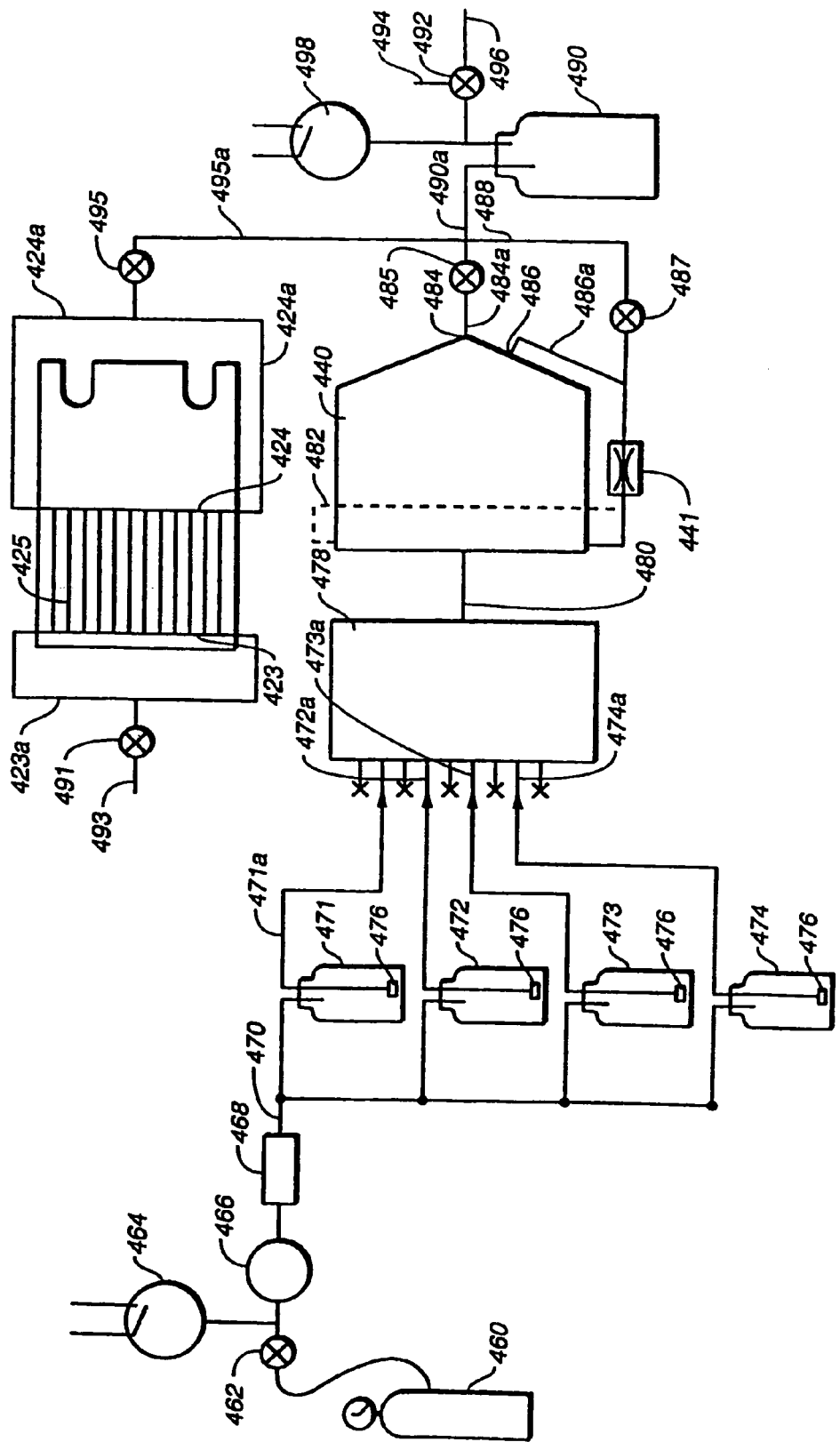
FIG._8E

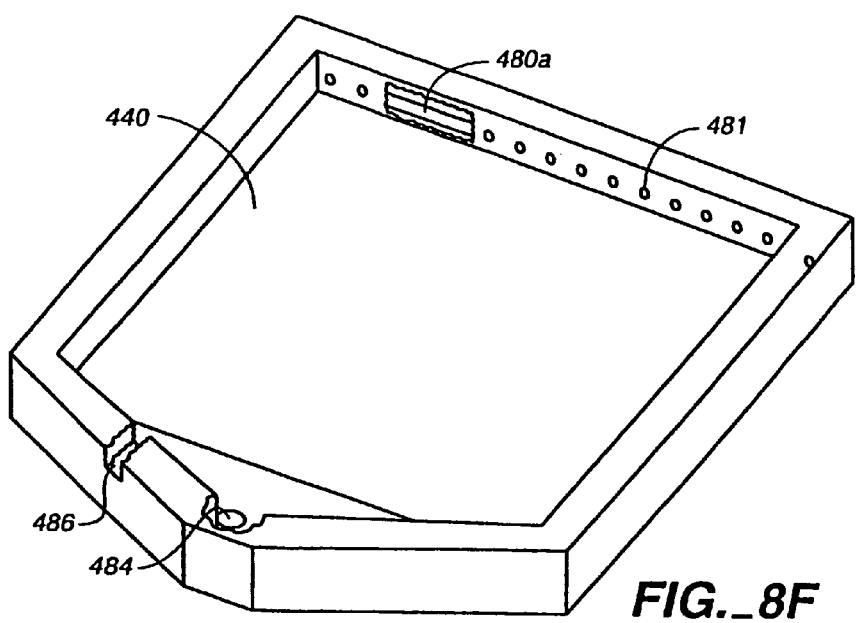
FIG._8F
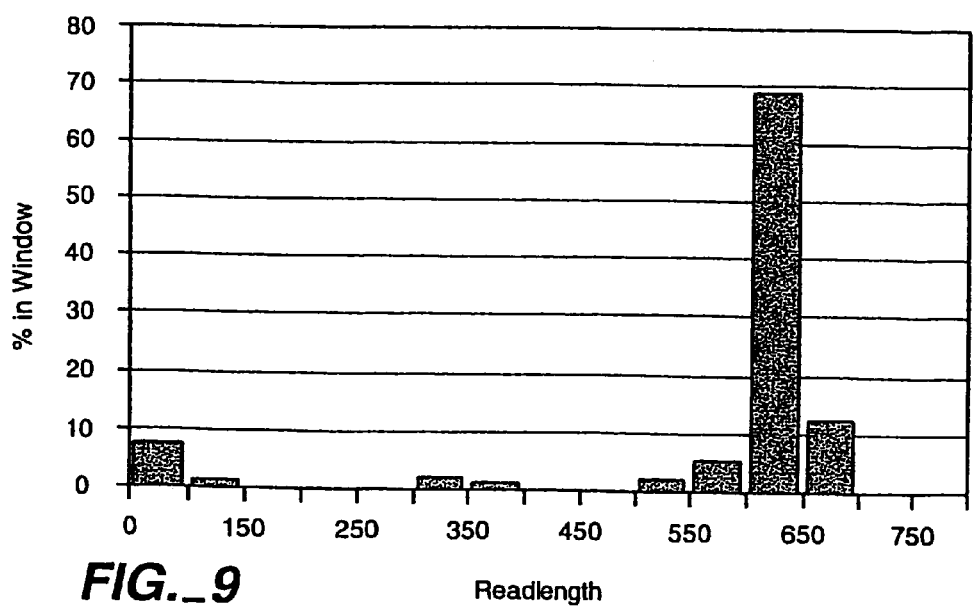
FIG._9

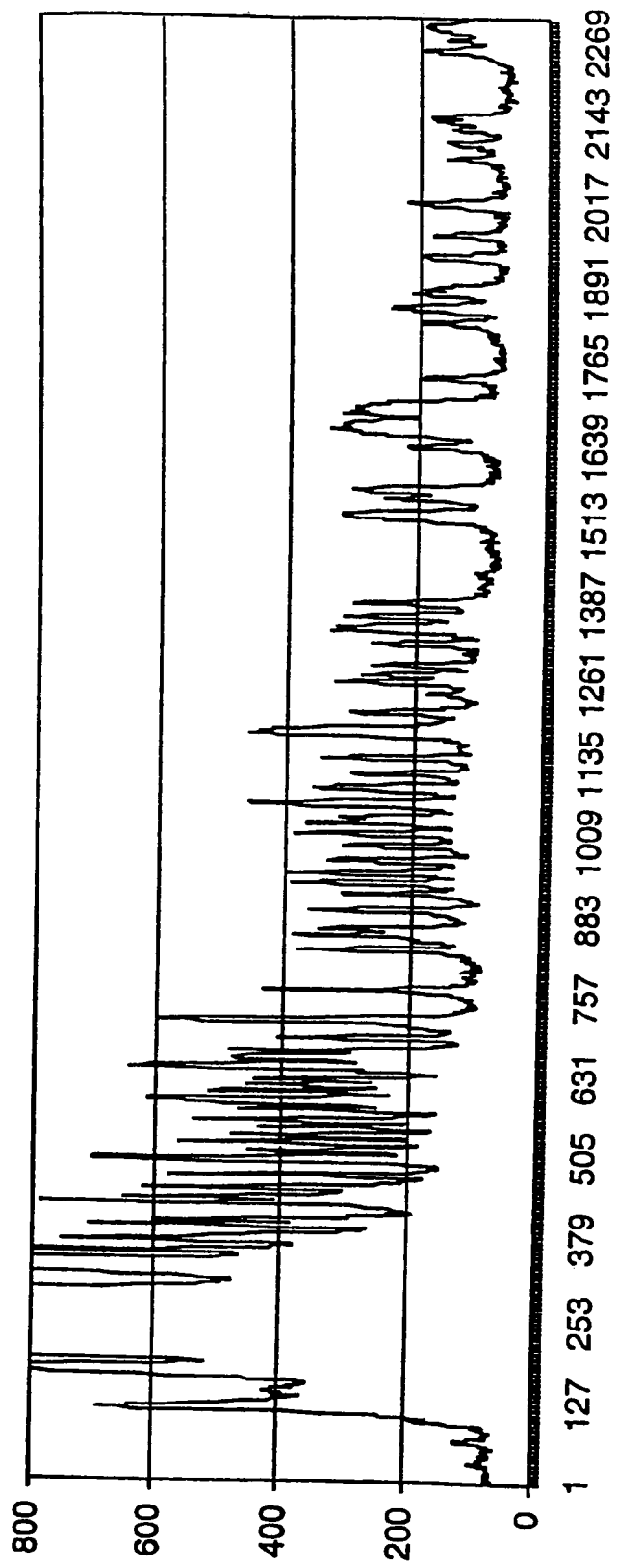
FIG._10

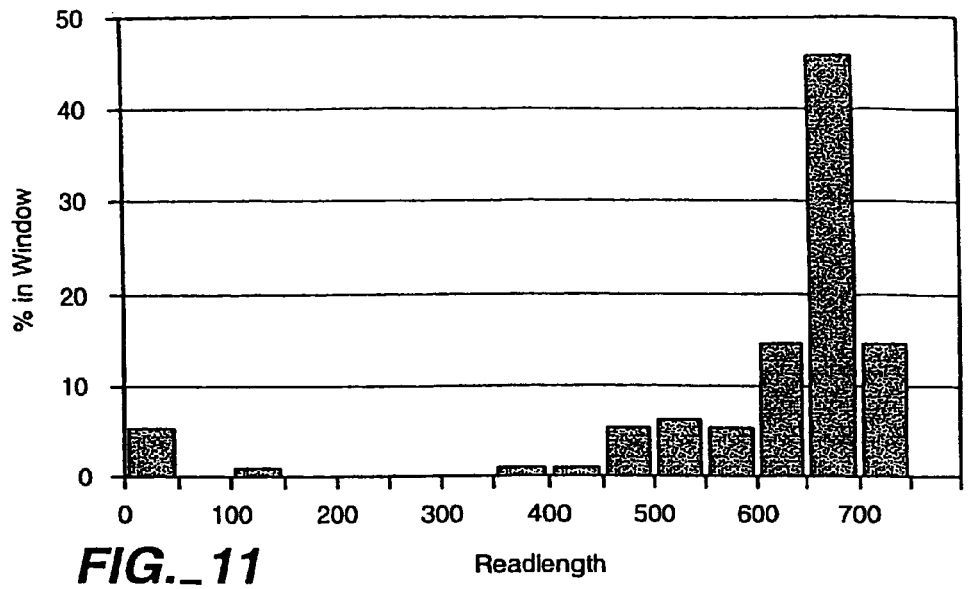
FIG._11
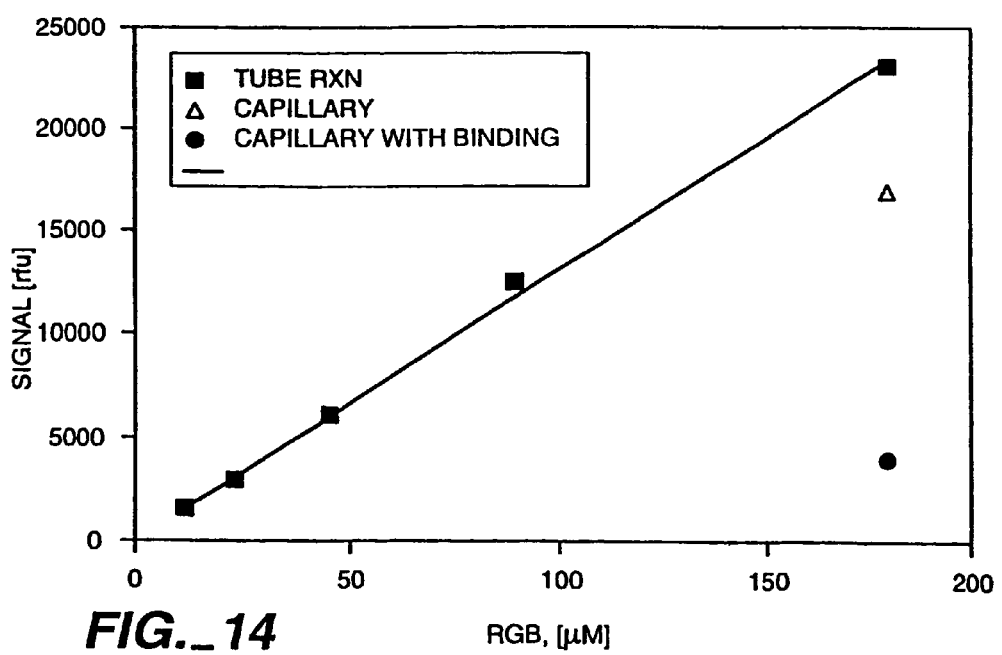
FIG._14

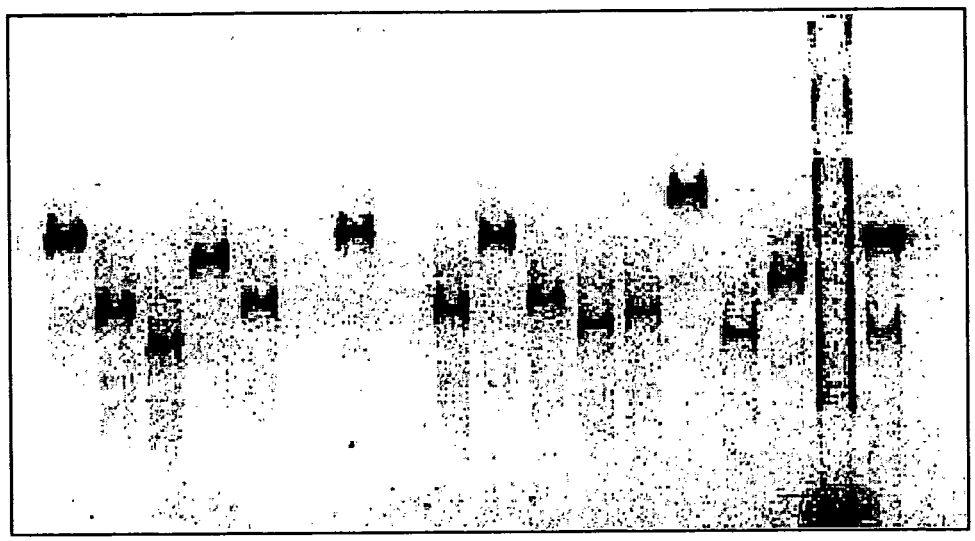
FIG._12A
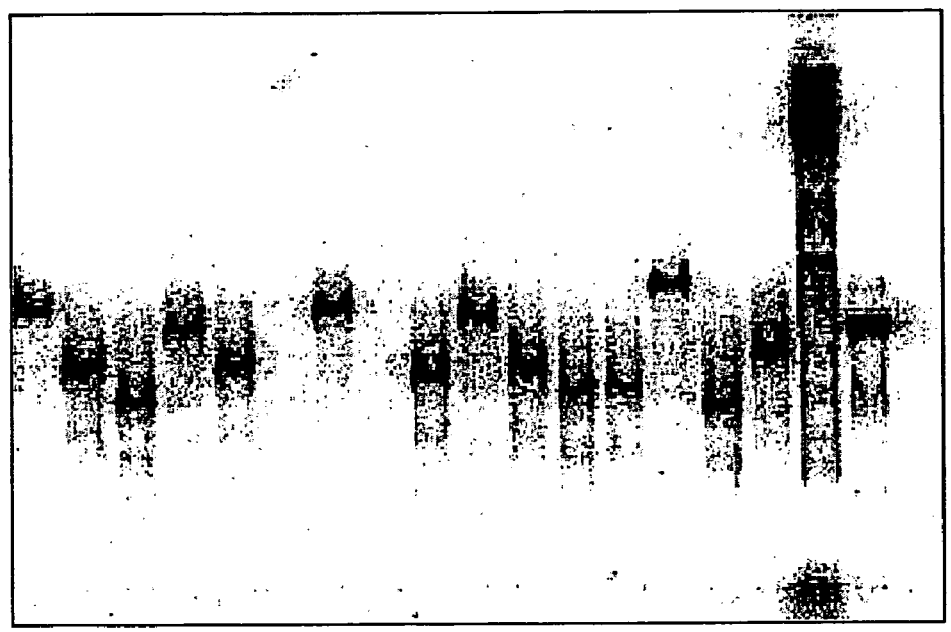
FIG._12B

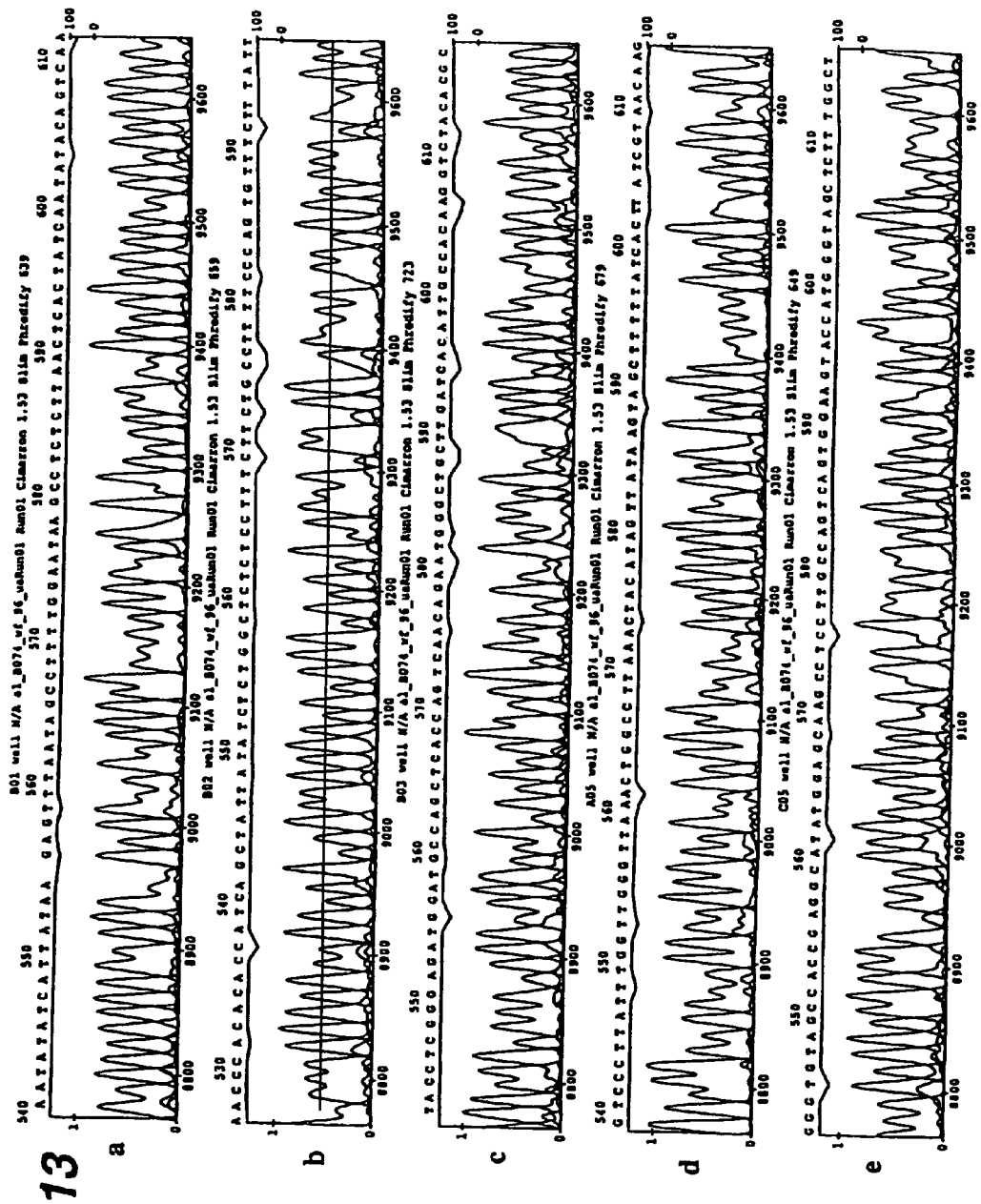
FIG._13

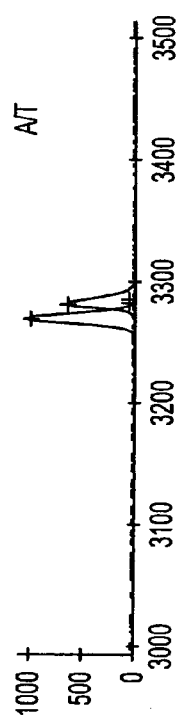
FIG. 26A
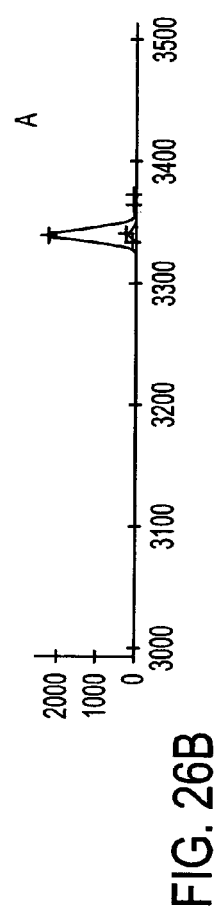
FIG. 26B
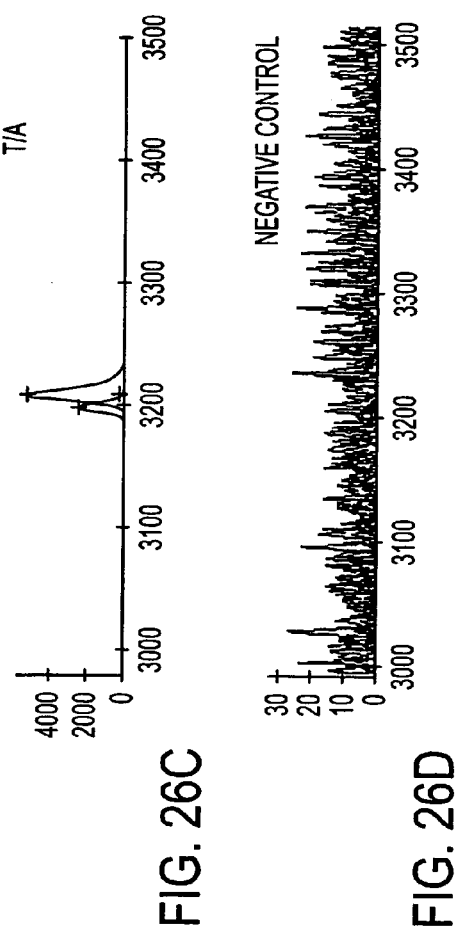
FIG. 26C
FIG. 26D

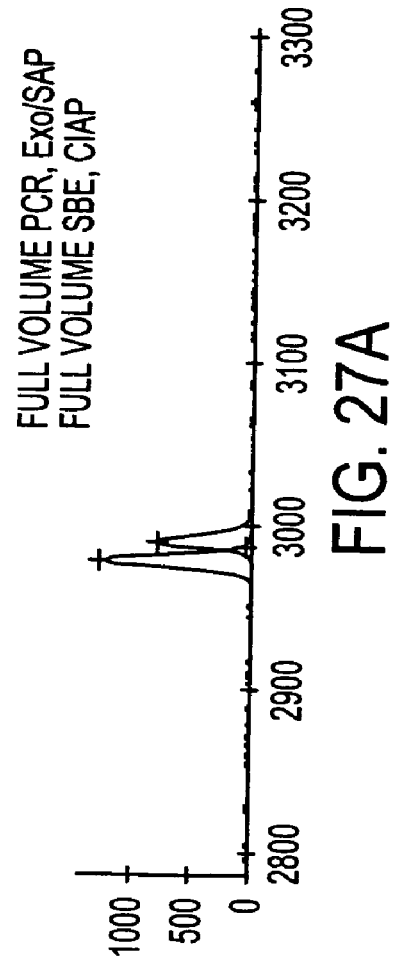
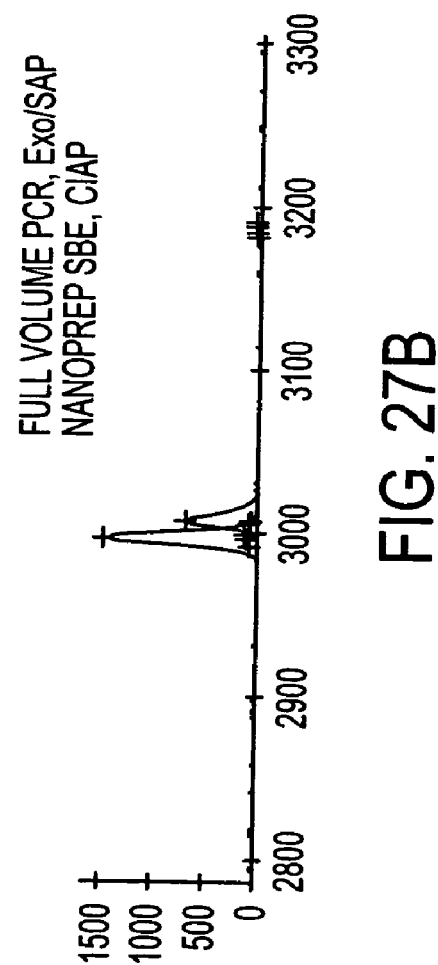
FIG. 27A
FIG. 27B

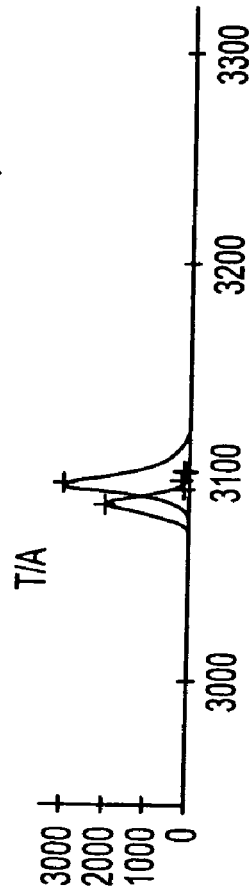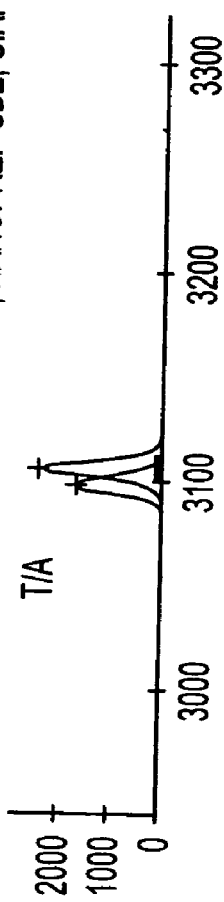

| SNP ID | % ACCURACY NANOVOLUME | % ACCURACY FULL-VOLUME | GENOTYPE |
|---|---|---|---|
| 422F | 100 | 100 | A/T |
| 422R | 100 | 100 | T/A |
| 423F | 91 | 100 | A/G |
| 423R | 100 | 100 | G/A |
| 425F | 100 | 97 | C/G |
| 429F | 97 | 100 | A/G |
| 429R | 100 | 100 | G/A |
| 431F | 91 | 97 | A/G |
| 460F | 100 | 100 | C/G |
| NEGATIVE CONTROL | 80 | 80 | - |
| AVERAGE OF 12 PRIMERS (9 ARE SHOWN) | 98 | 99 | - |

FIG. 30

METHODS AND APPARATUS FOR PERFORMING SUBMICROLITER REACTIONS WITH NUCLEIC ACIDS OR PROTEINS

CROSS-REFERENCE TO RELATED APPLICATIONS

This application claims priority from U.S. Provisional Application Ser. No. 60/146,732, filed Aug. 2, 1999; U.S. application Ser. No. 09/577,199, filed May 23, 2000, now U.S. Pat. No. 6,423,536; U.S. application Ser. No. 09/632,094, filed Aug. 2, 2000, now U.S. Pat. No. 6,489,112; U.S. Provisional Application Ser. No. 60/355,660, filed Feb. 8, 2002; U.S. Provisional Application Ser. No. 60/355,648, filed Feb. 8, 2002; and U.S. application Ser. No. 10/262,476, filed Sep. 30, 2002, now U.S. Pat. No. 6,927,045.

STATEMENT REGARDING FEDERALLY SPONSORED RESEARCH

This invention was made with government support. The government has certain rights in the invention.

FIELD OF THE INVENTION

This invention is in the field of biotechnology, and relates to methods and apparatus for preparing and performing small scale reactions that use nucleic acid or protein.

BACKGROUND OF THE INVENTION

The original goal of the federally-funded Human Genome Project had been to complete the sequence of the human genome at ten-fold coverage by the year 2005. With dramatic acceleration in pace, a partial draft has recently been presented. Rather than decreasing the need for rapid, inexpensive DNA sequencing, however, this feat has spurred the need for rapid, inexpensive sequencing of nucleic acids. Completion of the draft human genome sequence has also spurred a need for methods and apparatus for analyzing directly the complex collection of genome-encoded proteins, collectively termed the proteome.

With respect to DNA sequence needs, there is growing interest in sequencing the genomes of non-human organisms, including bacteria, plants and animals.

More importantly, the burgeoning fields of molecular pathology and pharmacogenomics will require the resequencing of multiple genes from individual patients. Molecular pathology relates to the diagnosis, and often formulation of a prognosis, for human diseases by identifying mutations in particular genes. Pharmacogenomics refers to understanding how allelic differences that exist in all human populations affect the therapeutic response, and susceptibility to side effects, of individuals to drugs.

As the need to sequence genes from individual patients grows, so will the demand for point of care sequencing capability. There will need to be a shift from large, centralized, high throughput DNA sequencing facilities that only exist at well-funded academic research centers and genomics companies to small, less complicated, middle-throughput gene sequencing systems that can be installed in the majority of hospitals and clinics. This shift in the market for DNA sequencing technologies will put a premium on reducing the cost of reagents and making the sample processing steps as simple and seamless as possible.

In the late 1970s, Sanger et al. developed an enzymatic chain termination method for DNA sequence analysis that produces a nested set of DNA fragments with a common starting point and random terminations at every nucleotide throughout the sequence. Lloyd Smith, Lee Hood, and others modified the Sanger method to use four fluorescent labels in sequencing reactions enabling single lane separations. This resulted in the creation of the first automated DNA sequencers, which used polyacrylamide slab gels for separations. More recently, fluorescent energy-transfer dyes have been used to make dye sets that enhance signals by 2- to 10-fold and simplify the optical configuration.

Automated fluorescent capillary array electrophoresis (CAE) DNA sequencers appear to be the consensus technology to replace slab gels. Capillary gel electrophoresis speeds up the separation of sequencing products and has the potential to dramatically decrease sample volume requirements. The 96-channel capillary electrophoresis instrument, MegaBACE™, which is commercially available from Amersham Biosciences, Inc. (Sunnyvale, Calif.), uses a laser-induced fluorescence (LIF) confocal fluorescence scanner to detect up to an average of about 625 bases per capillary (Phred 20 window) in 90 minute runs with cycle times of two hours. Confocal spatial filtering results in a higher signal-to-noise ratio because superfluous reflections and fluorescence from surrounding materials are eliminated before signal detection at the photomultiplier tube (PMT). Accordingly, sensitivity at the level of subattomoles per sequencing band is attainable. Confocal imaging is also particularly important in microchip analysis systems using capillary electrophoresis, where the background fluorescence of a glass or plastic microchip may be much higher than that of fused silica capillaries. Capillary array electrophoresis systems will solve many of the initial throughput needs of the genomic community for DNA analysis. However, present methods for low volume sample preparation still present a significant barrier to increased throughput and reduced cost.

While fluorescent DNA sequencers are improving the throughput of DNA sequence acquisition, they have also moved the throughput bottleneck from sequence acquisition back towards sample preparation. In response, rapid methods for preparing sequencing templates and for transposon-facilitated DNA sequencing have been developed, as have magnetic bead capture methods that eliminate centrifugation. Thermophilic Archae DNA polymerases have been screened and genetically engineered to improve fidelity, ensure stability at high temperatures, extend lengths, and alter affinities for dideoxynucleotides and fluorescent analogs. These improvements have resulted in lower reagent costs, simpler sample preparation, higher data accuracy, and increased read lengths.

The sequencing community has also developed higher throughput methods for preparing DNA templates, polymerase chain reaction (PCR) reactions, and DNA sequencing reactions. Sample preparation has been increasingly multiplexed and automated using 96- and 384-well microtiter, multi-channel pipettors, and laboratory robotic workstations. In general, these workstations mimic the manipulations that a technician would perform and have minimum working volumes of about a microliter, although stand-alone multi-channel pipettors are being used to manipulate smaller volumes.

A typical full-scale sample preparation method for DNA shotgun sequencing on capillary systems begins by lysing phage plaques or bacterial colonies to isolate subcloned DNA. Under some circumstances it may be desirable to PCR-amplify the subcloned DNA insert to exponentially increase its concentration in the sample. Next, exonuclease I (ExoI) and arctic shrimp alkaline phosphatase (SAP) are added to perform an enzymatic cleanup reaction to remove primer and excess dNTPs that interfere with cycle sequencing. ExoI is used to degrade the single-stranded primers to dNMPs without digesting double-stranded products. SAP converts dNTPs to dNPs and reduces the dNTP concentration from 200 µM, as used for the PCR reaction, to less than 0.1 µM for use with fluorescent sequencing. The reaction is performed at 37° C. and then heated to 65° C. irreversibly denature the ExoI and SAP.

Because PCR amplification can produce excess template DNA for cycle sequencing, the ExoI/SAP treated PCR sample can be diluted five-fold before cycle sequencing. This reduces the concentration of contaminants into a range that causes less interference with capillary electrophoresis analysis. Cycle sequencing reagents are added, typically with fluorescently labeled dye primers or terminators and the reaction is thermal cycled to drive linear amplification of labeled fragments. Finally, after cycling, the samples are post-processed, typically by ethanol precipitation or spin filtration, resuspended in formamide, another denaturant, or water, and the sample is electrokinetically injected into the capillary electrophoresis system.

This workflow has resulted in a dramatic improvement in the performance of the MegaBACE™ system, and similar work flows currently appear to be the methods of choice for other capillary electrophoresis systems as well. Using actual samples from single plaques and colonies of human genomic random subclones or Expressed Sequence Tags (ESTs), this workflow with linear polyacrylamide as a separation matrix has improved the success rate of samples over 200 base pairs from about 60% to 85–90%, and has improved the average read length from about 400 to greater than 600 bases. Furthermore, this method has proven to be quite robust.

While the above sample preparation methods have greatly increased throughout, the cost of reagents remains a major component of the cost of sequencing. Capillary electrophoresis requires only subattomoles of sample, but presently samples are prepared in the picomole range. Reducing the reaction volume will therefore reduce the cost of DNA sequencing and still provide enough material for analysis. However, substantial reductions in reaction volume can only be achieved if satisfactory methods can be developed for manipulating and reacting samples and reagents. Ideally, such a method would be automated and configured to produce multiple samples at one time. Moreover, it would be desirable to integrate such a method as a module capable of interfacing with additional components, such as capillary electrophoresis and a detector for separation and analysis.

Several devices have been designed to aid in the automation of sample preparation. For example, U.S. Pat. No. 5,720,923 describes a system in which small cycling reactions take place in tubes with diameters as small as 1 mm. The tubes are subsequently exposed to thermal cycles produced by thermal blocks to effect the desired reaction. Multiple samples may be processed in a single tube by drawing in small amounts of sample, each of which are separated in the tube by a liquid which will not combine with the sample. Fluid moves through the tubes by means of a pump. These features are incorporated into a system which automatically cleans the tubes, moves sample trays having sample containing wells, and brings the tubes into contact with the wells in the sample trays.

U.S. Pat. No. 5,785,926 discloses a system for transporting small volumes of sample. In this system, at least one capillary tube is used to transport small amounts of sample. A precision linear actuator connected to a computer controlled motor acts as a pneumatic piston to aliquot and dispense liquid using the tube. The sample amount is monitored by an optical sensor that detects the presence of liquid within the capillary segment. The system includes a fluid station containing liquids to be deposited and a positioning device for positioning the transport capillary.

U.S. Pat. No. 5,897,842 discloses a system for automated sample preparation using thermal cycling. In this system a reaction mixture is pumped into a capillary tube. One end of the tube is sealed using pressure from an associated pump while the other end is sealed by pressing the tube against a barrier. The pump also serves to move fluid within the tube. Once the ends are sealed, the tube is exposed to thermal cycles. In this system a robotic transfer device moves the tubes between the sample preparation station where the pump loads the components of the reaction mixture into the tubes and the thermal cycling station.

In the systems discussed above, it is necessary to first mix together a sample, such as DNA template for sequencing, and reagents, prior to introducing the mixture into a reaction chamber. This intermediate mixing step inevitably requires additional reagent and sample handling steps that results in wastage. For example, if separate micropipets are used to dispense sample and reagent into a mixing chamber, small amounts of sample and reagent will be retained in the respective pipets, and reaction mixture will be retained in the mixing chamber. In a high throughput system the cost of this wastage and providing new or properly cleaned pipets and mixing chambers rapidly mounts. Extent of wastage is often exacerbated by the need to dispense relatively large volumes of liquids containing reaction components at low concentration as a strategy to compensate for inaccuracies in dispensing low volumes of higher concentration liquids. Usually, after the reaction mixture is formed, only a small proportion is required for analysis, and the remainder is discarded.

Thus, there exists a need for means by which a biological sample to be analyzed could be introduced into a reaction chamber without the need to first mix the sample with the reagents necessary to effect the reaction.

U.S. Pat. No. 5,846,727 discloses affinity-capture methods wherein template DNA is immobilized inside a glass capillary tube that serves as a reaction chamber for thermal cycling. The capillary is first prepared by immobilizing biotin molecules to the inner surface of the capillary, followed by charging the column with avidin or streptavidin which binds tightly the biotin. Template DNA to be sequenced is covalently linked to a biotin moiety by PCR, and is then exposed to the avidin inside the capillary. This results in immobilization of the template to the capillary wall through a biotin-avidin-biotin linkage. After unbound template is washed away, sequencing reagent is added, and the contents of the capillary are subjected thermal cycling to activate the sequencing reaction. In this manner it is unnecessary to mix template DNA with sequencing reagent prior to loading the capillary.

However, the method just described requires that biotin be linked to the template DNA by PCR, necessitating setting up and carrying out a reaction even before the sequencing reaction. This requisite preliminary step adds to the time and cost associated with acquiring the sequence data. Furthermore, the immobilization of the DNA is effectively irreversible because the biotin-avidin linkage is so strong it can only be broken using agents that denature avidin, a treatment that would also denature any other protein components in a reaction. As a result the template DNA must stay bound to the inner surface of the capillary. Because the DNA is not free in solution, additional time is required for reaction components to diffuse to the walls where they can interact with the DNA. Furthermore, when it is desired to recycle the capillary, it is necessary to remove the template DNA via denaturation of the avidin, washing and then recharging of the avidin in the capillary, all of which add to time and reagent costs.

Thus, there is continued need in the art for methods to introduce molecules into reaction chambers without an initial sample-reagent mixing step, without the need to attach an affinity capture moiety to all the molecules in the sample, and wherein template immobilization is reversible. In this way reagent costs would be minimized and processing speed maximized.

Capillary array electrophoresis systems and capillary electrophoresis microchip analytical systems can detect sub-attomoles of DNA sequencing reaction products. This extraordinary sensitivity comes at the cost of reduced tolerance, compared to slab gels, for deviations from the ideal amount of template DNA in the sequencing reactions. For example, if there is too little template DNA in the sequencing reaction, there will be poor yield of fluorescently labeled primer extension products. This results in weak signal strength when the reaction products are scanned by the laser. This prevents the software that analyzes the chromatogram from adequately performing spectral separation, resulting in shorter than average sequence read lengths; the reaction will have to be repeated or the sequence information will be lost.

Too much template DNA causes problems as well, due to overloading of the capillary. While there is adequate yield of fluorescently labeled reaction product, if the template is in excess, it competes with sequencing products for entry into the capillary during electrokinetic injection. The presence of the large template DNA molecules can result in an overall reduction, or sudden drop in capillary current, which can manifest itself in a variety of ways. overloading can cause weak signal strength, late appearance of interpretable fluorescence intensity peaks in the chromatogram, and poor resolution of the reaction products because the fluorescence emission is broad and diffuse. All these effects lead to shorter reads and lower sequencing data quality.

The problem of overloading is typically solved by either diluting the sequencing reaction, or carefully titrating the amount of template DNA introduced into the sequencing reaction. While both these solutions are simple in principle, the former requires repeating the analysis of the reaction, and the latter is difficult to implement using conventional means in a high-throughput system. These means include detecting, and comparing to standard concentration curves, the quantity of fluorescent dye that binds DNA in a sample, or measuring the absorbance of ultraviolet light at 260 nm wavelength, which can be converted into an absolute measure of DNA concentration. Thus, there is continued need in the art for methods to titrate the quantity of template DNA for sequencing reactions to be analyzed using high-throughput capillary electrophoresis systems, where minimizing cost and maximizing speed are crucial.

There is an additional need for an automated system that is able to perform small-scale thermal cycling reactions in a highly parallel manner. The system should allow for rapid preparation of cycling reactions with minimal consumption of reagents. The combination of reducing the amount of reagents required for a reaction and reducing the time required for a reaction will greatly reduce the overall cost of preparation of cycling reactions.

With respect to proteomics, analysis of the proteome requires separation, quantification and identification of large protein collections.

Typically, such analysis is achieved by a combination of different techniques, such as 2-D electrophoresis separation, followed by enzymatic digestion and identification by matrix-assisted laser desorption/ionization mass spectrometry (2D PAGE-MALDI/MS) or by electrospray ionization mass spectrometry (2D PAGE-ESI/MS). Another common approach is LC/LC-MS/MS, i.e., proteins are digested, separated by strong cation exchange liquid chromatography and reversed phase liquid chromatography (LC/LC), and then identified by tandem mass spectrometry (MS/MS). Current limitations include the requirement for extensive sample preparation prior to proteolytic digestion, analyte loss, and low reaction efficiencies at low protein concentrations.

In an alternative, methods and apparatus have been developed that permit both partial purification and mass spectal identification using a single derivatived laser desorption probe. See, e.g., U.S. Pat. Nos. 6,225,047, 6,124,137, 5,719, 060. Such methods, however, require specialized equipment and familiarity with mass spectrometers.

There is, therefore, a continued need in the art for an automated system that is able to perform small-scale proteomic reactions in a highly parallel manner. The system should allow for rapid preparation of enzymatic reactions with minimal consumption of reagents. The combination of reducing the amount of reagents required for a reaction and reducing the time required for a reaction will greatly reduce the overall cost of preparation of proteomic reactions while a highly parallel system will improve throughput.

SUMMARY OF THE INVENTION

Accordingly, certain embodiments of the instant invention are set forth in the following numbered paragraphs:

1. A system for performing small scale reactions, the system comprising: a capillary cassette having a substrate and a plurality of capillaries extending through said substrate, wherein each of said capillaries has first and second open ends on opposing sides of said substrate; a pair of membranes orientated and spaced such that they may temporarily seal the opposed ends of said capillaries; a thermal cycler having an internal chamber of sufficient capacity to hold said capillary cassette and said membranes; and an automated transfer device positioned to contact and move the capillary cassette to a location where the ends of the capillary may be sealed by the pair of membranes and the capillary cassette with ends sealed by said membranes may be located within the internal chamber of the thermal cycler.

2. The system of paragraph 1, further comprising a dispenser that dispenses a fluid from capillaries of the capillary cassette onto a location on a receiving substrate, wherein the automated transfer device may move the capillary cassette in relation to said dispenser and receiving substrate such that the fluid contained within the capillaries of the capillary cassette are dispensed onto the substrate.

3. The system of paragraph 2, wherein the dispenser is a centrifuge.

4. The system of paragraph 2, wherein the dispenser is an air displacement dispenser.

5. The system of paragraph 2, further comprising an analytical stage positioned such that the automated transfer device may transfer said capillary cassette in relation to said dispenser such that contents within said capillary cassette may be dispensed onto a substrate located upon said stage.

6. The system of paragraph 5, wherein said substrate is a sample preparation microchip and the automated transfer device is disposed to dispense the capillary cassette directly into a plurality of sample preparation microchip sample receiving wells.

7. The system of paragraph 5, wherein said substrate is an array of capillaries and the automated transfer device is dispersed to disperse the capillary cassette directly into the capillaries.

8. The system of paragraph 2, wherein said substrate is a multiwell plate.

9. The system of paragraph 1 wherein the capillaries have an interior volume of 10–1000 nL.

10. The system of paragraph 1, further including a capillary cassette wash station, wherein said automated transfer device may transfer a capillary cassette into contact with said wash station, said wash station directing a wash solution through the capillaries of the capillary cassette when said capillary cassette is placed within said wash station.

11. The system of paragraph 10, wherein said wash station has a wash solution tank and an upper wash manifold that may be moved to a position above said wash solution tank, wherein a wash fluid may be introduced into said wash solution tank and drawn by suction into the wash manifold when the capillary cassette is inserted into said wash station.

12. The system of paragraph 11, wherein said wash station further includes a plurality of wash fluid bottles each containing a wash fluid and a selector valve allowing selection of a wash fluid from one of said bottles to fill said wash solution tank.

13. The system of paragraph 1, further comprising an electronic control which may be programmed to send electronic instructions to components of the system.

14. The system of paragraph 1 wherein said pair of membranes are affixed to opposing sides of the internal chamber of the thermal cycling device.

15. The system of paragraph 1 further comprising a plurality of microplate holder magazines which dispense microplates to a location where said automated transfer device may contact and move the microplates.

16. The system of paragraph 1 wherein said membranes are deformable membranes held with a spring bias to temporarily seal the ends of the capillaries.

17. A system for nanoscale reaction preparation, the system comprising: a capillary cassette including a substrate and a plurality of capillaries extending through said substrate, each capillary having an internal volume of between 10 nl and about 1 uL, wherein each of said capillaries has a first and a second open end on opposing sides of said substrate, wherein the length of the capillary extending through substrate on one side of the substrate is matched to be shorter than the depth of a microplate well; a multiwell plate having a plurality of wells into which the capillaries of the capillary cassette may be inserted; a dispenser that dispenses fluid contained within the capillaries of the capillary cassette into wells of said multiwell plate when said capillary is transported to the dispenser; an automated transfer robot having a transfer head to carry articles selected from the group comprising capillary cassettes, multiwell plates, and multiwell plates with capillaries of a capillary cassette inserted into the wells of the multiwell plates; a pair of opposing membrane surfaces, wherein the ends of the capillaries may be temporarily sealed by pressing the membranes against said ends; and a thermal cycler having an internal chamber of sufficient capacity to hold said capillary cassette and said membranes when said membranes are sealing the ends of the capillaries of the capillary cassette, wherein the thermal cycler is disposed such that the automated transfer robot may place a capillary cassette into an internal chamber within said thermal cycler wherein said membranes may seal the end of the capillaries of said capillary cassette within said internal chamber.

18. The system of paragraph 17 wherein said dispenser is an electrokinetic injector.

19. The system of paragraph 17 wherein said dispenser is a centrifuge.

20. The system of paragraph 17 wherein said dispenser is an air displacement head.

21. The system of paragraph 17 wherein said dispenser is disposed to dispense liquid from the capillaries onto an analytical substrate located on an analytical stage.

22. The system of paragraph 17, further comprising a capillary cassette wash station, wherein said automated transfer device may transfer a capillary cassette into contact with said wash station, said wash station directing a wash solution through interiors of the capillaries of the capillary cassette when said capillary cassette is placed within said wash station.

23. The system of paragraph 22, wherein said wash station includes a lower wash solution tank and an upper wash manifold, wherein a wash fluid may be introduced into said wash solution tank and drawn by suction into the wash manifold when the capillary cassette is inserted into said wash station.

24. The system of paragraph 23, wherein said wash station further includes a plurality of wash fluid bottles and a selector valve in fluid communication with said bottles for selection of a wash fluid to fill said wash solution tank.

25. The system of paragraph 17, further comprising an electronic control, said control sending electronic instructions to effect programmed operation of said system.

26. A system for preparing nanoscale reactions, the system comprising: a substrate having integrally associated elongate submicroliter volume reaction containers having two opposing ends; a reaction mixture contained within said reaction containers; a pair of membranes disposed to temporarily seal said opposing ends of said reaction containers; a thermal cycler having an internal chamber of sufficient dimension to receive said substrate with associated elongate reaction chambers sealed by said membranes.

27. The system of paragraph 26, wherein said substrate has capillaries extending through said substrate, wherein said capillaries act as the reaction chambers.

28. The system of paragraph 26, wherein said elongate reaction containers pass through the thickness of said substrate.

29. The system of paragraph 26, wherein said thermal cycler circulates heated air through a continuous circuit, wherein said internal chamber is part of said continuous circuit.

30. The system of paragraph 29, wherein said continuous circuit may be vented by blocking a section of said internal passageway and venting said heated air thereby allowing rapid temperature adjustment of said heated air.

31. The system of paragraph 30, wherein said internal chamber contains said membranes mounted on opposing surfaces of said internal chamber.

32. The system of paragraph 31, wherein at least one of said membranes is mounted within said internal chamber with a spring bias which provides a sealing force of said membranes against said ends of said reaction containers.

33. The system of paragraph 26, further comprising a means for dispensing said reaction containers.

34. The system of paragraph 26, further comprising a means for combining reagents to form said reaction mixture and a means for filling said reaction containers with said reaction mixture.

35. The system of paragraph 26, further comprising a wash station which may hold and wash said reaction containers.

36. A method to prepare nanoscale thermal cycling reaction mixtures, the steps comprising; combining compounds to form a reaction mixture; introducing said reaction mixture into a plurality of reaction containers disposed on a substrate, each reaction container having an internal volume less than one microliter and having a first and second open end; temporarily sealing the ends of reaction containers by pressing a pair of opposing membranes against a first and second set of reaction container ends; exposing the sealed reaction containers to temperature cycles to effect a reaction in the reaction mixture; and dispensing the reaction containers onto a substrate.

37. The method of paragraph 36 wherein the steps of combining compounds to form a reaction mixture includes the steps: metering an amount of a first liquid reaction component by placing one end of a plurality of capillaries of a capillary cassette into contact with the first liquid reaction component wherein the capillaries fill by capillary action; dispensing the first liquid reaction component onto discrete locations on a substrate; metering an amount of a second liquid reaction component by placing one end of the capillaries of a capillary cassette into contact with the reaction reagents wherein the capillaries fill by capillary action; and dispensing the second liquid reaction component onto the discrete locations, thereby combining said first and second liquid reaction components to form a reaction mixture.

38. The method of paragraph 37 wherein the step of introducing said reaction mixture into a plurality of reaction containers is effected by providing a capillary cassette and dipping one open end of capillaries of the capillary cassette into contact with the reaction mixture so that the capillaries fill by capillary action.

39. The method of paragraph 36 wherein the steps of combining compounds to form a reaction mixture includes the steps: immobilizing a biomolecule sample on an interior surface of the reaction container; metering an amount of reaction reagents into the capillaries of the capillary cassette by placing one end of the capillaries of a capillary cassette into contact with the reaction reagents wherein the capillaries fill by capillary action, whereby the reaction reagents and the immobilized biomolecule combine to form the reaction mixture.

40. The method of paragraph 39, wherein the biomolecule is a nucleic acid.

41. The method of paragraph 36 wherein the steps of combining compounds to form a reaction mixture include the steps: coating a plurality of surface locations with a layer of desiccated reaction reagents; and adding to each surface location a nucleic acid sample in solution of sufficient volume to dissolve the solid layer of reaction reagents, thereby forming a reaction mixture.

42. The method of paragraph 36 wherein the steps of combining compounds to form a reaction mixture include the steps: coating an interior surface of each capillary in a capillary cassette with a layer of desiccated reaction reagents; and metering an amount of nucleic acid sample in solution into the capillaries of the capillary cassette by placing one end of the capillaries of a capillary cassette into contact with the nucleic acid sample in solution, whereby the capillaries fill by capillary action, whereby the solution allows the layer of reaction reagents to dissolve, forming the reaction mixture.

43. The method of paragraph 36, wherein the step of dispensing the reaction containers onto a substrate is effected by: placing the substrate with associated reaction containers in a centrifuge; positioning a substrate at a radially distal end of one open end of said reaction containers; and applying centrifugal force such that liquid reaction mixtures contained within said reaction containers are dispensed onto said substrate.

44. The method of paragraph 36, wherein the step of dispensing the reaction containers onto a substrate is effected by: displacing the contents of the reaction containers onto a substrate using air displacement.

45. The method of paragraph 36 wherein the step of temporarily sealing the ends of the reaction containers by pressing a pair of opposing membranes against a first and second set of reaction container ends is effected by: placing the reaction containers within an interior chamber of a thermal cycler, wherein when the reaction containers are enclosed within said thermal cycler, deformable membranes on opposing interior surfaces of said interior chamber temporarily seal the reaction containers' ends on each end of the reaction containers.

46. The method of paragraph 36 wherein the step of exposing the sealed reaction to temperature cycles to effect a reaction is effected circulating heated air past the reaction containers through a conduit which allows rapid venting of air to the exterior of said conduit to effect rapid temperature changes during the temperature cycles.

47. A thermal cycling device for exposing reaction mixtures to temperature cycles, the device comprising: a housing enclosing a continuous interior circuit passageway, said housing having a section that may be temporarily opened to allow access to the interior of the housing; a blower disposed within said circuit passageway to direct air flow in one direction in the internal circuit passageway; a heating element disposed in said internal circuit passageway such that air circulating within said passageway passes through said heating element; a sample holding compartment having two membranes positioned in opposing orientation within said sample holding compartment, wherein said membranes may be biased against opposing ends of containers inserted into the sample holding compartment; housing air vent which may be opened to rapidly exhaust heated circulating air; and a housing air intake for drawing air into said interior circuit passageway when the vent exhausts heated circulating air.

48. The thermal cycling device of paragraph 47 further comprising a temperature monitoring device disposed in the internal passageway proximate to a sample holding compartment.

49. The thermal cycling device of paragraph 47 further comprising at least one air diffuser disposed in the internal passageway between the blower and the sample holding compartment, said diffuser promoting uniform temperature in the air circulating in the internal passageway.

50. The thermal cycling device of paragraph 47 wherein at least one of the membranes within the sample holding compartment is spring biased.

51. The thermal cycling device of paragraph 47 further comprising insulation affixed to the surfaces of the interior circuit passageway.

52. The thermal cycling device of paragraph 47 further comprising an electronic control which sends instruction to components of the thermal cycling device.

53. The thermal cycling device of paragraph 47 wherein said vent is opened by moving a section of said housing located between said sample holding compartment and said air intake such that the internal passageway is at least partially restricted and an opening to outside said housing is created.

54. The thermal cycling device of paragraph 47 wherein the housing has a sealable opening to admit access to the sample holding compartment.

55. A method for performing reactions, the method comprising, a) introducing reaction mixtures into a reaction container set, each container in the set having two opposing ends and an internal volume between 10 to 1000 nl; b) temporarily sealing the ends of the reaction chambers by pressing a deformable membrane against the opposing ends of said reaction containers; c) effecting a reaction within said reaction containers; d) dispensing reaction mixtures onto discrete locations on a substrate; and e) combining said reaction mixtures with at least 1 .mu.l of a liquid reagent mixture.

56. The method of paragraph 55, further comprising the step of: f) reacting the completed reaction mixture with the liquid reagent mixture.

57. The method of paragraph 56, further comprising the step of: g) combining reacted mixtures of step f with a reaction reagent set to form a second reaction mixture set; h) introducing said second reaction mixture set into a second reaction container set, each reaction container having two opposing ends and an internal between 10 and 1000 nl; i) temporarily sealing the ends of the set of reaction containers by pressing deformable membranes against the opposing ends of said reaction containers; j) effecting a reaction within said second reaction container set; and k) dispensing reacted mixtures from said second reaction container set.

58. The method paragraph 57, wherein step f occurs under isothermal reaction conditions.

59. The method of paragraph 57, wherein the reaction mixture of step a is a PCR mixture, the liquid reagent mixture of step e contains exonuclease I and shrimp alkaline phospotase, and the second reaction mixture.

60. The method of paragraph 57 wherein steps c and j include exposing the reaction container sets to temperature cycles.

61. The method of paragraph 60 wherein the exposing reaction container sets to temperature cycles is effected by a circulating air thermal cycler.

62. The method of paragraph 57 wherein the second reaction container set is dispensed onto an analytical substrate.

63. The method of paragraph 57 wherein the second reaction container set is dispensed into the ends of capillaries in a capillary electrophoresis array.

64. The method of paragraph 57 wherein the second reaction container set is dispensed into the wells of a microplate.

65. A method of obtaining substantially the same quantity of nucleic acid from a first and a second sample, comprising: saturably binding nucleic acid from said first sample directly on an inner surface of a first capillary tube by contacting said inner surface with a solution comprising a nucleic acid and a chaotropic agent for a time sufficient for the nucleic acid to become saturably bound to said inner surface; and saturably binding nucleic acid from said second sample directly on an inner surface of a second capillary tube by contacting said inner surface with a solution comprising a nucleic acid and a chaotropic agent for a time sufficient for the nucleic acid to become saturably bound to said inner surface, wherein said inner surfaces of said first and second capillary tubes are capable of saturably binding substantially the same quantity of nucleic acid from each of said first and second samples, respectively.

66. The method of paragraph 65, wherein the quantity of nucleic acid saturably bound to the inner surfaces of said first and second capillary tubes differs by less than about 10%.

67. The method of paragraph 65, wherein said binding steps are effected substantially contemporaneously.

68. The method of paragraph 65, wherein said second capillary tube is the same capillary tube as said first capillary tube, and wherein said binding steps are effected iteratively.

69. The method of paragraph 65 further comprising, prior to said binding steps, the step of size-selecting a nucleic acid to be saturably bound.

70. The method of paragraph 65 further comprising, after said binding steps, the step of using the nucleic acid of either of said first or second capillary tubes in an enzymatic reaction.

71. The method of paragraph 65 wherein the saturably bound nucleic acid of either of said first or second capillary tubes is DNA.

72. The method of paragraph 71 further comprising, after said binding steps, the step of using the DNA of either of said first or second capillary tubes in an enzymatic reaction.

73. The method of paragraph 72 wherein said enzymatic reaction is a DNA sequencing reaction.

74. The method of paragraph 65, wherein either of said first or second capillary tubes comprises glass.

75. The method of paragraph 65, wherein said capillary tubes are present in an array.

76. The method of paragraph 75, wherein said array comprises at least 8 capillary tubes.

77. The method of paragraph 75, wherein said array comprises at least 16 capillary tubes.

78. The method of paragraph 75, wherein said array comprises at least 96 capillary tubes.

79. The method of paragraph 65 wherein said chaotropic agent is selected from the group consisting of: urea, sodium perchlorate, potassium perchlorate, sodium bromide, potassium bromide, sodium iodide, potassium iodide, sodium thiocyanate, potassium thiocyanate, guanidine thiocyanate, sodium isothiocyanate, potassium isothiocyanate, guanidine hydrochloride, guanidine isothiocyanate, lithium chloride, sodium trichloroacetate, dimethylsulfoxide, tetra-amine halides, tetraethylamine chloride, and potassium trichloroacetate.

80. The method of paragraph 65 further comprising the step of removing the solution, wherein said removing step occurs after said contacting step.

81. The method of paragraph 80 further comprising the step of washing the inner surface of either of said first or second capillary tubes, wherein said washing step occurs after said removing step.

82. The method of paragraph 81 further comprising the step of drying the inner surface of either of said first or second capillary tubes, wherein said drying step occurs after said washing step.

83. A method of performing an enzymatic reaction in a capillary tube using a normalized quantity of a nucleic acid, comprising: performing said enzymatic reaction in a capillary tube using a normalized quantity of said nucleic acid, said nucleic acid having been saturably bound from an excess thereof directly on an inner surface of said capillary tube by contacting said inner surface with a solution comprising a nucleic acid and a chaotropic agent for a time sufficient for the nucleic acid to have become saturably bound to said inner surface; and said excess of nucleic acid having been removed therefrom.

84. The method of paragraph 83 further comprising the step of introducing into said capillary tube an enzymatic reaction mixture after said excess of nucleic acid has been removed therefrom.

85. A method of performing an enzymatic reaction in a capillary tube using a normalized quantity of a nucleic acid, comprising: introducing an enzymatic reaction mixture into a capillary tube having a normalized quantity of a nucleic acid, wherein said reaction mixture comprises an oligonucleotide primer, a DNA polymerase, and at least one dideoxynucleotide triphosphate (ddNTP), said nucleic acid having been saturably bound from an excess thereof directly on an inner surface of said capillary tube by contacting said inner surface with a solution comprising nucleic acid and a chaotropic agent for a time sufficient for the nucleic acid to have become saturably bound to said inner surface; and said excess of nucleic acid having been removed therefrom; and performing said enzymatic reaction in said capillary tube using said normalized quantity of nucleic acid.

86. The method of paragraph 85, further comprising subjecting said enzymatic reaction mixture to at least one thermal cycle.

87. The method of paragraph 85, further comprising, after said step of removing said excess of nucleic acid, the step of washing said inner surface of said capillary tube.

88. The method of paragraph 87, further comprising, after said step of washing said inner surface of said capillary tube, the step of drying said inner surface of said capillary tube.

89. The method of paragraph 85, wherein said enzymatic reaction mixture is introduced into said capillary tube by capillary action.

90. The method of paragraph 85, further comprising, after said step of performing said enzymatic reaction, the step of expelling the product of said reaction.

91. The method of paragraph 85, further comprising, after said step of performing said enzymatic reaction, the step of removing unincorporated dideoxynucleotide triphosphates (ddNTPs).

92. The method of paragraph 91, wherein said unincorporated ddNTPs are removed by contacting the product of said reaction with gel filtration media.

93. The method of paragraph 85, further comprising, after said step of performing said enzymatic reaction, the step of inactivating unincorporated dideoxynucleotide triphosphates (ddNTPs).

94. The method of paragraph 93, wherein said unincorporated ddNTPs are inactivated by treating the product of said reaction with calf intestinal alkaline phosphatase (CIAP).

95. The method of paragraph 85, wherein the dideoxynucleotide triphosphates (ddNTPs) included in said enzymatic reaction mixture are selected from among the group consisting of: A only; C only; G only; T only; A,C; A,G; A,T; C,G; C,T; G,T; A,C,G; A,C,T; A,G,T; C,G,T and A,C,G,T.

96. The method of paragraph 85, wherein said dideoxynucleotide triphosphate (ddNTP) is conjugated to a fluorophore.

97. The method of paragraph 96, wherein said fluorophore is base-specific.

98. The method of paragraph 96, wherein said fluorophore is selected from among the group consisting of: fluorescein, 5-carboxy-fluorescein, 6-carboxy-rhodamine, N,N,N',N'-tetramethyl-5-carboxyrhodamine and 5-carboxy-X-rhodamine, rhodamine 110, rhodamine-6-G, tetramethyl rhodamine and rhodamine X.

99. The method of paragraph 96, wherein said fluorophore is an energy-transfer fluorophore.

100. The method of paragraph 85, wherein said primer is complementary to a plurality of contiguous nucleotides in said nucleic acid; and wherein said primer terminates immediately before a nucleotide present in said nucleic acid, the identity of which is desired to be determined.

101. The method of paragraph 100, wherein said primer is conjugated to a fluorophore.

102. The method of paragraph 101, wherein said fluorophore is selected from among the group consisting of: fluorescein, 5-carboxy-fluorescein, 6-carboxy-rhodamine, N,N,N',N'-tetramethyl-5-carboxy-rhodamine and 5-carboxy-X-rhodamine, rhodamine 110, rhodamine-6-G, tetramethyl rhodamine and rhodamine X.

103. The method of paragraph 101, wherein said fluorophore is an energy-transfer fluorophore.

104. The method of paragraph 85, further comprising analyzing a product of said enzymatic reaction to determine the identity of a ddNTP incorporated at the 3'-end of the primer.

105. The method of paragraph 104, wherein said step of analyzing a product of said enzymatic reaction to determine the identity of a base present in said nucleic acid is effected using a technique selected from among the group consisting of gel electrophoresis, capillary electrophoresis, mass spectroscopy, MALDI mass spectroscopy, SELDI mass spectroscopy, fluorescence emission detection, scanning confocal laser-induced fluorescence detection, fluorescence polarization (FP) and analytical microchip analysis.

106. The method of paragraph 104, further comprising inferring the identity of said ddNTP incorporated at the 3'-end of said primer from the emission spectrum of a fluorophore conjugated to said ddNTP.

107. The method of paragraph 106, further comprising inferring the identity of a nucleotide present in said nucleic acid from the identity of said ddNTP incorporated at the 3'-end of said primer.

108. The method of paragraph 107, further comprising inferring, from the identity of said nucleotide in said nucleic acid, the identity of a nucleotide present in a second nucleic acid.

109. The method of paragraph 107, wherein the identity of said nucleotide defines a single nucleotide polymorphism (SNP) in said nucleic acid.

110. The method of paragraph 109, wherein said SNP is a heterozygous SNP.

111. The method of paragraph 109, wherein said SNP is a homozygous SNP.

112. The method of paragraph 109, wherein the identity of said nucleotide is stored as data in a computer data structure.

113. The method of paragraph 112, wherein said computer data structure is embodied in a computer readable medium.

114. The method of paragraph 85, wherein said DNA polymerase is thermostable.

115. The method of paragraph 85, wherein said DNA polymerase is a DNA-dependent DNA polymerase.

116. The method of paragraph 85, wherein said DNA polymerase is an RNA-dependent DNA polymerase.

117. The method of paragraph 85, wherein said nucleic acid is selected from among the group consisting of: DNA, double stranded DNA, single stranded DNA, DNA produced by polymerase chain reaction, DNA produced by reverse transcription reaction, DNA isolated from a eukaryotic cell, DNA isolated from a prokaryotic cell, DNA isolated from an archaea cell, DNA isolated from a fungal cell, DNA isolated from a plant cell, DNA isolated from a virus, DNA isolated from a bacteriophage, genomic DNA, plasmid DNA, episomal DNA, RNA, messenger RNA, double stranded RNA, single stranded RNA, RNA isolated from a eukaryotic cell, RNA isolated from a prokaryotic cell, RNA isolated from an archaea cell, RNA isolated from a fungal cell, RNA isolated from a plant cell, RNA isolated from a virus, genomic RNA, DNA-RNA hybrid, nucleic acid obtained from frozen glycerol stocks of bacteria and nucleic acid obtained from bacterial colonies grown on solid growth media.

118. The method of paragraph 85, wherein said nucleic acid is DNA; and further comprising the step of preparing said DNA by polymerase chain reaction (PCR).

119. The method of paragraph 118, wherein the template used in said polymerase chain reaction is genomic DNA.

120. The method of paragraph 118, further comprising, after said step of preparing said DNA by PCR, the step of removing unincorporated PCR primer using a single stranded Dnase.

121. The method of paragraph 118, further comprising, after said step of preparing said DNA by PCR, the step of removing unincorporated dNTP using a phosphatase.

122. The method of paragraph 118, further comprising, after said step of preparing said DNA by PCR, the step of treating said DNA with Exonuclease I (ExoI) and shrimp alkaline phosphatase (SAP).

123. The method of paragraph 85, further comprising, after said steps of saturably binding said DNA from an excess thereof directly on an inner surface of said capillary tube and removing said excess therefrom, the step of removing unincorporated PCR primer and DNTP by washing said inner surface of said capillary.

124. The method of paragraph 85, wherein said enzymatic reaction is performed in a reaction volume of about 10–5000 nanoliters.

125. The method of paragraph 85, wherein said capillary tube is present in a spatially addressable array of capillary tubes.

126. The method of paragraph 125, wherein said spatially addressable array of capillary tubes is an array having a number of capillaries selected from among the group consisting of: 2, 4, 8, 12, 16, 24, 32, 48, 64, 96, 128, 192, 288, 384, 480, 576, 672, 768, 864, 960 and 1536 capillaries.

127. A product of an enzymatic reaction using a normalized quantity of nucleic acid produced by the method of paragraph 85.

128. A method of obtaining substantially the same quantity of nucleic acid from a first and a second sample for use in an enzymatic reaction effective to detect a single nucleotide polymorphism (SNP), comprising: saturably binding nucleic acid from said first sample directly on an inner surface of a first capillary tube by contacting said inner surface with a first solution comprising a nucleic acid and a chaotropic agent for a time sufficient for the nucleic acid to become saturably bound to said inner surface; and saturably binding nucleic acid from said second sample directly on an inner surface of a second capillary tube by contacting said inner surface with a second solution comprising a nucleic acid and a chaotropic agent for a time sufficient for the nucleic acid to become saturably bound to said inner surface, wherein said inner surfaces of said first and second capillary tubes are capable of saturably binding substantially the same quantity of nucleic acid from each of said first and second samples, respectively; and using the nucleic acid of either or both of said first or second capillary tubes in an enzymatic reaction effective to detect a single nucleotide polymorphism (SNP) present in said nucleic acid.

129. The method of paragraph 128, wherein said enzymatic reaction is selected from among the group consisting of: oligonucleotide ligation assay genotyping (OLA) reaction, minisequencing reaction, TaqMan™ genotyping reaction, Invader™ assay reaction, dye labeled oligonucleotide ligation reaction, pyrosequencing reaction, rolling circle amplification (RCA) reaction and single-base extension (SBE) reaction.

130. The method of paragraph 129, wherein said enzymatic reaction is a single-base extension reaction.

131. The method of paragraph 128, further comprising analyzing a product of said enzymatic reaction.

132. A product of an enzymatic reaction using a normalized quantity of a nucleic acid produced by the method of paragraph 128.

133. A method of performing an enzymatic reaction in a capillary tube using a normalized quantity of a nucleic acid effective to detect a single nucleotide polymorphism (SNP), comprising: performing said enzymatic reaction in a capillary tube using a normalized quantity of said nucleic acid, said nucleic acid having been saturably bound from an excess thereof directly on an inner surface of said capillary tube by contacting said inner surface with a solution comprising a nucleic acid and a chaotropic agent for a time sufficient for the nucleic acid to have become saturably bound to said inner surface; and said excess of nucleic acid having been removed therefrom, wherein said enzymatic reaction is selected from among the group consisting of: oligonucleotide ligation assay genotyping (OLA) reaction, minisequencing reaction, TaqMan™ genotyping reaction, Invader™ assay reaction, dye labeled oligonucleotide ligation reaction, pyrosequencing reaction, rolling circle amplification (RCA) reaction and single-base extension (SBE) reaction.

134. The method of paragraph 133, wherein said enzymatic reaction is a single-base extension reaction.

135. The method of paragraph 133, further comprising analyzing a product of said enzymatic reaction.

136. A product of an enzymatic reaction using a normalized quantity of a nucleic acid produced by the method of paragraph 133.

137. A method of performing an enzymatic reaction in a capillary tube using a normalized quantity of an enzyme, comprising: performing said enzymatic reaction in a capillary tube using a normalized quantity of said enzyme, said enzyme having been saturably bound from an excess thereof directly on an inner surface of said capillary tube by contacting said inner surface with a solution comprising an enzyme for a time sufficient for the enzyme to have become saturably bound to said inner surface; and said excess of enzyme having been removed therefrom.

138. A method of performing an enzymatic reaction in a capillary tube using a normalized quantity of an enzyme, comprising: performing said enzymatic reaction in a capillary tube using a normalized quantity of said enzyme, said enzyme having been specifically and saturably bound from an excess thereof on a modified inner surface of said capillary tube by contacting said modified inner surface with a solution comprising an enzyme for a time sufficient for the enzyme to have become specifically and saturably bound to said modified inner surface; and said excess of enzyme having been removed therefrom.

139. The method of paragraph 138, wherein the modification of said the inner surface of said capillary is effected by silanization.

140. The method of paragraph 138, wherein said modified inner surface of said capillary tube is modified with a functional group.

141. The method of paragraph 140, wherein said functional group is selected from among the group consisting of: an amino group, a pyridyldithio group, a disuccinimidyl suberate group, an oxirane group, a streptavidin molecule and a surface active hydrogel.

142. The method of paragraph 138, wherein said bound enzyme is coupled covalently to said functional group.

143. The method of paragraph 138, wherein said bound enzyme is coupled noncovalently to said functional group.

144. The method of paragraph 138, wherein a plurality of said enzymes is uniformly oriented on said modified inner surface of said capillary.

145. The method of paragraph 138, further comprising the step of releasing said saturably bound enzymes by the addition of an excess of thiopyridone.

146. The method of paragraph 138, wherein said enzyme is selected from among the group consisting of: protease, sequence-specific protease, trypsin, chymotrypsin, proteinase K, papain, pepsin, endoproteinase, endoproteinase Glu-C, endoproteinase Arg-C, endoproteinase Lys-C, endoproteinase Pro-C, endoproteinase Asp-N, V8 protease, glycosidase, β-galactosidase, lipase, oxidase, oxygenase, glucose oxidase, cholesterol oxidase, lactate monooxygenase, ligase, DNA ligase, RNA ligase, methylase, polymerase, DNA-dependent DNA polymerase, terminal transferase enzyme, RNA-dependent DNA polymerase, DNA-dependent RNA polymerase, phosphatase, kinase, DNA gyrase, topoisomerase, nuclease, exonuclease, S1 exonuclease, mung bean nuclease, endonuclease, restriction endonuclease, ribonuclease and urease.

147. The method of paragraph 138, further comprising, prior to said step of performing said enzymatic reaction, the step of filling said capillary with a solution comprising a substrate.

148. The method of paragraph 147, wherein said step of filling said capillary with a solution comprising a substrate is effected by capillary action.

149. The method of paragraph 147, wherein said solution comprises a volume of about 100–2,000 nanoliters.

150. The method of paragraph 138, wherein said enzymatic reaction is effected isothermally.

151. The method of paragraph 138, wherein said capillary is present in a spatially addressable array.

152. The method of paragraph 138, wherein said enzymatic reaction is effected in parallel with at least one additional enzymatic reaction.

153. The method of paragraph 138, further comprising the step, after said step of performing said enzymatic reaction, the step of analyzing a product of said enzymatic reaction.

154. The method of paragraph 153, wherein said step of analyzing a product of said enzymatic reaction is effected using a technique selected from among the group consisting of: mass spectroscopy, capillary electrophoresis, fluorescent scanning and high performance liquid chromatography (HPLC).

155. The method of paragraph 153, further comprising the step, before said step of analyzing a product of said enzymatic reaction, the step of fluorescently labeling said product.

156. A method of performing a protein-based reaction in a capillary tube using a normalized quantity of a protein, comprising: performing said protein-based reaction in a capillary tube using a normalized quantity of said protein, said protein having been saturably bound from an excess thereof on an inner surface of said capillary tube by contacting said inner surface with a solution comprising a protein for a time sufficient for the protein to have become saturably bound to said inner surface; and said excess of protein having been removed therefrom.

157. A method of performing a protein-based reaction in a capillary tube using a normalized quantity of a protein, comprising: performing said protein-based reaction in a capillary tube using a normalized quantity of said protein, said protein having been specifically and saturably bound from an excess thereof on a modified inner surface of said capillary tube by contacting said modified inner surface with a solution comprising a protein for a time sufficient for the protein to have become specifically and saturably bound to said modified inner surface; and said excess of protein having been removed therefrom.

158. The method of paragraph 157, wherein said protein is a noncatalytic protein.

159. The method of paragraph 158, wherein said noncatalytic protein is selected from among the group consisting of: antibody, antigen-binding fragment of an antibody, IgG, IgE, IgM, protein G, protein A and streptavidin.

160. The method of paragraph 157, wherein said protein-based reaction is a molecular binding reaction.

161. The method of paragraph 160, wherein the substrate of said molecular binding reaction is selected from among the group consisting of: protein, enzyme, nucleic acid, DNA, RNA, carbohydrate, lipid, and other chemical.

162. A method of obtaining substantially the same quantity of protein from a first and a second sample, comprising: saturably and specifically binding protein from said first sample directly on a modified inner surface of a first capillary tube by contacting said inner surface with a solution comprising a protein for a time sufficient for the protein to become saturably and specifically bound to said modified inner surface; and saturably and specifically binding protein from said second sample directly on a modified inner surface of a second capillary tube by contacting said inner surface with a solution comprising a protein for a time sufficient for the protein to become saturably and specifically bound to said modified inner surface, wherein said modified inner surfaces of said first and second capillary tubes are capable of saturably and specifically binding substantially the same quantity of protein from each of said first and second samples, respectively.

BRIEF DESCRIPTION OF THE DRAWINGS

The above and other objects and advantages of the present invention will be apparent upon consideration of the following detailed description taken in conjunction with the accompanying drawings, in which like characters refer to like parts throughout, and in which:

FIG. 1 is a schematic of an integrated system for the preparation of cycle sequencing reaction products, which system can advantageously use the methods of the present invention;

FIG. 2 is a flow chart illustrating the steps in production of cycling reactions, the first step of which can advantageously be improved by use of the methods of the present invention;

FIG. 3A is a perspective view of a capillary cassette that is used in a high throughput embodiment of the present invention;

FIG. 3B is a perspective view of the capillary cassette of FIG. 3A inserted into a capillary cassette holder in a system for high throughput application of the methods of the present invention;

FIG. 3C is a flexible capillary cassette that advantageously can use the methods of the present invention;

FIG. 3D illustrates the capillary cassette of FIG. 3C bent to a curved orientation such that the capillary ends are in a curved pattern;

FIG. 3E is a microchip device containing channels, functionally equivalent to capillary tubes, for sample preparation, including the direct reversible immobilization of nucleic acid, according to the present invention;

FIG. 4A illustrates a dispense head for dispensing liquid from the capillary cassette of FIG. 3, for use in the present invention;

FIG. 4B shows an internal cross section of an air displacement dispense head of FIG. 4A;

FIG. 4C shows the dispense head of FIG. 4A with the dispense head closed;

FIG. 5A illustrates a top view of a centrifuge that can be used to dispense fluid from the capillary cassette of FIG. 3A;

FIG. 5B illustrates a cross-section of a rotor arm of FIG. 5A holding a swinging microplate bucket containing a capillary cassette inserted into a microtiter plate;

FIG. 6 shows a schematic of an air-based thermal cycling device with the capillary cassette and holder shown in FIG. 3B inserted into the temperature cycling device, for performing parallel reactions that advantageously can use the template capture and normalization methods of the present invention;

FIG. 7A shows an internal cross section of an air-based thermal cycler with integrated capillary cassette sealing membranes, which can advantageously be used with the template capture methods of the present invention;

FIG. 7B shows a perspective detail of the air-based thermocycler of FIG. 7A, with the lid raised to illustrate the chamber into which the capillary cassette is inserted;

FIG. 7C shows a cross section of the cassette compartment with the capillary cassette inserted into the internal chamber of the thermal cycler of FIG. 7A;

FIG. 8A is a front view of a capillary cassette wash station useful in high throughput performance of the methods of the present invention;

FIG. 8B is a side view of the capillary cassette wash station of FIG. 8A with the wash manifold lowered and the wash tank raised;

FIG. 8C is a further view of the capillary wash station of FIGS. 8A and 8B with the wash manifold raised and the wash tank lowered;

FIG. 8D is an interior cross-section of the wash manifold;

FIG. 8E is a schematic plumbing diagram of the wash station;

FIG. 8F is a top perspective view of the wash tank;

FIG. 9 shows a histogram of the percent success versus read length window for the sequencing analysis of example 1;

FIG. 10 is an electropherogram of the reaction products of example 2;

FIG. 11 shows a histogram of the percent success versus read length window for the sequencing analysis of example 3;

FIG. 12A shows a scanned gel image of electrophoretically separated PCR products prepared at full volume;

FIG. 12B show a scanned gel image of electrophoretically separated PCR products prepared at a nanoscale volume (500 nL);

FIG. 13 is an electropherogram of analysis of sequencing mixtures prepared by performing PCR at 500 nL volumes, a cleanup reaction at full volumes, followed by cycle sequencing reactions performed at 500 nL;

FIG. 14 is a graph comparing signal strength of an isothermal reaction for products prepared in tubes, capillaries, and capillaries using surface binding;

FIG. 26A–FIG. 26D shows the results of full volume SBE reactions and a negative control;

FIG. 27 presents the MegaBACE™ traces of (A) a full volume single base extension reaction; and (B) a nanovolume single base extension reaction, from full volume PCR and ExoI/SAP treatment of the PCR product;

FIG. 28 presents the MegaBACE™ traces of (A) a full volume single base extension reaction; and (B) a nanovolume single base extension reaction, from nanovolume PCR and template capture of the PCR product;

FIG. 30 shows the results of a validation experiment comparing full volume and nanovolume SBE;

DETAILED DESCRIPTION OF THE INVENTION

Figure 15:
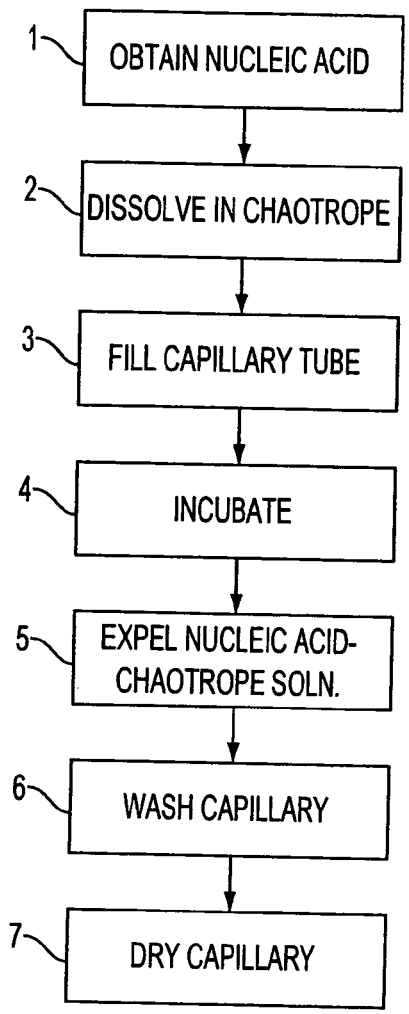
FIG. 15 is a flowchart explaining the methodology for preparing capillary tubes in which nucleic acid is reversibly directly immobilized.

In order that the invention herein described may be fully understood, the following detailed description is set forth.

In the present invention, it was realized that a capillary segment could be used both to meter reagents and as a reaction container for performing temperature cycling reactions. The length of the capillary and the internal diameter (I.D.) of the bore of the capillary tube define the volume of the interior of the capillary tube segment. Capillaries with a 50–150 um I.D. are commonly available. The small internal diameter of the capillary tubes allows creation of a reaction container having an interior volume less than one microliter. With the present invention, capillaries having volumes from 10–500 nanoliters are adaptable to the preparation of DNA cycle sequencing reactions or any other reaction.

The process carried out by the present automated system is shown in the flow chart of FIG. 2. The process begins by the assembly of the reaction mixture, box 52, by combination of reagents and a sample nucleic acid. The combined reagents are then introduced into the capillaries of a capillary cassette, box 54. The ends of the capillaries are next sealed, box 56. The sealed capillary segments are exposed to thermal cycles, box 58, which effect the cycling reaction. The capillaries of the capillary cassette are then dispensed onto a substrate, box 60. The substrate is then transferred to an analytical system for analysis of the reaction mixture, box 62. Details of this process and the structure of the apparatus for carrying out this process are detailed herein.

In reference to FIG. 1, an automated system is shown for assembly of reaction mixtures, temperature cycling to effect the chemical reaction, and dispensing the volume of the completed reaction mixture onto a substrate for subsequent analysis. In the system an automated robot 102 may move the length of stage 114 and may rotate such that automated robot 102 may be moved in relation to other components of the automated system. The automated robot 102 may be rotated to allow the transfer head 104 on automated robot 102 to access objects on all sides adjacent to stage 114. The assembly of a reaction mixture would begin by the transfer head 104 picking up a capillary cassette from cassette hotel 106.

Capillary cassette 15 is shown in FIG. 3A. The capillary cassette is comprised of a number of capillary tubes 12 extending through a substrate 10. It is preferred that the capillary cassette have at least one row of eight capillary tubes and that the capillary tubes have equal spacing. The capillary cassette shown has substrate 10 with 96 capillary tubes arranged in an 8 by 12 array, with spacing of the tubes matching the spacing of the wells of a 96 well microplate. The length of capillary tubes 12 extending from either side of substrate 10 is unequal. It is preferred that the shorter end of capillary tube segments 12 be shorter than the depth of a microplate well. This allows the short end of capillary tubes 12 to be inserted into the wells of a microplate while substrate 10 rests on the top of the microplate.

The capillary tubes may be made of any material compatible with the assay and preparation to be performed, but preferred capillary materials include, but are not limited to, glass and silica capillaries, although plastic, metals and other materials may also be used. Capillary tubes of various dimensions may be used, such as 75 um ID capillary tubes or 150 um I.D./360 um O.D. capillary tubes.

The capillary tubes 12 extend through a substrate 10 and preferably are arranged in a uniform pattern. The capillary tubes are of equal length and extend through the substrate in a substantially parallel orientation such that each of the two opposing ends of the capillary tubes 12 are coplanar and the planes defined by the ends of the capillary tubes 12 are substantially parallel to the substrate 10. The spacing of the capillary tubes may be uniform and selected to match the center-to-center spacing of wells on a microplate. For example on a standard 96 well microplate the capillary tubes would be arranged with a 9 mm center to center spacing, on a 384 well microplate the capillary tubes 12 would be arranged with a 4.5 mm center to center spacing. Higher density capillary formats, compatible with 1536 well microplates or plates with even higher well density, should also be possible. The capillary tubes 12 are preferably secured within the substrate such that the length of capillary tubes 12 extending from one side of the substrate 10 are shorter than the length of the capillary tube on the opposite side of substrate 10. The length of the capillary tubes 12 on the shorter side of the substrate may be matched to the depth of wells in a microplate, such that the length of the shorter side is a shorter length than the depth of a well in a microplate. This feature enables the capillary cassette to be inserted into a microplate such that the substrate 10 rests against the top lip of the multiwell plate and the capillaries on one side of the substrate may extend into the multiwell plate without touching the bottom. For example, in a 96 well microplate the capillary tubes may be disposed on a substrate such that the shorter side of the capillary tube extending from the substrate may be inserted into wells in a microplate without the capillary touching the bottom of the well. This ensures that liquid dispensed into a well is clear of the capillary to prevent re-entering the capillary.

The capillary cassette substrate 10 may be made of a fiberglass board or other rigid or semi-flexible material. The capillary tubes 12 may be inserted through evenly spaced holes in the substrate and secured with adhesive. In one embodiment, the length and width of the substrate are similar to the length and width of a standard 96 well microplate. This simplifies adapting automated systems designed for manipulation of microplates to handle the capillary cassette.

In some embodiments it may be advantageous to coat the interior of the capillary with various surface coatings such as ionic and non-ionic surfactants. Coatings that may be used include bovine serum albumin (BSA), glycerol, polyvinyl alcohol and Tween 20. The coatings are introduced into the capillary and dried onto the interior surface of the capillary tube. Alternatively, covalent modification of the interior surface with silanization or Griganard reaction may be desired. For example, covalent modification of capillary tubes interior surfaces that reduce electroendoosmosis may also be useful in reducing charge surface effects between a capillary interior surface and components of a reaction mixture. U.S. patent application Ser. No. 09/324,892, now U.S. Pat. No. 6,074,542, hereby expressly incorporated by reference for all purposes herein, discloses the use of acryloyldiethanolamine as a covalent capillary coating with advantageous alkaline stability. In addition to this coating, acrylimide or other known coatings may also be used to covalently modify capillary interior surfaces.

A. Assembly of Reaction Mixture

Returning to FIG. 1, the automated system allows for the combination of reaction reagents and sample DNA using the capillary cassette. A capillary cassette would be taken by transfer head 104 from the cassette hotel 106 and brought into contact with the samples contained in a sample plate at location a. The sample plate is dispensed from sample plate hotel 108. The sample would be drawn into the capillary tubes of the capillary cassette by capillary action. The internal volume of the capillary tube is defined by the length of the capillary tube and its internal diameter. The capillary cassette of FIG. 3A acts as a fixed volume parallel pipettor, allowing a number of capillary tubes to be filled in parallel. Each capillary tube segment will meter a discrete amount of liquid that may be subsequently dispensed.

Once one end of each capillary is inserted into the sample containing well, liquid will be drawn into the capillary. This small amount of sample may be combined with other liquids to form a reaction mixture. The sensitivity of analytical instruments such as a capillary array electrophoresis system and the amplification of reaction mixture products enabled by cycling reactions allow for nanoscale reactions and analysis. Very small-scale reaction are able to reliably produce reaction mixture products of sufficient quantity for analysis on a capillary array electrophoresis system, a capillary electrophoresis chip, a mass spectrometer, or other analysis instrumentation. Significantly less reaction reagents are required if a nanoscale reaction mixture is enabled.

The automated system may be used in various ways to prepare reaction mixtures. A few of the many such methods for use of the system in production of reaction mixtures follow.

Reaction Mixture Preparation Example 1: Metering Reagents with Capillary Cassette and Mixing on a Substrate One method to prepare the reaction mixture is to use the pipettor to separately meter the components of a reaction mixture. For example for a PCR mixture, the nucleic acid sample and PCR reagents would be separately metered and dispensed into a single container in which the liquids are combined. In using the automated system of FIG. 1, the automated robot 102 moves transfer head 104 containing a capillary cassette to location a where a sample plate is located. The ends of the capillary tubes of the capillary cassette are dipped into the wells. The capillary tubes fill by capillary action, metering precise amounts of the samples. The wells of sample plate contain the nucleic acid sample to be PCR amplified. The DNA sample should be sufficiently dilute such that 5–20 ng of DNA is contained in the 10–10,000 nL volume metered by each capillary tube segment in the capillary cassette.

FIG. 4A shows a 16 channel capillary cassette transferring fluid samples from a multiwell plate 36 into a capillary cassette 15. The capillary tube segments 12 on capillary cassette 15 are extended into the wells of multiwell plate 36. The wells of multiwell plate 36 are conical and liquid in the well will flow to the bottom central area of each well. This allows a small amount of liquid within the well to be positioned such that a capillary inserted into the center of the well and above the bottom of the well will contact the liquid. The capillary tube segments of the capillary cassette then fill by capillary action with the liquid in the wells. It is preferred that the capillary cassette have. capillary tube segments which have the same center to center spacing as the wells of the multiwell plate containing the DNA samples. In one embodiment the capillary cassette has the same number of capillary tube segments as the number of wells in a multiwell plate holding samples.

Returning to FIG. 1, after the capillary cassette is dipped into the nucleic acid sample containing wells, the filled capillary cassette may be moved by transfer head 104 to a dispensing device location 122. At the dispensing device location 122, the sample is dispensed onto a substrate. A clean capillary cassette is then retrieved and dipped into a sample plate containing the PCR reagents. As seen earlier, the capillary cassette meters a precise amount of liquid defined by the interior volume of the capillary tubes held in the capillary cassette. The metered amount of reaction reagents may be the same volume as the volume of sample dispensed or it may be different, depending on the requirements of the application. At the dispensing device location 122, the reaction reagents are dispensed from each capillary tube segment onto locations on the mixing substrate containing the nucleic acid sample.

The present reaction mixture assembly may be used for assembly of numerous types of reactions. The same basic method used to assemble the PCR reaction mixture may be adapted to assembly of a cycle sequencing mixture, rolling circle amplification reaction mixture, enzymatic assays, chemical reactions, or other reaction mixtures.

When dispensing the contents into a microplate some care must be taken to mix the sample and reaction reagents in a manner which avoids splattering. A number of different methods have been envisioned to dispense liquid from the capillary cassette.

Capillary Cassette Dispensing Example 1: Centrifugal Force

The first method to dispense the contents of the capillary cassette while avoiding splattering uses a centrifuge to dispense the fluid by centrifugal force. The centrifugal force is applied evenly to all of the capillaries in the capillary cassette such that capillaries independently dispense into the microplate wells. The dispensed liquid is drawn by centrifugal force to the bottom of wells in the multiwell plate.

In FIG. 5A, the centrifuge 42 is shown having a swinging microplate bucket 43 that may contain a multiwell plate with an inserted capillary cassette. The swinging microplate buckets are held on rotor 41.

FIG. 5B shows a cross-section of swinging microplate bucket 43. The capillary tubes 12 of the capillary cassette are inserted into wells 36a of multiwell plate 36. The cassette is inserted such that the portions of the capillary tubes 12 extending from the substrate 10 are shorter than the depth of the wells 36a. As shown in FIG. 5B, the capillary tube 12 extending from substrate 10 do not reach the bottom of the wells 36a of multiwell plate 36. Microplate swinging bucket 43 is comprised of an arm 45 and a platform 44. An upper end of arm 45 fits onto latch head 42 on rotor 41. Microplate 36 is positioned on platform 44 of microplate swinging bucket 43. When the centrifuge is in motion, platform 44 rotates on latch head 42 such that the multiwell plate faces the side wall of the centrifuge and the centrifugal force on the liquid in the capillary tubes dispenses the liquid into the bottom of the wells 36a of the multiwell plate 36. When conical shaped wells are used, the centrifugal force will draw the liquids within the well to the well center, causing the sample to locate at a more precise location. The liquid will be displaced from the capillary at fairly low centrifuge speeds.

In FIG. 1, a low speed centrifuge may optionally be included in the automated system at the dispensing device location 122. Automated robot 102 uses transfer head 104 to pick up a microtiter plate dispensed onto location b by microtiter plate hotel 110. Transfer head 104 transfers the microtiter plate to the stage having the low speed centrifuge. A capillary cassette is filled with samples or reaction reagents as described and is transferred onto the microtiter plate on the stage of the low speed centrifuge. The plate and cassette are then spun in the centrifuge, dispensing the liquid from the capillaries into the wells of the microtiter plate. Once the liquid has been dispensed and the centrifuge has stopped rotating, the capillary cassette may by removed by the transfer head and transferred to the cassette washer 118. The transfer head 104 can then pick up a clean capillary cassette from the capillary cassette hotel 106. The clean capillary cassette can be used to meter a second liquid reaction component that is similarly dispensed into the microtiter plate using the centrifuge. In the automated system the centrifuge includes a sensor associated with the rotor used in conjunction with a rotor braking system to stop the rotor in a position that transfer head 104 can access. Such a sensor could be magnetic, optical, mechanical, or use other known means of sensing rotor position.

Capillary Cassette Dispensing Example 2: Air Displacement

A second method of dispensing the liquid contained in the capillary tube segments of a capillary cassette is through the use of an air displacement device. With reference to FIG. 1, a microtiter plate dispensed from microtiter plate hotel is transferred by transfer head 104 to the dispensing device location 122. At this location an air dispenser, such as the one pictured in FIGS. 4A–C is located. Subsequently a capillary cassette is retrieved by transfer head 104, and filled with either sample from a sample multiwell plate or with reaction reagents. The capillary cassette is then moved to the dispensing device location 122 and brought into contact with air displacement head. The substrate of the capillary cassette is placed on a receiving platform on the air displacement head. Alternatively, the air displacement head may be joinable to automated transfer robot 102.

With reference to FIG. 4A, the air displacement head 301 is shown with a capillary cassette 15 held on bottom plate 302. The bottom plate 302 is attached to a manifold assembly by hinge 318. Capillary cassette substrate 10 is held on foam rubber pad 304 that is secured onto bottom plate 302. An array of holes 325 extend through foam rubber pad 304 and bottom plate 302, which are spaced to allow the capillary tubes 12 to extend through foam rubber pad 304 and bottom plate 302 when the capillary cassette is positioned on bottom plate 302. The manifold assembly of the air displacement head is comprised of an upper housing 306, chamber unit 310 and a set of clamps 314. Clamps 314 secure membrane 312 to the lower surface of the chamber unit 310. Membrane 312 forms a seal to the top surface of the capillary cassette 15 when the manifold assembly is closed over the cassette. Membrane 312 has holes 316 corresponding to capillary positions in the cassette when the capillary cassette 15 is placed on bottom plate 302. When the top manifold of air displacement head 301 is closed against bottom plate 302, capillary tubes 12 are positioned extending through capillary tube receiving holes 316 on membrane 312. When the air displacement head 301 is closed it may be secured by latch 322 which mates with hole 324 to clamp the capillary cassette between the foam rubber pad 304 and membrane 312 resulting in a seal between the top surface of cassette 15 and the membrane 312.

FIG. 4B illustrates a cross sectional view of displacement head 301. Upper housing 306 is constructed of metal, acrylic or other rigid material. Gas input coupler 303 is disposed on upper housing 306. When a pressurized gas or vacuum line 305 is attached to gas input coupler 303, a vacuum or pressure force may be introduced into upper chamber 307. Held between upper housing 306 and chamber unit 310 is a gas impervious elastic membrane 308. The area between elastic membrane 308 and upper housing 306 defines upper chamber 307. Secured onto clamps 314 is membrane 312. Membrane 312 is pressed against substrate 10 of a capillary cassette inserted into displacement head 301. Substrate 10 is secured within displacement head 301 by bottom plate 302. Rubber pad 304 provides a deformable surface that exerts uniform force pressing substrate 10 against membrane 312. Membrane 312 has an array of holes 316 that allow the capillaries 12 of the capillary cassette to extend through membrane 312. When a capillary cassette is inserted into air displacement head 301, the substrate seals holes 316 enclosing lower chamber 313. When pressurized gas is introduced into chamber 307 by gas line 305, elastic membrane 308 will be pressed into lower chamber 313. Membrane 308 is located between upper chamber 307 and lower chambers 313. Membrane 308 serves both as seal for the upper end of chambers 313 and the chamber displacement actuator when pressure is applied to the upper chamber 307 through coupler 303. The degree of displacement is dependent on the pressure applied and the elasticity of membrane 308. The resulting air displacement will act to dispense liquid from capillary tubes 12 that extend through the capillary cassette 10 and into the lower chamber 313. By regulating the amount of pressure applied through line 305, a consistent displacement force will be applied to each capillary tube. Given the submicroliter volume of the capillary tube segments, fluctuations in the amount of dispensing pressure should not adversely affect displacement from the tubes.

FIG. 4C illustrates the closed air displacement head 301. Upper housing 306 is pulled toward bottom plate 302 by latch 322 in order to compress membrane 312 against the top of the capillary cassette substrate thereby forming a seal. Clamps 314 secure membrane 312 onto chamber unit 310. Air displacement head 301 is mounted on arm 320. Arm 320 may extend from automated transfer robot 102 shown in FIG. 1 or be positioned at dispense location 122. Pressurized gas may be introduced into upper housing 306 through gas input couple 303.

This displacement head provides an individual displacement chamber for each of the capillaries dispensed. Although a 16 capillary cassette is depicted, the displacement head may be constructed to dispense capillary cassettes having an array of 96 capillaries or greater capillary densities. The dispensing force applied to each capillary is sufficiently small to allow dispensing directly onto a substrate with the sample dispensed at a discrete location.

Air displacement or centrifugal displacement may be used to dispense liquid from the capillary tube segments in a capillary cassette. It may also be possible to dispense liquid from the capillary tubes using a bank of syringe pumps, applying pressure through a gas permeable/liquid impermeable (hydrophobic) membrane, using electrokinetic dispensing, or other known dispensing means. The air displacement head may also be used to dispense finished reaction mixtures onto a substrate for subsequent analysis.

Reaction Mixture Assembly Example 2: Dehydrated Reagents

A second method to assemble the reaction mixture is to have the regents required for the reaction stored as a dehydrated coating either on the interior of a capillary or on a substrate, such as within a well of a multiwell plate. If the reaction reagents were dehydrated onto the interior of capillary tube segments in a capillary cassette, introducing a sample into the capillary would cause rehydration, mixing and formation of the reaction mixture. In a similar manner, if the wells of a microplate were coated with the dehydrated reaction reagents, adding a nucleic acid sample into the wells would bring the reaction reagents into solution, forming an assay mixture. The sample could be metered with a capillary cassette and dispensed from the capillary cassette by one of the methods set out above. The sample would bring the dehydrated reaction reagents into solution and mix with the sample containing nucleic acid by diffusion. This provides a method to assemble the reaction mixture in a very simple manner, potentially without the need to dispense the capillary tubes with a centrifuge or air displacement device. This could both simplify the reaction processing system and shorten the reaction assembly time.

For PCR, a dehydrated reagent mixture is commercially available, sold as Ready-to-Go® (Amersham Pharmacia Biotechnology, Piscataway, N.J.). The stabilized, dehydrated reagents may be coated onto the interior surface of capillary segments or the interior of the wells of a multiwell plate. The Ready-to-Go® product uses a carbohydrate matrix to stabilize the reaction reagents (DNA polymerase, buffer reagents, dNTPs) in a desiccated state. Bringing the reagents in the Ready-to-Go® mixture into solution with the liquid nucleic acid sample and primers in solution produces the final reaction mixture required for the reaction. The combination of the stabilized Ready-to-Go® compounds, the template DNA, primers, and sufficient water produces a final reaction mixture. It is contemplated that reagents for chain termination sequencing reactions and other reactions could also be stored in a desiccated state.

The coating could be applied to surfaces by a number of different methods including vapor phase coating, filling a capillary (by capillary action, pressure filling, etc.) with the Ready-to-Go® mixture and emptying the bulk phase (under vacuum, pressure or other forces), or dipping a substrate (such as a bead) into the reagents and subsequently drying the bead.

Reaction Mixture Assembly Example 3: Solid Phase Capture

A third method of assembly of the reaction mixture is to capture material from the sample on the surface of a substrate, such as the interior of a capillary tube segment. The material captured can be nucleic acid, enzymes, other biopolymers, or chemicals. The desired material from the sample may be attached onto the surface by a number of methods. These include covalent attachment, binding by antibodies, DNA hybridization, hydrophobic interactions, electric field, magnetic field, or other chemical or physical forces. Once the sample has been attached, the remaining liquid in which the sample was suspended may evacuated from the capillary or microchip by chemical reaction or physical force. Air displacement or centrifugal dispensing method may be used to empty the capillary, as can a vacuum. The sample material would remain on the surface of the substrate. In this single step, the sample material may be substantially purified. The reaction reagents may then be combined with the sample material, producing the reaction mixture.

For nucleic acids, one method to immobilize a nucleic acid sample is to attach the nucleic acid directly to a surface. This may be done by non-covalent modification (such as surface treatment with NaSCN, DMSO, etc.) or covalent linkage. There are a number of different covalent attachment methods for DNA known in the art. For example, an amino group can be attached to the deoxyribose base of DNA and incorporated during a synthetic reaction, such as during PCR amplification of a DNA plasmid insert. The glass or silica of a capillary interior could be silanized and the amino group on the modified DNA would covalently bond to the silanized interior of the capillary. Alternatively, other chemistries are available to covalently immobilize DNA onto a surface. Once the DNA is bound to the surface of a capillary or other substrate, the liquid in which the DNA was suspended may be eliminated from the capillary and the capillary may be filled with reaction reagents.

An alternative method of attaching a nucleic acid to the interior of the capillaries of a capillary cassette is through affinity chemistry. One common affinity chemistry procedure labels a biomolecule with biotin and then binds the biotinylated biomolecules to avidin or streptavidin. The avidin/streptavidin may be used to link the biotinylated molecules. Nucleic acid labeled with biotin may be subsequently attached to a surface, such as the interior of a capillary tube. This may be accomplished by binding streptavidin to the interior of the capillary.

One example of the use of affinity chemistry for the binding of DNA to the interior of a capillary is disclosed in U.S. Pat. No. 5,846,727, hereby expressly incorporated herein for all purposes. This reference describes the binding of DNA to the interior surface of the capillary tubes. The technique requires primers labeled with biotin that are combined with dNTPs, a DNA polymerase, and a reaction buffer. This is combined with template DNA, such as plasmids or M13 from a DNA library with sub-cloned DNA inserts, to form the reaction mixture. In the present invention a microplate may contain 96 or more reaction mixtures, each with a unique template with a subcloned DNA sequence. This reaction mixture could be assembled by the method stated in reaction mixture assembly example 1: namely the reaction reagents and the template sample could be separately metered and dispensed into a 384 well microtiter plate. In a microplate well the liquids are combined to form a reaction mixture. The reaction mixture is metered into the capillary tube segments of a capillary cassette. The PCR reaction may be effected by temporarily sealing the ends of the capillary tube segments and exposing the capillary cassette to thermal cycles, as described below. The results of the PCR reaction are exponentially amplified copies of the subcloned plasmid DNA insert containing the biotin labeled primer.

The PCR amplified DNA containing the biotin labeled primer may then be immobilized on the walls of the capillary tubes of a capillary cassette. The immobilization capillary cassette would have capillary tubes with avidin or streptavidin coated onto the interior surface of each capillary tube. The chemistry for attachment of avidin/streptavidin may be that disclosed in, for example, L. Amankwa et al., "On-Line Peptide Mapping by Capillary Zone Electrophoresis," Anal. Chem., vol. 65, pp. 2693–2697 (1993). The capillary is filled with (3-aminopropyl) trimethoxysilane (3-ATPS), incubated for 30 minutes, and air dried. The dried capillaries in the capillary cassette are next filled with sulfosuccinimidyl-6-(biotinamido)hexonate (NHS-LC biotin) which is again incubated followed by air drying. Avidin or streptavidin in phosphate buffer at 7.4 pH is added to each capillary tube. The avidin binds to the biotin immobilized on the interior of each capillary. The double stranded amplified biotinylated PCR products suspended in a buffer (e.g. Tris-HCl, or EDTA with either NaCl or LiCl at 1–3M added for efficaceous binding) are added to the capillary tube and incubated for 5–10 min. This results in a capillary wall modified as follows: capillary wall-Si—$C_3H_6$—NH—CO-biotin-avidin or streptavidin-amplified oligonucleotide with associated biotin primer.

In this embodiment biotin, rather than avidin or streptavidin, is covalently attached first to the capillary wall. This aids in the regeneration of the capillary cassette for subsequent binding reactions. After completing the cycle sequencing reaction, it would be difficult to remove the amplified biotinylated DNA without also denaturing the avidin protein. By having biotin bound to the interior surface of the capillary the amplified DNA may be easily removed by filling the capillary with phenol or formamide solution at 65–90 degrees C. This denatures the avidin protein without removal of the biotin bound to the interior surface of the capillary. This mixture is then dispensed. The capillary cassette may then again be filled with the avidin containing solution and reused for binding subsequent biotinylated amplified template DNA.

Once the DNA is immobilized on the interior surface of the capillary, the contents of the capillary tube may be dispensed in one of the methods described and the DNA would remain bound to the surface of the capillary. This removes debris and other impurities from the DNA presenting a rapid and effective method of DNA purification. The capillary may be rinsed with a buffer for additional purification. The defined area of the interior surface of the capillary provides a known amount of binding sites for the DNA attachment. This provides a simple method for normalization of DNA concentrations. The normalization of DNA concentrations is important in improving the success rate of CAE analysis of cycle sequencing reactions. The capillary cassette may then be dipped into wells or a reagent reservoir containing the reagents for cycle sequencing. The cycle sequencing reaction can be performed by temporarily sealing the ends of the capillary tubes by pressing each end of the capillary tubes against a deformable membrane. The capillary cassette may then be exposed to thermal cycles that effect the cycle sequencing reaction.

Prior to filling, the capillary tube segments of the capillary cassette may be coated with a variety of compounds. Coating the interior surface of the capillary tube segments with bovine serum albumin (BSA) or polyvinyl alcohol has been shown to improve performance of some reactions, such as preparation of chain termination sequencing reactions.

B. Thermal Cycling

Once the reaction mixture is introduced into the capillary tube segments of the capillary cassette, the ends of the capillaries of the capillary cassette are sealed and the capillary cassette is exposed to temperature cycles. The ends of the capillary cassette capillaries are sealed by pressing each of the ends of the capillary tubes against a deformable membrane. Returning to FIG. 1, once the capillary cassette has been filled with the reaction mixture, the ends of the capillaries are sealed and the capillaries are exposed to thermal cycles in thermal cycling device 116.

In one thermal cycling device, shown in FIGS. 7A–7C, the thermal cycling device has integrated membranes that seal the ends of the capillaries and exposes the capillary cassette to thermal cycles. In this apparatus the means for sealing the ends of the capillaries in the capillary cassette is incorporated into the thermal cycling device.

With reference to FIGS. 7A and 7B, the capillary cassette 15 is held on lip 280 within internal passageway 256 between deformable membranes 264a and 264b. As seen in FIG. 7B, deformable membrane 264a is mounted on upper platform 261. Lid 262 is secured on upper platform 261. Platform 261 is attached by pivot 286 to base 265. Pneumatics 284a, 284b are attached at an upper end to upper platform 261 at pivot 263. Screw 282 acts as a stop for upper platform 261 when upper platform 261 is lowered onto housing 270, enclosing internal passageway 256. Diffuser 258 promotes temperature uniformly of air circulating in internal passageway 256. Thermocouple 260 measures temperature of the circulating air. The function of pivot 277 and bottom membrane platform 200 is described in conjunction with FIG. 7C.

FIG. 7C shows a cross section of the capillary cassette holding chamber with capillary cassette 15 inserted into the internal passageway 256. The capillary cassette could be inserted into this area by automated robot 102 of FIG. 1 after the capillary tube segments have been filled with the samples and reaction mixture.

Capillary cassette 15 is positioned such that substrate 10 rests on ledge 280. Capillary cassette is positioned such that the ends of capillary tube segments 12 are depressed against top deformable membrane 264a and bottom deformable membrane 264b when upper platform 261 is lowered over the capillary cassette and lower platform 271 is raised. Lid 262 seals against housing 270 when upper platform 261 is lowered to provide a flush seal. Screw 282 acts as a stop for upper platform 261 to prevent the platform from lowering so far that capillary tube segments are bowed or damaged. Base platform 266 is secured to post 273 and secured to housing 270. The lower end of pneumatics, 284b is secured at a lower pivot 271a to lower platform 271. Extending through lower platform 271 are shoulder screws 268 which extend through housing 270 and stationary platform 266 and are secured to lower platform 200. When upper platform 261 is lowered by pneumatic 284b lower platform 271 is also raised toward housing 270. When pneumatic cylinders 284b, 284a are retracted, the pneumatic cylinders move to a vertical orientation. Upper platform 261 is lowered and lower platform 271 is raised slightly in an arc. Lower platform 271 will arc upward on pivot 277 to move to a position substantially parallel to upper platform 261 when pneumatic cylinder 284b is fully retracted. When a capillary cassette 15 is inserted into internal chamber 258 the ability of platform 200 to "float" on springs 275 prevents excess pressure from damaging capillary tubes 12 or membranes 264a, 264b. Platforms 261 and 200 exert 400 pounds per square inch force on capillary tubes 12 providing sufficient sealing pressure. With upper platform 261 lowered, the capillary tube segments 12 are sealed at each end by deformable membranes 264a, 264b. Deformable membranes 264a, 264b may be made of silicon rubber or other deformable material.

Returning to FIG. 7A, a motor 250 turns shaft 251 that rotates squirrel cage blower 253. Blower 253 produces air movement through diffuser 254 to flow into internal passageway 256. The blower generates sufficient circulation flow that the air flowing through internal passageway 256 circulates at 2,000 feet per minute. Diffuser 254 ensures that the heat of the air blown by blower 253 is uniform throughout passageway 256. Cone 255 on diffuser 254 aids in mixing the flowing air, promoting temperature uniformity through passageway 256. Diffuser 254 acts to ensure an even flow of air through passageway 256 in the region of the capillary cassette and reduces non-uniformity from wall loss effects in internal passageway 256.

The internal passageway 256 is defined by outer housing 270. Outer housing 270 is preferably of rectangular cross section and comprised of sheet metal, plastic or other durable materials. The internal surface of outer housing 270 at all locations except for inlet 278 is lined with thermal foam insulation 272. Insulation 272 prevents excess heating of outer housing 270 and helps retain heat and aids temperature uniformity of the air circulating through internal passageway 256. After flowing through first diffuser 254 the air flows through second diffuser 258. Diffusers 254 and 258 promote uniform air flow and temperature uniformity through internal passageway 256. Past first diffuser 254 internal passageway 256 transitions to match the dimensions of the capillary cassette. The heated air flows past thermocouple 260 that is vertically disposed at the center of internal passageway 256 just beyond second diffuser 258. Thermocouple 260 acts to monitor the temperature within internal passageway 256. Thermocouple 260 may be a temperature-monitoring device inserted into a capillary tube section that extends through outer housing 270 and through foam insulation 272. Alternatively thermocouple 260 may be selected such that it accurately reflects the internal temperature of a capillary tube.

The air circulating through internal passageway 256 passes thermocouple 260 and flows past the capillary tube segments 12 of capillary cassette 15. The ends of the capillary tube segments are sealed at their upper end by deformable membrane 264a mounted on upper platform 261 that has been lowered to form an air tight seal with housing 270. The lower ends of capillary tube segments 12 are sealed by deformable membrane 264b. Deformable membrane 264b is mounted on platform 200 that is secured on a bottom surface by shoulder screws 268. Shoulder screws 268 extend through housing 270 and retained by platform 271. Springs 275 located between platform 200 and platform 271 provide a biasing force while allowing for platform 200 to float such that the deformable membrane 264b is biased against the ends of capillaries 12. The function of double acting pneumatics in sealing lid 262 and applying force to position platform 271 is described in conjunction with FIG. 7C. Lid 262 fits onto housing 270 such that the sheet metal or other material comprising the edge of lid 262 fits on top of housing 270. Membrane 264a is mounted on upper platform 261 preferably such that membrane 264a extends into internal passageway 256 at least far enough that membrane 264a is even with insulation 272. As the air travels past capillary tube segments 12, the length of the capillary tube segments 12 below substrate 10 are rapidly heated and cooled to the temperature of the air rapidly moving through internal passageway 256.

Door 274 controlled by motor 276 is used in conjunction with thermocouple 260 and heating element 252 to control the temperature within internal passageway 256. When door 274 is closed, the air circulating within internal passageway will not be exchanged with outside air. As the air continuously passes over heating element 252 the air is rapidly heated until the air comes to the selected temperature. Once thermocouple 260 senses that the temperature is at a selected temperature, heating element 252 may be kept at a lower heat output such that the internal temperature is maintained. If the temperature needs to be rapidly dropped, as in during a thermal cycling reaction, door 274 may be moved to orientation 274a by motor 276 with the door 274 moved into internal passageway 256, allowing all air which has passed capillary cassette 15 to be exhausted from internal passageway 256 to the outside. It is envisioned that a filter or exhaust duct could be mounted about door 274 to prevent compounds in the circulating air from being exhausted to the environment. The rapidly circulating air will be quickly exhausted to outside of the thermal cycler while ambient air is drawn in through air intake 278. Air drawn into internal passageway 256 through intake 278 flows through heater 252. The area through which the air moves is restricted by block 259 positioned above heater 252 within internal chamber 256. Again the temperature of the air within internal passageway 256 is monitored by thermocouple 260 and when the desired temperature drop has occurred, door 274 will be brought toward housing 270, reducing air volume drawn through air intake 278.

By connecting heating element 252, thermocouple 260 and door motor 276 to an electronic control system, such as a computer controller, this thermal cycler may perform precise air temperature varying sequences. Additional heat is added when needed by heating element 252 and heat is exhausted by opening door 274, with the temperature result of either action monitored by thermocouple 260. Exhausting circulating air through door 274 allows air within internal passageway to drop in temperature at a rate greater than 10 degrees per second.

The rapid temperature change combined with the rapid transfer of heat to or from the capillaries allows for efficient temperature cycling reactions. For example in reactions using a thermostable polymerase, the denaturing of nucleic acid strands and the annealing of primer to template strands each may take place in one to five seconds. The extension of the primer will require less time to effect since the rapidly circulating air and the thin walls of the capillaries rapidly bring the internal volume of the capillaries to the selected temperature. The thin walls of the capillaries and the small capillary volume enable a rapid temperature change and heat transfer throughout the internal capillary volume. This greatly reduces the time required for each cycle of the reaction, allowing more efficient use of the thermal cycler and greater throughput in sample preparation. Presently, a 30 cycle PCR amplification may be performed in under 30 minutes. It should be possible to reduce this time to less than 8 minutes. Once the thermal cycling reaction is complete, upper platform 261 may be raised and capillary cassette 15 removed from internal passageway 256. During the temperature cycling process, the liquid within each capillary tube segment will expand somewhat and some liquid will leak from the capillary and be carried away by the rapidly flowing air. However, such loss is only a few percent of the volume of the capillary tube segment and should not present either a contamination problem or cause enough reaction product loss to materially affect subsequent analysis. To prevent the small opening of capillaries 12 from being contaminated by the small residual of material on deformable membranes 264a and 264b, if desired, disposable materials such as a thin film can be placed over the deformable membranes. The disposable materials can be individual sheets or rolls of material that advance after each use to prevent the capillary openings from touching a section of material previously used. In addition, the portion of capillary tube segments 12 located between substrate 10 and deformable membrane 264a will receive only poor air flow and will be less likely to rapidly reach the denaturation temperature. However since this length is short, the failure of this area to as rapidly reach the denaturation temperature should not adversely affect the ability of the remaining portion of the capillary from producing sufficient reaction product for subsequent analysis.

An alternative device for sealing the ends of the capillary is a capillary cassette holder that seals the ends of capillary tube segments of a capillary cassette. With reference to FIG. 3B the capillary cassette holder is comprised of a pair of parallel deformable membranes 14a, 14b each secured onto platforms 16a, 16b. The deformable membranes may be silicon rubber seals, Teflon®, plastics or other resilient, deformable material. A pair of parallel posts 9 extend from bottom platform 16a to top support platform 24 where the posts are secured by internally threaded nut 18. Post 9 passes through platform 24 and nut 18 is retained on an annular lip of platform 24. Shoulder screws 20 extend through holes in support 24 and are secured to top platform 16b. Springs 22 bias the top platform 16b against the ends of capillary tube segments 12 while allowing 16b to float. The substrate 10 of capillary cassette 15 may be designed to have holes which conform to the spacing and dimension of posts 18 such that capillary cassette 15 may be more easily and securely held within holder 23.

Once the ends of the capillary cassette are sealed in holder 23, the combined capillary cassette and holder may be exposed to thermal cycles. The holder seals 16 capillaries. However, a holder may be designed to hold capillary cassettes having 96 capillaries or higher densities of capillaries. In addition to capillary cassettes, chips of other substrates may be used as the reaction containers. FIG. 3E shows a chip substrate 70 comprised of two bonded substrate layers 72, 74. One layer 72 has grooves 76 extending the length of the chip. The affixed top substrate 72 encloses a capillary dimension passage 76 with opposite open ends. A liquid reaction mixture may be introduced into the enclosed passage. The ends of these passages may be sealed by pressing the ends against a deformable membrane, as was done with the capillary cassettes. Temperature cycling may require longer times because of greater mass material comprising the chip, but cycling times should still be more rapid than conventional cycling.

For isothermal reactions, such as rolling cycle amplification, temperature cycling is not required to effect the reaction. Once an isothermal reaction mixture is combined and introduced into a capillary cassette, incubation of the cassette at a reaction temperature will allow the reaction to occur. With reference to FIG. 1, the automated transfer device may transfer a capillary cassette into incubator 124 where the capillary cassette is incubated at a selected temperature. A set of deformable membranes may be used to seal the ends of the capillaries during incubation. As was seen in other system components, incubator 124 may be used at the same time as other system components.

In the case of PCR or chain termination sequencing reactions it is necessary to expose the reaction mixture to temperature cycles. In FIG. 1 the transfer head 104 moves the capillary cassette into thermocycler 116. The thermocycling device may be any device that can expose the capillary tube segments of the capillary cassette to temperature cycles. Thermal cycling devices that use water, electric field, heating blocks, or other means may be used. Alternatively, air based thermal cycling devices are rapid and adaptable to the low volume cycling of the present invention.

A thermal cycling device that uses air as the temperature transfer medium is shown in FIG. 6. The reaction mixture is contained in capillary tube segments that have a high surface to volume ratio and small material thickness. This allows very rapid transfer of heat through the walls of the capillary and throughout the liquid reaction mixture. An equilibrium temperature is reached rapidly throughout the liquid in the capillary. The use of air as a heat transfer medium enables the rapid ramping of temperature in the reaction chamber. Rapid circulation of the air ensures rapid and more uniform heating or cooling of the capillary segments and their contents.

With reference to FIG. 6, the capillary cassette 15 sealed within holder 8 is inserted through opening 215 in housing 202 of the air based thermal cycler. The holder 8 is supported by housing surface 215 of the thermal cycling chamber 210. The capillary tubes 12 mounted to substrate 10 are exposed to the air of thermal cycling chamber 210 such that the air may freely flow around capillary tube segments 12. Thermocouple 216 monitors the temperature of the air moving past capillary tubes 12.

In the air based thermal cycling device, paddle 208 driven by motor 206 rapidly circulates air within chamber 210. The air is rapidly circulated past the capillaries 12 of capillary cassette 15. Halogen bulb 220 acts as a heat source to heat the air within the thermal cycling chamber 210. To effect a thermal cycling reaction, the circulating air is held at a selected temperature for a selected period of time. The thermocouple 216 transmits the temperature of the capillary tube segment 12 to microprocessor 218. To effect the needed temperature changes the microprocessor instructs actuator 222 to open door 226 allowing air to pass through vent 224. As air passes through vent 224 additional air is drawn into the reaction chamber through air inlet 203 by fan blade 204. Fan blade 204 is driven by motor 206. The venting of hot air and replacement with cooler ambient temperature air, combined with the rapid circulation of air by fan 208, a relatively small thermal cycling chamber 210 and precise measurement of sample temperatures by thermocouple 216 enables rapid temperature ramping. The time required for effecting the thermal cycles is greatly reduced. A typical thermal cycling reaction requires different temperatures for denaturing of nucleic acid strands, annealing of a primer, and extension of a polymerase. The denaturing and annealing steps occur rapidly in a capillary tube where the small internal volume of liquid will rapidly come to equilibrium, while the extension of the DNA molecule takes less than 10 seconds for a 500 base extension. The time required for each thermal cycle of the three temperatures (annealing, extension, denaturing) may be reduced to less than 15 seconds by using the rapid heat transfer of the air based thermal cycling apparatus. A program of 30 cycles, each cycle exposing the capillary to three temperatures for varying amounts of time, theoretically may be effected in less than 8 minutes.

The use of the capillary cassette in combination with an air based thermal cycler allows additional advantages. The capillary cassette holder temporarily seals the capillary, allowing rapid and simplified sealing of each capillary tube segment. The capillary cassette contains a number of capillary tubes in parallel arrangement, allowing for more efficient use of the thermal cycler and allowing greater sample throughput. Once the thermal cycles are completed the capillary cassette 15 contained within holder 8 is removed through opening 215. The capillary cassette 15 is released from the holder and is subsequently dispensed.

The thermal cyclers of FIGS. 6 and 7A–C were illustrated as being used with capillary cassettes. The same devices are adaptable to other containers with opposing ends. For example, a chip-like substrate with a plurality of passageways extending through the chip (as seen in FIG. 3E) has, like a capillary cassette, evenly spaced opposed open ends. Several chips could be placed into a thermal cycler with the open ends temporarily sealed and exposed to thermal cycles. The rapid temperature changes may be a bit slower due to increased material thickness. Other containers with opposing open ends may also be used with either temperature cycling device.

C. Dispensing Completed Reaction Mixture

Following the completion of the thermal cycling or isothermal reactions, the prepared reaction mixture is dispensed into a substrate for analysis by an analytical system. As noted above, the capillary cassette may be dispensed by air displacement, centrifugal force, vacuum or any other displacement method. The substrate into which the reaction mixture is displaced may be the wells of a multiwell plate, locations on a planar substrate, or wells that lead into an analytical chip. The reaction mixture, though small, still may produce enough reaction products that dilution is necessary.

Dispensing Completed Reaction Mixture Example 1: Direct Dilution

In reference to FIG. 1, following completion of the temperature cycling process, the capillary cassette may be removed from air thermal cycler 116 by transfer head 104. The capillary cassette may be moved by transfer head 104 to be placed in a plate dispensed from finished sample hotel 112. The plate, located at position c, may be a multiwell plate such as a 384 well microplate. The wells of the plate contain a dilution liquid, such as formamide, water, TBE, or other selected buffers. The reaction mixture may be dispensed from the capillary tube segments of the capillary cassette by positive displacement, centrifugation, or other dispensing means. The reaction may also be dispensed into a solution for further chemical or biochemical reaction.

Dispensing Completed Reaction Mixture Example 2: Ethanol Precipitation

Ethanol precipitation may be effected in a dispensing means similar to the means of direct dilution. Transfer head 104 of FIG. 1 would again take the capillary cassette from air thermal cycler 116 and place the short ends of the capillaries in a multiwell plate located at position c. In this case the wells of the plate would contain an alcohol, such as 90% ethanol chilled to 4.degree. C. The reaction mixture would be dispensed from the capillary cassette into the ethanol by centrifuge. Air displacement or other dispensing methods can also be used. After allowing time for the precipitation, the multiwell plate can be moved into the centrifuge by transfer head 102 and a low speed centrifugation performed to collect the precipitated nucleic acid in the bottom of the multiwell plate. The alcohol could then be removed by aspiration or other means. The precipitated DNA could then be resuspended in formamide, water or other suitable diluent. Once the sample plate is prepared, by either direct dilution or ethanol precipitation, the plate may be transferred by transfer head 104 to analytical stage 120. Analytical stage 120 may feed the sample plate directly into an analytical device, for example a capillary array electrophoresis system, such as MegaBACE™ produced by Amersham Biosciences, Sunnyvale Calif. Alternatively, the analytical stage could direct the product to other systems for further processing. It is also possible to dispense the samples onto a substrate for mass spectrometry analysis, calorimetric analysis, or other analytical methods.

Dispensing Completed Reaction Mixture Example 3: Dispense Directly into Analytical System In the previous two examples the samples were dispensed into multiwell plates. These plates could then be moved manually or robotically onto a stage for analysis by an analytical system. Alternatively the capillary cassette could be dispensed directly into the wells of an analytical device, such as an electrophoresis chip. For example a capillary cassette having 16 capillaries disposed in the substrate in two parallel rows of eight capillaries may dock with 16 wells in an analytical microchip. Such a microchip would have an array of analytical lanes in fluid communication with a sample port.

The capillary cassette may be designed such that the spacing of the capillaries matches the spacing of the sample reservoir inlets. For example, the capillary cassette illustrated in FIG. 3C includes capillaries 12 extending through flexible strip 11. Flexible strip 11 may be used alone or in combination with other such strips. The orientation of the capillaries in an essentially straight line may be altered by bending strip 11 to form an arc. FIG. 3D illustrates strip 11 bent to allow capillaries 12 to mate with input ports that are disposed on a substrate in a circular pattern. The liquid in capillaries 12 may then be electrokinetically injected or otherwise dispensed from capillaries 12 into ports of an analytical chip if an appropriate electrode array or other dispensing methods are used. Strip 11 may be positioned in the curved orientation by pressing strip 11 against a curved form, such as a curved metal block. This may be done by an automated strip mover incorporated into an automated sample preparation system. The capillary cassette could be dispensed by air displacement or other dispensing means preferably selected to minimize splattering and bubble formation. Prior to dispensing the prepared reaction mixture into the wells for analysis, a small amount of a dilutant could be added to each analytical microchip well. When the capillary cassette is dispensed, the diluent will dilute the samples in the sample wells. The sub-microliter volume reaction mixtures prepared in the capillary cassette, such as a DNA sequencing reaction product mixture, can readily be integrated with the analytical microchip for sequencing or other analysis methods.

D. Washing Capillary Cassettes

Following each use of a capillary cassette, the capillary cassette may be disposed of or it may be washed and reused. After the contents of the capillary cassette have been dispensed or a capillary cassette has otherwise been used, the capillary cassette is taken to cassette washer 118 where the cassette is washed. Following washing, the cassette is returned to the cassette hotel 106 where the cassette may be reused.

With reference to FIG. 8A, capillary cassette washer 410 is comprised of wash manifold 412 and wash tank stage 416. Between wash manifold 412 and wash tank stage 416 is capillary cassette platform 414. Extending from wash tank stage 416 is leg 419. In this wash system, a wash liquid is pumped from one or more of containers 452, 454, 456, 458 through respective tubes 1, 2, 3, 4 into respective router inputs 453, 455, 457, 459. The router directs the selected wash fluid through router outflow 451 through line 451*a* into the wash tank 440. The fluid is drawn from wash tank 440 through capillary tube segments of a capillary cassette. The capillary cassette substrate is held between wash manifold 412 and wash tank 440 such that if suction is applied to wash manifold 412, wash fluid will be drawn through capillary tube segments from wash tank 440. The wash solution is drawn by vacuum through wash manifold 412 and into waste receptacle 490.

FIG. 8E provides a schematic of the working of the wash station. Nitrogen tank 460 provides a pressure source to direct fluid flow. Opening manual valve 462 allows gas to flow through regulator 466 and through filter 468. Regulator 466 regulates the pressure from the pressure source. Pressure sensor 464 monitors gas pressure from the nitrogen source and indicates if gas pressure is below a selected pressure. The pressurized gas flows through filter 468 into line 470. Pressurized gas line 470 branches into the top of sealed wash bottles 471, 472, 473, and 474. The pressurized nitrogen pumps the wash liquid within each wash bottle into respective fluid lines 471*a*, 472*a*, 473*a* and 474*a* respectively through an intake filter 476 on each of said respective fluid lines. Each of the sealed wash solution bottles may contain a different wash solution, such as water, alcohol, a buffer or other wash solution. Although four wash bottles are illustrated, the system is adaptable for use with more or fewer wash fluids. In addition, exchange of wash bottles simply requires venting nitrogen pressure on bottles 471, 472, 473, 474 at valve 462, the removal of the cap from the selected bottle and replacement of the cap with attached pressure and fluid lines into a new or refilled wash fluid bottle. Each of the fluid lines 471*a*, 472*a*, 473*a* and 474*a* terminate in selector valve 478. According to a preset program, the selector valve routes one of the selected fluids from the input line into valve output line 480. The valve output line then transports the pressurized liquid into wash tank 440.

The capillary tubes in the capillary cassette function as a conduit for transport of fluid from the wash tank 440 into the wash manifold interior 425. Vacuum source 496 provides a vacuum force once valve 492 is open. When vacuum valve 498 is open, a vacuum force is directed into waste bottle 490 creating negative pressure within line 490*a*. When valve 495 is open, suction will be applied through suction line 490*a*, suction line 495*a* and suction lines 424*a*. As suction is applied through suction ports 424 by suction lines 424*a* the negative pressure through interior wash manifold 425 will draw liquid up through the capillary tube segments extending into wash manifold interior 425. The liquid will travel through suction passageways 424, into suction lines 424*a*, past valve 495, through suction lines 495*a* and 490*a* and into waste bottle 490.

FIG. 8D illustrates a view of the wash manifold. The bottom of the wash manifold contains holes 426 into which the capillaries are inserted. Wash manifold interior 425 is comprised of lanes joined at a first end to suction passageways 424 and at a second end to purge passageways 423. When suction is applied through line 424*a* fluid will be drawn through capillaries into the lanes comprising interior 425, through passageways 424 and into line 424*a*. When the purge valve is opened, air will pass through line 423*a*, through passageway 423, into interior 425, and into passageway 424, clearing interior 425 of any liquid remaining in interior 425.

Following a wash procedure, wash tank 440 is lowered relative to the capillary cassette platform such that the ends of the capillary tube segments are not in contact with the liquid in wash tank 440. The liquid within wash tank 440 is drained through drain 484 which transmits the fluid into drain line 484*a* when valve 485 is opened and suction is applied through suction line 490*a*. The fluid within wash tank 440 will then drain into waste bottle 490.

Before each wash solution is introduced into wash tank 440, wash fluid supply line 480 and the wash tank distribution manifold 480*a* are purged to empty the line of any previous liquid. This is effected by opening one of the valves in selector valve 478 and flowing wash fluid through supply line 480 and through bleed lines 482. Opening valve 487 allows a vacuum force to be transmitted through line 490*a* through line 488 providing suction which in conjunction with fluid pressure is used to purge the distribution manifold through bleed lines 482. Once wash fluid supply line 480 and distribution manifold are purged, valve 487 is closed and the wash tank is raised and filled. The fill level of wash tank 440 is controlled by the selected wash fluid fill time and wash fluid pressure. Overflow port 486 acts as a safety drain to drain off fluid overfill. If the fluid level within wash tank 440 is too high, liquid will flow from wash tank 440 into overflow port 486 and into line 486*a*. When valve 487 is open, the suction force from line 490*a* and 488 will draw overflow liquid from overflow port 486 into waste bottle 490. Restriction flow valve 441 limits liquid fluid flow through lines 482.

FIG. 8F shows the top perspective of wash fluid tank 440. An input line introduces a wash solution into wash fluid distribution manifold 480*a*. This manifold supplies wash fluid ports 481 that fill tank 440. The spacing of wash fluid ports 481 aids in uniform filling across the width of tank 440. The fill time and fluid pressure regulate the amount of fluid filling tank 440. If excess fluid enters tank 440 it will drain from overflow port 486.

To empty the tank, the tank is lowered by the pneumatics as described, and drain 484 is opened. The shape of tank 440 directs fluid to drain 484 when the end of tank 440 containing drain 484 is lowered. This configuration is designed for efficient filling, emptying and purging of tank 440 and associated fill lines.

Again with reference to FIG. 8E, once a wash cycle has been completed, any liquid remaining within wash manifold interior 425 may be eliminated by opening valve 491 while suction is applied through the manifold. Opening valve 491 causes a pulse of air to be drawn in through vent 493. The air is introduced into wash manifold interior 425 through purge lines 423*a* and is removed by suction lines 424*a*. If the manifold is in contact with capillaries, the relatively narrow bores of the capillaries in the capillary cassette provide a limited capacity for drawing air through the wash manifold. By opening valve 491, a much greater amount of air may be drawn through the manifold through purge lines 423*a* which have a much greater capacity for drawing air. This will result in a sudden rush of air drawn through the manifold. This acts to clear the wash manifold of any liquid remaining within the wash manifold interior 425. Preferably manifold interior 425 is purged before and after raising the wash manifold.

With reference to FIG. 8B, the wash station 410 is shown in side view. The capillary cassette platform 414 is mounted on support legs 445. The reservoir section, shown in internal cross section has at a back lower end of the reservoir, drain outlet 484. Upwardly positioned from the drain outlet at the back wall of the tank is overflow outlet 486. Disposed at the front of the reservoir is reservoir bleed outlet 446. Each outlet is associated with a respective tube and valve, as described in conjunction with FIG. 8E. Each tube carries liquid flowing from an associated outlet when the associated valve is opened and vacuum source applied.

Capillary cassette platform 414 is held in a fixed position by support legs 445. Extending downward from the front of capillary cassette platform 414 is hinge 418 with pivot 432. Attached to a lower end of hinge 418 is wash tank stage 416. Extending from below wash tank stage 416 is leg 419 that is attached at a lower end by pivot 443 to pneumatic cylinder 429. At the back end of the stationary capillary cassette platform 414, the wash manifold is attached at pivot 420. When pneumatic cylinder 429 is extended from the lower end, wash tank stage 416 will be lowered in an arc away from stationary capillary platform. This occurs when no pressure is applied to 429 and gravity causes the wash tank stage to pivot down. When pneumatic cylinder 429 is extended from the upper end by applied pressure, wash manifold 412 will be raised in an arc away from capillary cassette platform 414.

Disposed above capillary cassette platform 414 is wash manifold 412. The wash manifold has a purge passageway 423 disposed at a front end and a suction passageway 424 disposed toward the back end. The respective lines carrying air to the manifold or removing gas or liquids from the manifold are described in conjunction with FIG. 8E.

With reference to FIG. 8C, pneumatic cylinder 429 is shown fully extended from a lower connection pivot 443 on leg 419, through hole 333 in capillary cassette platform 414, to an upper connection at pivot 428 on wash manifold 412. The extended height of the wash manifold is limited by plate 430 that is secured to the top of manifold 412. Plate 430 abuts pin 422 on capillary cassette platform 414 when the wash manifold is raised to a selected level and prevents the wash manifold 412 from being raised beyond this level. When suction is applied to wash manifold interior 425 by applying suction through suction passageway 424, fluid is drawn through capillaries 12 from tank 440.

The front end of capillary cassette platform 414 is joined at pivot 432 to hinge 418 and wash tank stage 416 and the back end of capillary cassette platform 414 is joined at pivot 420 to wash manifold 412. Extending through capillary cassette platform 414 is cutout 434. The dimensions of cutout 434 are such that capillary cassette 15, when placed on capillary cassette platform 414 has associated capillary tube segments 12 extending through capillary cassette platform 414 while the four edges of capillary cassette substrate 10 are retained on the capillary cassette platform 414 on the edge of cutout 434. Alignment pins may be added to capillary cassette platform 414 to properly position the capillary cassette.

To effect the cassette wash sequence, an electronic controller implements a sequence of steps. The electronic controller instructs associated controlled devices of the wash station to carry out a programmed wash sequence. The programmed sequence begins with the capillary cassette being placed on the capillary cassette stage by the robotic transfer device. The wash manifold lowers onto the capillary cassette such that the shorter end of capillary tube segments extend into the wash manifold and the opposite end of the capillary tube segments are within the wash liquid in the wash tank once filled. The substrate provides a partial seal between the wash manifold and cassette such that when suction is applied to the capillary tube segments by the wash manifold, fluid will be drawn up into the wash manifold through the capillary tube segments. The wash solution supply line is purged with the first selected solution to clear the previous solution from the line. As noted in relation to FIG. 8E, the purge solution is removed through distribution manifold to drain 484 and bleed lines 482 to wash waste line 488 and 490a then into waste bottle 490. The wash tank 440 is then raised and filled with the selected wash solution.

A vacuum is applied to the wash manifold causing the solution in the wash tank to be drawn up through all of the capillary tube segments in the capillary cassette. After the programmed wash duration, the wash tank is drained and lowered. The vacuum force is continued through the wash manifold, drawing air through the capillary tube segments. Once the capillary tube segments are dried, the vacuum line of the wash manifold is turned off. The wash solution supply line is purged with the next wash solution and the steps of raising and filling the wash tank, drawing the wash solution through the capillary tube segments and emptying the wash tank are repeated for each selected solution. The specified sequence may repeat these steps for any number of wash solutions. After the final wash has been completed and the tank emptied, air is drawn through the capillaries by applying a vacuum to the wash manifold, drying the capillary tube segments. Periodically the purge valve 491 is opened and air is drawn through vent 493 into purge lines 423a into purge inlets 423. This draws a blast of air through wash manifold interior 425 and clears the wash manifold interior of any remaining liquid, ensuring that any remaining liquid within the wash manifold will not wick back into the capillaries. The manifold vacuum is then shut off and the manifold is raised, removing the manifold from the capillary cassette. The manifold vacuum is again applied and the purge valve 491 is opened and air is drawn through vent 493 into purge line 423a into purge inlet 423. This ensures that any remaining liquid is removed from the wash manifold interior. The vacuum is then shut off. The washed and dried capillary cassette may then be moved by the transfer robot to a capillary cassette hotel or other location.

System Integration

The components of the system could be integrated in a combined system that allows several elements of the complete system of FIG. 1 to operate at the same time. For example, electronic control device 123 may be used to send instructions to the components of the integrated system. The electronic control device may be a computer that sends electronic signals to various system components to effect a programmed set of instructions. Elements of the system could operate simultaneously, increasing system efficiency. For example, automated robot 102 could retrieve a capillary cassette from cassette hotel 106, place the capillary cassette in a sample plate at stage a. An amount of sample from the plate is drawn into the capillary tubes by capillary action. The capillary cassette could then be moved and placed on top of a microtiter plate such that the short ends of the capillary tube segments are in the wells of the microtiter plate. The robot 102 could then transfer the combined microtiter plate/capillary cassette to dispense location 122 for dispensing. The movement of the robot 102, transfer head 104 and dispensing device located at location 122 are controlled by electronic control device 123.

At the same time that a reaction mixture is being assembled, the electronic control device could also be sending electronic signals to thermocycler 116. The vent door, heating element, and thermocouple of thermocycler 116 could be linked to electronic control device 123, allowing electronic control device 123 to effect a selected temperature cycling procedure by regulating the temperature at which air is cycling within the thermal cycler. This precise monitoring allows the temperature cycling procedure to be effected in a minimum amount of time. Once the thermal cycling procedure is complete, the electronic control device 123 could electronically instruct the thermal cycler to shut off the thermocycler fan and heating element and open the lid pneumatically to allow a capillary cassette to be removed from the interior of the thermal cycler.

While automated robot 102 is moving capillary cassettes to assemble a reaction mixture and the thermocycler is operating, the cassette washer 118 could also be cleaning a capillary cassette. Again the electronic control device 123 could instruct the cassette washer 118 to perform a wash sequence in which a capillary cassette is cleaned with a selected sequence of wash liquids and air-dried.

Electronic control device 123 enables each element of the system to be used with maximum efficiency. A single set of instructions to electronic control device 123 could allow assembly of the reaction mixture, thermal cycling of the reaction mixture to effect the desired reaction, dispensing of the completed reaction mixture onto an analytical substrate, movement of the analytical substrate to a stage for processing by an analytical instrument, and cleaning of used capillary cassettes.

Submicroliter Template-Normalized Nucleic Acid Reactions

In a further aspect, the invention provides methods and apparatus for performing nucleic acid reactions in reduced volume, and for normalizing the amount of nucleic acid template present in such reactions.

The present invention is based, in part, upon the novel use of the saturable, yet reversible, binding of nucleic acids by certain materials to control the mass of nucleic acid delivered as template to a subsequent reaction, without a required antecedent determination of the concentration of nucleic acid in the solution from which the nucleic acid is to be captured. In particular embodiments, the internal surface of a capillary is used to effect nucleic acid capture, permitting nucleic acid template to be captured directly in the chamber in which subsequent reaction is to be performed.

Further Advantages of the Present Invention

The present invention is described herein with particular reference to its use for performing DNA sequencing reactions, especially in the context of a high-throughput sample processing system employing capillary electrophoresis, for which the methods and apparatus of the present invention are particularly advantageous. However, it will be clear to the skilled artisan, as will be described in more detail below, that this invention can be used in the course of performing many types of biochemical and chemical reactions using DNA, as well as RNA, as the substrate.

As disclosed in detail below, the present invention provides methods for reversibly immobilizing nucleic acid directly on the inner surface of a reaction chamber, such as a glass capillary tube, or the functional equivalent thereof. After immobilization and other processing steps, the nucleic acid is ready to be used in a chemical, biochemical or enzymatic reaction performed inside the capillary tube. Alternatively, the nucleic acid can be eluted and expelled from the capillary so as to dispense a controlled amount of nucleic acid for subsequent use.

For successful analysis of DNA sequencing reactions using highly sensitive capillary electrophoresis systems, such as the MegaBACE™ system (Amersham Biosciences, Sunnyvale, Calif.), it is important to use consistent, predetermined amounts of template DNA in the reactions, so that the amount of template is neither too low nor too high. By employing capillary tubes with consistent DNA binding capacity, it is possible to "normalize" the amount of template DNA used across all reactions, thereby ensuring that all start with a similar quantity of template. Although normalization can be accomplished in other ways, use of capillary tubes results in dramatic savings of time by reducing the steps necessary to ensure consistency.

Although nucleic acid binding is an inherent property of glass surfaces, it will be appreciated that the capture surface can be modified to alter its binding capacity or binding selectivity. For example, for capturing non-modified DNA, major binding forces are hydrophobic forces, charge-charge (electrostatic) forces, and hydrogen bonding. Thus, to capture non-modified DNA, vinyl groups can be added to the capture surface by reaction in the solution phase, propyl amine groups can be added by CVD, other amines, preferably tertiary amines, can be added by known reactions to maximize the charge-charge interaction. In other alternatives, oligo d(T) can be covalently linked to aminated surface, increasing capture of poly(A) mRNA. A spacer of the general form Cn can be added between the silicon surface and the functional groups. For each of these, the characteristics and/or binding capacity can be altered by changing the concentration of the functional groups.

An additional advantage of the present invention is that it is useful for reducing the number of processing steps associated with, and the quantity of nucleic acid and reagents needed for, carrying out a reaction with nucleic acid, especially in the context of a high-throughput sample processing system. For example, for a DNA sequencing reaction, it is necessary to combine template DNA with a reaction mixture comprising sequencing primer, DNA polymerase, dideoxynucleotides, dNTPs, buffers, salts and water, prior to performing thermal cycling that activates the reaction. Typically, this involves preparing a 20 µl reaction by aliquoting the reaction mixture into a tube, followed by the addition of 200 ng template DNA. The pipet tip used to aliquot the DNA is typically discarded to avoid contamination of the DNA stock. The components are then mixed, thermal cycled and analyzed.

According to an embodiment of the present invention, a capillary tube is filled with a DNA solution, resulting in the reversible immobilization of 5 ng of the template inside the capillary. After several processing steps, the capillary is then filled with 500 nl of reaction mixture, which causes the template to elute from the inside of the tube into the mixture. The capillary is then sealed and thermocycled, with subsequent analysis of the reaction products by a high sensitivity capillary electrophoresis system. Because the capillary serves simultaneously as a pipettor that is filled by capillary action, and as a reaction chamber, it is unnecessary to separately aliquot, with dedicated pipetting systems, either template DNA solution, or the reaction mixture. It is only necessary to provide a stock of each into which the capillary is dipped to fill it. This saves processing steps and materials such as disposable pipettor tips. It also saves reagent that would otherwise be carried over during processing steps, and not introduced into a reaction.

It will also be apparent that a sequencing reaction performed in the capillary can be accomplished in only $\frac{1}{10}$ to $\frac{1}{40}$ of the reaction volume, and therefore $\frac{1}{10}$ to $\frac{1}{40}$ the cost for reagents. Collectively, these advantages result in reduced processing, increased speed, and reduced cost. In the design of high-throughput sample processing systems, capillaries, or functional equivalent thereof, can be arranged in parallel, in ways well known to those skilled in the art, to increase the number of reactions that can be processed simultaneously. The scale of the benefits enjoyed employing the various embodiments of the present invention disclosed herein grow in proportion to the number of samples processed.

Reversible Direct Immobilization of Nucleic Acid in a Reaction Chamber

Figure 16:
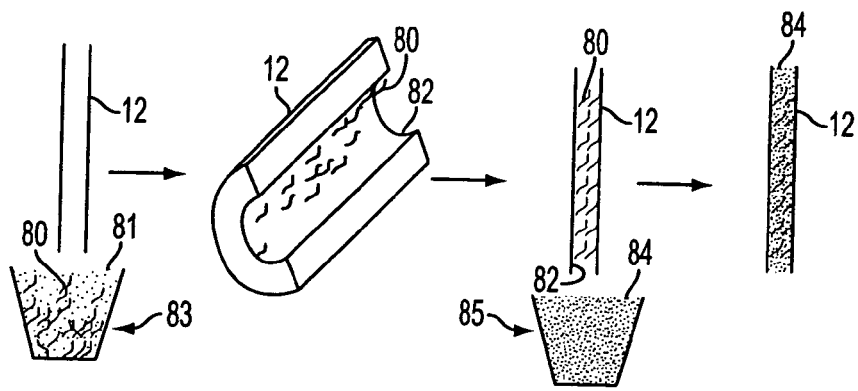
FIG. 16 illustrates an embodiment of the method of the present invention.

FIG. 15 is a flowchart, and FIG. 16 is a schematic that shows the steps associated with embodiments of the instant invention, whereby nucleic acid is reversibly immobilized to the inner surface of a reaction chamber, such as a glass capillary tube. Reaction chambers prepared in this way can then be used to carry out a sequencing reaction with nucleic acid, to effect another type of enzymatic or biochemical reaction with nucleic acid, or for dispensing a predetermined quantity of nucleic acid onto a substrate, such as a microtiter dish well, or into an analysis instrument, such as a capillary electropheresis device.

With reference to FIG. 15, and FIG. 16, in step 1 the nucleic acid sample is prepared from a suitable source, after which, in step 2, the nucleic acid 80 is dissolved in a solution 81 containing chaotropic ions. In step 3, the reaction chamber is filled with the nucleic acid-chaotrope solution and incubated, in step 4, for sufficient time to allow reversible binding of the nucleic acid 80 to the inner surfaces 82 of the reaction chamber 12. In step 5, the nucleic acid-chaotrope solution is removed, followed by washing, step 6, and drying, step 7, of the reaction chamber. At this point the reaction chamber is useable. Part 12 refers to a capillary tube, or more broadly, a reaction chamber, including capillary tubes and structures equivalent in function thereto. Part 80 refers to DNA, or more broadly, nucleic acid, including DNA and RNA and derivatives thereof.

The process begins by obtaining nucleic acid, FIG. 15, step 1, from a suitable source. The nucleic acid may be deoxyribonucleic acid (DNA), ribonucleic acid (RNA) or derivatized forms of these molecules. Nucleic acids can be isolated and purified according to methods well known in the art (see Current Protocols in Molecular Biology, John Wiley & Sons, Inc., 2000, Edited by Fred M. Ausubel et al., ISBN 0-471-50338-X) from a variety of living organisms or self-replicating systems that rely on living cells. Cells can be eukaryotic cells, including human and non-human mammalian cells, non-mammalian animal cells, plant cells and fungal cells. Additionally, eukaryotic cells can be free living single celled organisms, such as amoebae or other parasites. Cells can also be prokaryotic cells including bacteria and archaebacteria. Nucleic acids can also be obtained from viruses, including RNA and DNA viruses, and viruses that infect animal cells, plant cells, fungal cells, and bacterial cells. Nucleic acids can also be produced according to chemical synthetic methods well known in the art.

After obtaining template nucleic acid from the appropriate source, the nucleic acid, FIG. 16 80, is resuspended and/or dissolved into a solution containing a chaotropic agent, FIG. 15, step 2, and FIG. 16 82. The chaotropic agent is desirably at sufficiently high concentration (e.g., about 0.5 M to 8.0 M) to effect the reversible binding of the nucleic acid, but not so high as to cause the nucleic acid, or the chaotrope itself to precipitate out of the solution under all of the conditions to which the solution is subjected in carrying out the invention.

A chaotropic agent is a substance that affects the partitioning of molecules from a nonaqueous to an aqueous phase due to the disruptive effect that the substance has on the local structure of water. Chaotropic agents are salts of chaotropic ions, and are highly soluble in aqueous solutions. At sufficiently high concentration in aqueous solutions the chaotropic ions provided by such salts cause nucleic acids to lose secondary or tertiary structure, and double-stranded nucleic acids to melt (i.e., strand-separate). It is hypothesized that chaotropic ions have these effects by disrupting hydrogen-bond networks existing in water, causing the denatured form of the nucleic acids to be more thermodynamically stable as compared to the structure of more highly ordered structures (e.g. the double helix) that exist in a typical aqueous environment.

As described previously by Vogelstein et al., Proc. Natl. Acad. Sci. USA 76, 615–619 (1979) and by Chen and Thomas, Anal. Biochem. 101, 339–341 (1980), in the presence of a sufficiently high concentration of chaotropic ions (e.g. about 0.5 M to about 8.0 M), nucleic acids will reversibly bind certain substances, such as silica. The mechanism of nucleic acid binding to silica may involve chaotropic ion disruption of the water structure at the surface of the negatively charged silica, allowing a cation (e.g. Na+ or K+) mediated salt bridge to form between it and the negatively charged phosphate backbone of the nucleic acid strand. To effect nucleic acid silica binding, a chaotropic agent may be used singly or as a mixture of two or more chaotropes. The salt bridge is not a permanent bond and can be disrupted when the ionic concentration in the proximity of the bond is lowered. In this way, nucleic acid can be eluted from silica or similar material with water or other suitable low ionic strength aqueous buffer.

Chaotropic ions include guanidinium, iodide, perchlorate and trichloroacetate. Chaotropic salts include sodium perchlorate, potassium perchlorate, sodium bromide, potassium bromide, sodium iodide, potassium iodide, sodium thiocyanate, potassium thiocyanate, guanidine thiocyanate, sodium isothiocyanate, potassium isothiocyanate, guanidine hydrochloride, guanidine isothiocyanate, lithium chloride, sodium trichloroacetate, and potassium trichloroacetate. Other substances with chaotropic properties include dimethylsulfoxide (DMSO), urea, and the tetra-amine halides, including tetraethylamine chloride.

After dissolving the nucleic acid in the solution of the chaotrope, the nucleic acid-chaotrope solution, FIG. 16 83, is introduced into a reaction chamber, FIG. 15, step 3, and FIG. 16 12.

For the purpose of reducing the cost of reagents used to effect the sequencing reaction, the reaction chamber will typically be of very small volume, desirably from about 1–1000 nanoliters (nl), more desirably from about 10–500 nl, most desirably from about 100–500 nl.

In most circumstances, the reaction chamber is configured so that solutions can be introduced into it passively, by taking advantage of capillary action. Capillary action is the phenomenon by which the elevation of a liquid rises where it is in contact with a solid, such as the sides of a tube, and is most marked in capillary tubes, i.e., tubes of very small diameter. Capillary action depends on the forces created by surface tension and by wetting of the sides of the tube. If the forces of adhesion of the liquid to the solid (wetting) exceed the forces of cohesion within the liquid (surface tension), the liquid will rise up the tube, i.e., it will rise above the hydrostatic level. Alternatively, the solution can be introduced into the reaction chamber actively, such as by pumping using positive or negative atmospheric pressure.

It is simplest and most economical to take advantage of capillary action to fill the reaction chamber with the nucleic acid-chaotrope solution, in which case a capillary tube serves as the reaction chamber. If the bore of the capillary is of known and uniform areal cross section, then the volume of the tube is easily calculated, being linearly proportional to its length. Thus, a capillary tube reaction chamber of given total volume is obtainable by cutting the tubing to the desired length given by the calculation. In accordance with the laws of fluid dynamics however, care must be taken that the density of the solution is not so great, its surface tension so low, and the diameter of the tubing insufficiently small, that the column of solution cannot overcome gravity, and thereby fails to fill the tube.

During filling, one end of the tube is dipped into the nucleic acid-chaotrope solution, FIG. 16 83, that is usually provided in volume excess over the total volume of any tube to be filled. In this manner, the tube is filled in one step, reducing the chance of bubble formation at the inlet. The opposite end of the capillary must be open, or otherwise able to allow air to escape from the filling tube.

It is not obligatory that the outside of the reaction chamber approximate the form of a tall thin cylinder, as it does with a capillary tube. Rather, as will be apparent to the skilled artisan, the functional equivalent of a capillary tube can be manufactured in a variety of ways. Throughout the specification, the term capillary tube should be understood to represent not only that structure commonly referred to as a capillary tube, but also any structure that is functionally equivalent thereto. For example, a tunnel, channel or groove can be formed that is configured so that fluid can fill it by capillary action, or by the direct application of some force, e.g. positive or negative pressure, or centrifugal force. The tunnel, channel or groove can be formed mechanically, chemically, thermally, or by other means known to the skilled artisan. A channel or tunnel can be formed by removing material from a matrix, e.g., using a drill bit, laser, or chemical etching As illustrated in FIG. 3E, a groove or channel 78 in the surface of a substrate 72, such as a glass slide of any shape and dimension, can be cut with a saw, or formed by laser ablation or chemical etching to create a structure called a chip or microchip 70. For example, grooves in a silicon wafer can be formed by photolithographic methodologies known in the art, and grooves in glass slides can be etched using hydrofluoric acid.

If a groove or similar depression 78 is formed in the surface of a substrate 72, it will usually be advantageous to cover it with a cover 74 to form an enclosed space. Covering the groove or depression 78 ensures that there is maximal surface area for the fluid to interact with, thereby promoting the capillary action, minimizes the opportunity for contaminants to contact the reactants, and creates a vapor barrier to ensure that during any elevation in temperature of the reaction, such as during thermal cycling, the tendency of the reaction to vaporize is minimized.

Covers 74, which can be comprised of material identical to, or different from, that of the substrate 72 in which the groove is cut, can be applied using a variety of means known in the art. For example, the cover 74 can be glued to the substrate using an epoxy, cyanoacrylate or other type of glue. The cover can be welded by melting it and underlying material until they fuse, through the application of heat or light. The cover 74 can also be fixed in place mechanically, such as with a clamp, or even magnetically.

The material of which the reaction chamber is comprised is advantageously a material to which template DNA, or other nucleic acid, reversibly and saturably binds in the presence of a sufficiently high concentration of chaotropic ions. Frequently, the reaction chamber is comprised of glass, especially when configured as capillary tubing. High quality glass capillary tubing is readily available in a range of interior dimensions from a variety of manufacturers, including Polymicro Technologies (Phoenix, Ariz., USA).

If comprised of a fragile, hydrophilic material like glass, it may be advantageous to coat the outside of the capillary tubing with a polymer material, such as a polyimide. A polyimide coating provides a protective layer that protects the capillary tubing from abrasions and breaking by bending. Polyimide also creates a hydrophobic layer on the outer surface of the capillary which can help prevent the adherence of aqueous reaction mixtures when the capillary is filled by dipping it into a reaction mix; this helps prevent wastage of reagents. Other potential coatings are acrylates, silicones, fluoropolymers, and aluminum.

Many types of glass may be used including alkali-borosilicate glass, alumina-silicate glass, barium flint glass, barium-borate glass, borosilicate glass, borate glass comprising B2O3, germinate glass comprising GeO2, chalcogenide glass, silicate glass comprising SiO2, silica glass, fused silica glass, synthetic fused silica glass, quartz (crystalline SiO2), fused quartz (amorphous SiO2), doped synthetic fused silica (doped with trace elements such as germanium, fluorine, boron, phosphorous, and titanium), lanthanum glass, optical glass, phosphate glass, and soda-lime glass.

Alternatively, the reaction chamber can be comprised of a metal or metalloid, materials that, like glass, can be fashioned into capillaries or wafers. Suitable pure and alloyed metals include magnesium, aluminum, titanium, vanadium, chromium, manganese, iron, cobalt, nickel, copper, zinc, gallium, zirconium, niobium, molybdenum, palladium, gold, silver, cobalt, niobium, indium, rhodium, tin, steel, stainless steel, and bronze. Suitable pure and alloyed metalloids include silicon, germanium, arsenic, and gallium arsenide.

The reaction chamber can also be comprised of carbon in its multiple allotropes, including graphite, diamond, C60 and related allotropes comprising, for example, nanotubes, or comprised of organic compounds such as plastic. For these materials, it may be necessary to derivatize the carbon or plastic in such a fashion as will support the reversible binding of nucleic acid to the plastic in the presence of chaotropic ions.

After the reaction chamber, such as glass capillary, FIG. 16 12, has been filled with nucleic acid-chaotrope solution 83, the solution is incubated for such time and under such conditions that at least a portion of the DNA in the solution reversibly binds to the inner surface, FIG. 16 82, of the chamber or tube, FIG. 15, step 4. In other embodiments, irreversible binding can be effected.

Without wishing to be bound with theory, it is believed, as discussed above, that if the inner surface is glass containing SiO2 (silica), in the presence of a sufficiently high concentration of chaotropic ions the nucleic acid most likely forms salt-bridge type bonds with the silica via the phosphate backbone. Usually, binding is allowed to proceed at about room temperature (about 24° C.), but other temperatures may be chosen as is deemed appropriate, so long as the effectiveness of binding is not significantly hampered, and so long as neither the DNA nor chaotrope precipitates from the solution.

After the nucleic acid in the nucleic acid-chaotrope solution has had the opportunity to bind to the inner surface 82 of the reaction chamber or tubing, the solution containing unbound DNA and the chaotrope is then removed 5, the inner surface is washed 6 with washing solution, and then remaining traces of liquid from the wash solution is removed by drying 7.

The greater proportion of nucleic acid-chaotrope solution is removed from the chamber by a variety of means including application of positive or negative air pressure, or by centrifugation to expel the solution.

Washing is performed to purify the bound nucleic acid by removing excess, unbound nucleic acid, chaotropic agent, and any impurities that may have contaminated the nucleic acid. It is important to remove the chaotropic agent because these ions can severely interfere with most subsequent chemical and biochemical reactions, even at very low concentrations. Washing can be performed in a variety of ways. For example, a capillary tube can be filled by capillary action, after which the washing solution is expelled in similar manner by which the nucleic acid-chaotrope solution was removed. Alternatively, a reaction chamber can be filled and emptied by pumping of the wash solution. Sufficient volume of washing solution is used to essentially eliminate the presence of all contaminants. After washing, the wash solution is removed from the chamber or tube.

The composition of the washing solution is chosen so that it does not remove by elution any substantial portion of the nucleic acid that has become bound to the inner surface of the chamber or tubing, and is typically a solution of an alcohol with pure water. Suitable alcohols include the lower molecular mass alcohols methanol, ethanol and isopropanol. The concentration of alcohol is high enough that elution of nucleic acid minimized, and is preferably at least 50%, more preferably at least 60%, and most preferably at least 70% volume by volume. Typically, ethanol is used at concentration greater than about 70%–80% volume by volume.

The washing solution can also comprise a salt, preferably in the form of a buffer, such as an acetate buffer, or a tris-EDTA buffer (containing, e.g., 10 mM Tris-HCl and 1 mM ethylenediamine-tetraacetic acid (EDTA), pH 8.0). The salt can have the effect of buffering pH so that the pH is in the range of about 6.5–8.5, and also stabilizing the binding interaction between DNA and the inner surface of the chamber or tube during washing.

It is frequently desirable to remove essentially all traces of the liquid from any small volume of the wash solution remaining in the chamber or capillary tubing by drying. Although low concentrations of some components of the liquid, such as ethanol, tend not to significantly interfere with subsequent biochemical reactions, higher concentrations can interfere. Drying can be effected by subjecting the chamber or tube to a high enough vacuum so that the liquid vaporizes and is carried away. Alternatively, a dry gas, such as air, nitrogen or argon, can be forced at pressure through the chamber or tube to promote the evaporation of the liquid. The drying gas can be warmed to further promote evaporation.

After drying, the reaction chamber, now bearing reversibly immobilized nucleic acid, can be used immediately to perform a biochemical reaction with the nucleic acid, or stored, under appropriate conditions, for future use. Reaction chambers prepared according to the steps discussed above can be advantageously used to normalize the amount of a nucleic acid to be used in parallel reactions, dispense predetermined amounts of DNA or RNA onto a substrate, and to perform nanoscale DNA sequencing reactions, as well as many other types of reactions with DNA and RNA. However, as will be clear to the skilled artisan, these particular applications should not be seen as limiting the scope of uses to which such reaction chambers can be put.

Use of the Present Invention in an Automated System

Reaction chambers in the form of capillary tubes can be processed as illustrated in FIG. 15 and used singly, but it will frequently be advantageous to combine multiple capillary tubes in parallel fashion, so as to be able to increase sample throughput, particularly in an automated system. For this purpose, capillary tubes can be conveniently organized into a capillary cassette; the greater the density of capillary tubes per cassette, the greater the potential sample throughput. An apparatus, such as that described in U.S. application Ser. No. 09/577,199, now U.S. Pat. No. 6,423,536, can be used to automate the processing steps illustrated in FIG. 1, as well as any subsequent steps associated with carrying out reactions with the immobilized nucleic acid, including capillary filling, emptying, washing, drying, and or thermal cycling. Used in this way, the cassette becomes an automated, fixed-volume parallel pipettor, allowing all the capillary tubes to be filled simultaneously from the wells of a sample plate by capillary action.

Capillary cassette 15 is shown in FIG. 3A. The capillary cassette is comprised of a number of capillary tubes extending through a substrate 10. It is preferred that the capillary cassette have at least one row of eight capillary tubes and that the capillary tubes have equal spacing. The capillary cassette shown has substrate 10 with 96 capillary tubes arranged in an 8 by 12 array, with spacing of the tubes matching the spacing of the wells of a 96 well microplate.

The capillary tubes 12 extend through a substrate 10 and preferably are arranged in a uniform pattern. The capillary tubes are of equal length and extend through the substrate in a substantially parallel orientation such that each of the two opposing ends of the capillary tubes 12 are coplanar and the planes defined by the ends of the capillary tubes 12 are substantially parallel to the substrate 10. The spacing of the capillary tubes may be uniform and selected to match the center-to-center spacing of wells on a microplate. For example on a standard 96 well microplate the capillary tubes would be arranged with a 9 mm center to center spacing, on a 384 well microplate the capillary tubes 12 would be arranged with a 4.5 mm center to center spacing. Higher density capillary formats, compatible with 1536 well microplates or plates with even higher well density, should also be possible. The capillary tubes 12 are preferably secured within the substrate such that the length of capillary tubes 12 extending from one side of the substrate 10 are shorter than the length of the capillary tube on the opposite side of substrate 10. The length of the capillary tubes 12 on the shorter side of the substrate may be matched to the depth of wells in a microplate, such that the length of the shorter side is a shorter length than the depth of a well in a microplate. This feature enables the capillary cassette to be inserted into a microplate such that the substrate 10 rests against the top lip of the multiwell plate and the capillaries on one side of the substrate may extend into the multiwell plate without touching the bottom. For example, in a 96 well microplate the capillary tubes may be disposed on a substrate such that the shorter side of the capillary tube extending from the substrate may be inserted into wells in a microplate without the capillary touching the bottom of the well. This ensures that liquid dispensed into a well is clear of the capillary to prevent re-entering the capillary.

The capillary cassette substrate 10 may be made of a fiberglass board or other rigid or semi-flexible material. The capillary tubes 12 may be inserted through evenly spaced holes in the substrate and secured with adhesive. In one embodiment, the length and width of the substrate are similar to the length and width of a standard 96 well microplate. This simplifies adapting automated systems designed for manipulation of microplates to handle the capillary cassette.

Accurate Control and Normalization of the Quantity of Nucleic Acid to be Used in a Biochemical Reaction When undertaking to carry out a biochemical reaction with nucleic acid, it is often crucial to the success of the reaction that the amount of input nucleic acid be known with precision. This allows the experimenter to properly calculate the appropriate ratio of other reaction components, such as enzymes. For example, as discussed in the Background section, if too much template DNA is used in a sequencing reaction to be analyzed with a capillary electrophoresis system, poor quality sequencing data often results. Nucleic acid concentration in a stock sample is relatively easily determined by measuring light absorption at 260 nm, or measuring the amount of dye binding relative to standard curves. However, both these approaches use up a portion of the sample and neither approach is easy to implement in the context of a high-throughput sample processing system. Fortunately, the present invention is useful for precisely controlling the amount of nucleic acid to be used for a variety of applications.

If during the binding reaction occurring in the reaction chamber, the nucleic acid-chaotrope solution is allowed to stay in contact with the inner surface of the chamber or tube for sufficient time, and if the nucleic acid is at high enough concentration in the solution, it is possible to saturate the available binding sites on the inner surface of the chamber or capillary with nucleic acid. This is known as saturable binding. As long as the amount of nucleic acid in solution prior to incubation exceeds the binding capacity of the inner surface of the chamber, a fixed, maximal quantity of nucleic acid will be immobilized, regardless of the amount of nucleic acid initially in the solution. In this way, if the concentration of nucleic acid in solution exceeds a minimum, it is not necessary to know the actual concentration; the amount of nucleic acid bound will be determined solely by the binding capacity of the reaction chamber. Accordingly, if the nucleic acid in a capillary tube that was saturably bound is eluted into a known volume of liquid, the concentration and amount of nucleic acid in the liquid is knowable with a high degree of accuracy.

Thus, it is possible to use the present invention to obtain, or measure out, accurately known, small, consistent quantities of nucleic acid, based on the binding capacity of capillary tubes or other configurations of reaction chamber. For example, if it is desirable to carry out a reaction using 10 ng of nucleic acid, it is only necessary to obtain a capillary tube, or other reaction chamber, with a total of 10 ng of nucleic acid binding capacity. Then, the capillary is filled with nucleic acid-chaotrope solution wherein both the nucleic acid and chaotrope are at sufficiently high concentration to support saturable binding in reasonable time. After the incubation, emptying, washing and drying steps are complete, the experimenter is confident that the capillary contains 10 ng of nucleic acid which can be eluted for dispensing, or left to reside in the capillary for future use.

Typically, the binding capacity, or amount of nucleic acid that can be saturably bound to the inner surface, is determined empirically. For example, a known amount of test nucleic acid is labeled with a radionuclide, such as $^{35}S$, $^{33}P$ or $^{32}P$, according to methods known in the art. After labeling, the specific activity of the labeled nucleic acid is determined to establish a ratio of disintegrations per minute per mass unit, or concentration unit of nucleic acid. The labeled nucleic acid is then dissolved in a solution containing chaotropic ions at a predetermined concentration. A standard reaction chamber, representative of a general supply, is then tested. For example, a predetermined length of glass capillary tubing is cut and filled with the labeled nucleic acid-chaotrope solution. After sufficient time for saturable binding to occur, the capillary is emptied and washed. Then, the amount of radioactivity retained inside the tube is measured, and, with knowledge of the specific activity of labeling, converted to an amount of nucleic acid. This factor can then be used to calculate the amount of nucleic acid that will be retained in any length of capillary tubing cut from the same lot, so long as similar conditions for binding are used in any subsequent experiment.

An advantage of using the present invention to accurately obtain a predetermined quantity of nucleic acid is to normalize quantities of nucleic acid for subsequent use. This advantage is especially significant if it is necessary to process many samples. For example, in the current state of the art, it is not practical, when preparing different template DNAs for sequencing, to ensure that the concentration of the templates is the same. Thus, according to prior methods it was necessary to normalize the different template DNA samples, by separately determining the DNA concentration in each prep, and diluting the DNA to the proper concentration for each and every sample. This is especially important for capillary electrophoresis because of the sensitivity of that technology to overloading of the capillaries with template DNA. The requirement for normalization of the template DNA added significant time and cost to obtaining high quality DNA sequence data using this system, or required that researchers accept increased failure rates.

However, the present invention allows very rapid normalization to minimize differences in starting template concentration. To normalize the different templates to a predetermined concentration it is only necessary to provide functionally equivalent capillary tubes (one for each template) with a known, saturable DNA binding capacity, and template DNA-chaotrope solution with sufficiently high concentration of both DNA and ions that all the DNA binding sites in the capillary become occupied within a reasonable period of time. After emptying and washing, all the capillaries will contain about the same quantity of template DNA, and are thus normalized.

As will be apparent to the skilled artisan, if it is not desirable to saturate all the possible nucleic acid binding sites inside a reaction chamber, it is possible to control the amount of nucleic acid that is reversibly bound. This is possible because the kinetics of the binding reaction depend on a number of variables, including nucleic acid concentration, average nucleic acid molecular size, solution pH, chaotropic ion concentration, the number of available binding sites on the inner surface of the reaction chamber and temperature. Thus, with empirical analysis, it is possible for the skilled artisan to establish binding conditions that result in the consistent, predictable, reversible binding of a predetermined quantity of nucleic acid that does not saturate all available nucleic acid binding sites inside a reaction chamber.

DNA Sequencing for Capillary Electrophoresis

The advantages of the present invention are beneficially applied to carrying out DNA sequencing reactions, particularly for analysis with highly sensitive capillary electrophoresis systems such as MegaBACE™. To use the present invention for DNA sequencing, template DNA must be immobilized in capillary tubes, or the functional equivalent thereof. Template DNA is that DNA for which the sequence of constituent bases is to be determined. Template DNA can be single stranded, or double stranded, wherein two complementary DNA strands are hybridized together, and knowledge of the sequence of one strand can be used to infer the sequence of bases in the other strand according to the rules of Watson-Crick base pair complementarity.

Template DNA is typically obtained directly from self-replicating genetic systems, grown in a host, into which the DNA fragment to be sequenced was cloned. Alternatively, the template can be obtained from any source, e.g., genomic DNA, by amplifying a particular DNA sequence using the polymerase chain reaction, or a functionally equivalent linear or exponential amplification process.

Self-replicating genetic systems include episomal elements, such as plasmids containing an origin of replication, or bacteriophage (e.g. lambda or M13), both of which can replicate inside bacteria, such as E. coli, after transformation or infection, respectively. Plasmids harboring template DNA are obtained by breaking open the bacteria in which they have replicated to sufficiently high copy number, and isolating the plasmid from the supernatant. Bacteriophage released into bacterial culture supernatant after lysing the host bacteria are collected, and the DNA isolated by breaking open the bacteriophage particles. It is also possible to grow episomal agents containing mammalian origins of replication in mammalian cells, followed by isolation of the DNA according to the Hirt method.

Due to the substantial difference in molecular mass between plasmid or other episomal DNA, as compared to intact genomic DNA, use of capillary tubes as reaction chambers offers a convenient method by which to rapidly purify plasmid DNA from intact genomic DNA when both are released after lysing bacteria or other type of cells. Briefly, a mixture of plasmid and intact genomic DNA is combined in solution of chaotropic ions. A small-bore capillary into which the plasmid is desirably immobilized is dipped into the solution. The plasmids, because of their small mass, easily pass into the bore of the capillary as it fills, thereby interacting with the glass walls to establish salt-bridges and become immobilized. In contrast the intact genomic DNA, being of extremely large molecular mass, is excluded from the small bore of the capillary, and is thus separated by size exclusion from the plasmids.

As mentioned, template DNA can also be obtained without the need for cloning steps by amplifying a DNA fragment directly from an appropriate source, such as a virus, a prokaryotic cell, including bacteria, or eukaryotic cell, including mammals, other animals, or plants.

After the template DNA, FIG. 16 80, is reversibly immobilized directly to the inner surface 82 of a glass capillary tube 12, in accordance with the methods of the present invention, the capillaries are filled with the sequencing reaction mixture 84 that effects the DNA sequencing reaction. The reaction is carried out according to techniques well known in the art, whereby the products of the DNA sequencing reaction are labeled with fluorescent dyes. Well established in the art is the Sanger dideoxynucleotide chain termination technique. Briefly, a primer complementary to sequence in the template DNA molecule is permitted to hybridize to the template. Then DNA polymerase extends the primer by reading the sequence of bases in the template, by adding dNTPs to the 3' end of the growing primer. However, dideoxynucleotide triphosphates that lack the hydroxyl group characteristic of the corresponding dNTP prevent the further addition of bases to the growing strand. As a result the chain terminates. The pattern of terminated chains in a chromatogram permits the experimenter to infer the sequence of bases in the template. The terminated reaction products are fluorescently labeled either by conjugating a fluorophore to the primer that is extended, or alternatively, by conjugating a fluorophore to all the dideoxy terminators that, when incorporated into growing DNA chain, result in termination of primer extension.

In recent years, use of energy transfer, dye-coupled fluorophore systems, comprised of a light acceptor dye and fluorescence emitter dye, have improved the performance of laser scanned sequencing systems. Each dideoxy terminator is labeled with two dyes. One of these dyes, fluorescein, absorbs light energy from incident laser light produced by the laser in the sequencing machine, and transfers the collected energy via radiationless energy transfer to an acceptor dye. Each of the four chain terminators, ddG, ddA, ddT, and ddC, have a different acceptor dye coupled with the fluorescein donor. The acceptor dyes, for example, rhodamine 110, rhodamine-6-G, tetramethyl rhodamine, and rhodamine X, then emit light at their characteristic wavelengths. The fluorescence is detected by the instrument allowing identification of which nucleotide caused the termination event. Use of the energy transfer system results in more efficient excitation of the acceptor dyes than direct excitation by the laser, resulting in greater sensitivity. As an alternative to fluorescently labeling the dideoxy terminators, it is possible to label the sequencing primer. If using this system, energy transfer dyes may be used as well by conjugating to the primer a donor dye and an acceptor dye. An example of a donor dye to be conjugated to a primer is 5-carboxy-fluorescein (FAM), and examples of acceptor dyes to be conjugated to primers are rhodamine 110 (R110) for cytosine, 6-carboxyrhodamine (REG) for adenine, N,N, N',N'-tetramethyl-5-carboxyrhodamine (TAMRA) for guanine, and 5-carboxy-X-rhodamine (ROX) for thymine. The energy transfer dye-coupled fluorophore system is discussed in greater detail in issued U.S. Pat. Nos. 5,688,648, 5,707, 804, 5,728,528, 5,853,992, 5,869,255, and 6,028,190, all of which are herein incorporated by reference in their entireties.

The capillary, FIG. 16 12, containing the immobilized template DNA 80 is filled by capillary action by dipping it into a reservoir 85 filled with the reaction mixture. The reaction mixture 84 contains all the components at the appropriate concentration to effect the sequencing reaction, including water, salts, buffers, primer, DNA polymerase, dNTPs and dideoxy terminators. Without wishing to be bound by theory, at present it is hypothesized that as the aqueous mixture ascends the capillary, the immobilized DNA likely rehydrates. Furthermore, because the ionic strength of the salts in the mixture is relatively low, the salt-bridge causing the DNA to be immobilized is disrupted by the water molecules and the DNA is eluted from the inner surface of the capillary, and diffuses into the reaction mixture. Alternatively or in addition, the DNA desorbs during the thermocycling reactions. Whatever the mechanism, physical mixing of the DNA into the mixture is not necessary for performance of the reaction.

Once the capillary is filled, the ends are sealed to prevent vaporization of the liquid contained inside, followed by thermal cycling to activate multiple rounds of the sequencing reaction, so as to generate the fluorescently labeled product to be analyzed. Sealing of the capillary and thermal cycling may be effected in multiple ways, as will be apparent to the skilled artisan. If, as will often be the case, it is desirable to perform multiple sequencing reactions in parallel, the experimenter can use a high-throughput apparatus, such as that disclosed in application U.S. Ser. No. 09/577, 199, now U.S. Pat. No. 6,423,536, which is hereby incorporated by reference in its entirety. The disclosed apparatus provides means both for sealing multiple capillary tubes arranged into a cassette format, and for effecting thermal cycling of the sequencing reaction mixtures contained in the capillaries.

After the sequencing reaction is completed the reaction products are expelled from the capillary tubes, typically in preparation for analysis by capillary electrophoresis.

Typically, the reaction product is expelled onto a substrate, or into some form of holder for liquid, such as a well of a microtiter dish, from which a capillary electrophoresis system may sample the product for analysis. However the skilled artisan will recognize that it is possible for the reaction product to be expelled directly from the reaction capillary into the electrophoresis capillary. Reaction product may be expelled from the reaction capillaries by the application of centrifugal force, electrokinetically, by the application of positive or negative air pressure, or by other means known in the art.

Furthermore, the reaction product can be expelled onto a substrate adapted for other types of analytical process, such as a MALDI (matrix-assisted laser desorption/ionization) or SELDI (surface-enhanced laser desorption/ionization) substrate for mass spectrometric analysis.

During electrophoresis of the fluorescently labeled sequencing reaction products, a laser scans a window in the capillaries carrying the products and excites the fluorophores. Light emission by the fluorophores is captured and converted into intensity and light frequency data that is stored in a computer memory. After scanning and reading is complete, the computer assembles a chromatogram representing all the reaction products detected by the scanning system. The data in the chromatogram is processed by computer software that interprets the chromatogram to infer the sequence of nucleotide bases in the starting template DNA. The sequence output is then stored in a computer data file, either in random access memory or on a dedicated long term memory device, such as floppy disk, ZIP disk, JAZ disk, hard disk, CD-ROM, computer tape, etc. For the convenience of end users of the data, the computer file containing the sequence data can be stored on a computer server that can be accessed from remote client computers. When the file is transferred it is represented as a data signal associated with a carrier wave carried through copper or fiberoptic telephone lines, cable television lines, or by radio waves.

Once emptied, the capillary tubes are recycled for immobilization of new nucleic acid samples, such as DNA template to be sequenced. Recycling of the tubes requires washing to remove detrimental traces of the previous reaction, including reaction products, reaction mixture components and the immobilized nucleic acid.

Typically, the wash solution is an aqueous wash solution of low ionic strength such that any remaining immobilized nucleic acid will tend to be eluted and carried away. Double distilled water is effective. The wash solution may be heated to increase the effectiveness of washes, and the number of washes and/or volume of wash solution per wash cycle can be varied as necessary to maximize washing effectiveness. Capillaries can be filled with wash solution by capillary action and then emptied using the same methods by which reaction product is expelled. If washing is to be effected by electrokinetic pumping, then the wash solution must contain some minimum concentration of ions. Alternatively, a mechanical pump can be used to drive wash solution through the capillaries.

The washing can also be accomplished by a mechanical capillary cassette washer as disclosed in commonly owned U.S. patent application Ser. No. 09/577,199, filed May 23, 2000, now U.S. Pat. No. 6,423,536, the disclosure of which is incorporated herein by reference in its entirety.

The design for a capillary tube washing device designed to wash multiple capillaries arranged into a cassette is disclosed in application U.S. Ser. No. 09/577,199, now U.S. Pat. No. 6,423,536, herein incorporated by reference in its entirety.

After the aqueous washes, an alcohol wash, usually comprising a high concentration of ethanol is used to remove most traces of water and other components of the wash solution. The capillaries are then dried, typically by drawing warm dry air through them, after which they are ready for storage or reuse.

For some applications, it is important that essentially no nucleic acid remain from a previous reaction in the capillaries. One example is PCR, whereby old residual template DNA could be exponentially amplified leading to contamination of a new reaction. In such cases, the recycling process can comprise steps effective at destroying traces of nucleic acid. Such means include filling the capillary with a solution containing an exonuclease and incubating for such time as is necessary to digest any nucleic acid. Other means include chemical degradation of the nucleic acid, such as by washing with highly acidic or basic solutions; contact with bleach; irradiating the capillary with ionizing radiation; or baking to high temperature. After destroying residual nucleic acids, the capillaries would typically be washed using standard solutions.

One application, though by no means the only one, whereby parallel processing using capillaries in cassettes will prove useful is the confirmation of the sequence of DNA, often PCR products, for high throughput de novo sequencing, such as for discovery of single nucleotide polymorphisms (SNPs). For SNP discovery, the methods and apparatus of the present invention make possible "deep" sequencing, in which the same gene or genetic locus is sequenced from a plurality of individuals, differences in the sequence identifying polymorphisms that exist in the sequenced population. Of these, some SNPs will be demonstrated to be associated with significant phenotypes, such as predisposition, presence, or progressive potential of disease.

SNPs are single base changes that occur approximately once every 1000 bases and are the most common form of genetic variation in humans. If such polymorphisms occur in coding sequence or regulatory regions of genes, they can alter the function of the gene or gene product, as compared to the wild type sequence. Depending on the extent to which gene function is modified, the effect on the organism can minimal, or result in deleterious phenotypes, including genetic diseases.

Analysis of SNPs and their associated phenotypes is useful both in the search for genes implicated in defined disease states, as well as the new field of pharmacogenetics.

For the purpose of identifying disease genes, SNPs are used as markers for genetic linkage analysis to assist in identifying genes responsible for diseases with a strong hereditary component. Similarly, SNP analysis has proved useful for identifying changes in alleleic variants of genes correlated with important phenotypes, such as response to drug compounds or other therapeutic regimes, as well as predisposition to or progressive potential of diseases.

SNP analysis is also useful for customizing drug or other therapeutic regimes to individual patients based upon a patient's unique genetic characteristics. This is concept underlies the burgeoning field of pharmacogenetics. For example, a particular polymorphism or set of polymorphisms may be correlated with poor responsiveness to a particular drug. Further research may then show that the polymorphic changes reside in a gene encoding an enzyme responsible for metabolizing the drug, and that the changes alter the kinetic rate of the enzyme. As a result, the drug is metabolized more quickly as compared to the wild type enzyme.

Knowledge of the correlation between SNP and enzyme phenotype therefore presents an opportunity for customizing the care of patients who possess the SNP. If physicians could determine, prior to drug administration, which form of an enzyme a patient expresses, based on SNP analysis, the patient could, for example, be prescribed a higher dose of the drug to compensate for the greater metabolic rate, thereby obtaining for the patient an optimal therapeutic effect.

The approach illustrated above can be generalized to encompass any gene product that affects a drug or other type of therapeutic regime. In fact, so long as the possession, or lack thereof, of particular SNPs can be correlated with a therapeutic outcome, it is not necessary to understand the mechanism by which the genotypic change, compared to wild type, results in the altered phenotype. The knowledge of the correlation alone can be sufficient to guide physicians in modifying therapeutic regimes to suit particular patients.

SNP analysis therefore, is useful both for identifying genes that affect therapeutic regimes in human and non-human patients, and identifying those patients who will require a modified therapy compared to the patient population that lacks the SNP marker. The usefulness of SNP analysis is not limited to applications related to medical care alone, however. Indeed, identification of SNPs in the genes of any organism that can be correlated with an interesting phenotype is increasingly useful both for identifying those genes responsible for a particular phenotype, as well as those genetic alterations that cause the phenotype to be modified. Such knowledge offers an improved understanding of how particular gene products function, as well as insights as to how such functions can be beneficially modified.

Typically, SNP analysis is most beneficially undertaken in a high throughput manner, for which application of the present invention is particularly well suited. Depending on the information to be obtained, the presence of SNPs in one or a few genes is analyzed from a large number of samples from patients, or another type of non-genetically identical sources, including non-human sources. This approach is typically, but not exclusively, adopted in studies designed to obtain large data sets for correlating particular SNPs with particular phenotypes. This approach will often also be adopted by facilities that analyze SNPs present in genes of large numbers of human or animal patients, which information is to be used for customizing treatment regimes to individual patients.

Alternatively, high throughput SNP analysis may be undertaken on a large number of genes obtained from relatively few samples. This approach typically will be advantageous when a comprehensive analysis of SNPs present in a patient is desired. Such information may be necessary to customize treatment regimes in the context of diseases with complex multigene etiologies.

As is known in the art, different methods are useful for detecting SNPs in genes or gene fragments of known sequence. Most such techniques rely on indirect fluorescent detection of the single base change, as described in greater detail in "Enabling large-scale pharmacogenetic studies by high-throughput mutation detection and genotyping technologies," by M. Shi, published in Clinical Chemistry, 47(2): 164–172 (2001), which is incorporated by reference herein in its entirety. Examples include oligonucleotide ligation assay genotyping (OLA); minisequencing; TaqMan™ genotyping; Invader™ assay; dye labeled oligonucleotide ligation; pyrosequencing; and rolling circle amplification (RCA), as described further in further detail in "Sniper: a fully automated, fluorescence platform incorporating rolling circle amplification for scalable, high-throughput SNP scoring," by Z. Clark and J. Pickering, published in Life Science News 6 (2000), Amersham Pharmacia Biotech, which is incorporated by reference herein in its entirety.

An especially useful method of detection of SNPs is single base extension with fluorescence detection, also known as single base extention (SBE). SBE, in part, is based upon the dideoxyterminator approach to DNA sequencing, described above. Template nucleic acid is provided for analysis to determine whether the sequence contains one or more SNPs at particular base positions in the sequence. A primer that specifically recognizes known sequence immediately 5' of a base to be interrogated in the template is then allowed to contact and bind the template via Watson-Crick base pairing. Thereafter, a DNA polymerase, which may include a thermostabile version thereof, reads the template strand beginning at the base to be interrogated and enzymatically attaches a complementary dideoxyterminator nucleotide triphosphate (ddNTP), present in the reaction mixture, to the 3' hydroxyl group of the primer. Each of the four bases, A, C, G, T, is represented among the dideoxy-terminators present in the reaction mixture, and each of the four bases is labeled with a fluorophore that emits excited photons at a wavelength that uniquely identifies which base is present in association with the particular fluorophore. Because the dideoxyterminator cannot itself support strand extension by the DNA polymerase, extension stops after the addition of the single complementary labeled dideoxyterminator. After the extension reaction is complete, the extended primer is released, thermally or chemically, from the template and the primer is analyzed to detect the fluorophore associated with the dideoxyterminator base attached to primer 3' end. Identification of the fluorophore, based on its emission spectrum, permits unequivocal identification of the base incorporated by the DNA polymerase during single base strand extension, and the base defines the SNP present in the gene at the position interrogated.

According to an alternative embodiment, a subset, rather than all four ddNTPs may be included in the SBE reaction mixture, according to the needs and preference of the skilled artisan. Such ddNTP subsets comprise those listed in the following table.

| | |
|---|---|
| A only | C, G |
| C only | C, T |
| G only | G, T |
| T only | A, C, G |
| A, C | A, C, T |
| A, G | A, G, T |
| A, T | C, G, T |

Identification of the fluorophore can be accomplished using a variety of techniques according to the knowledge of the skilled artisan. For example, the products of a single base extension reaction can be separated from unincorporated dideoxyterminator nucleotides on a denaturing gel similar to that used for DNA sequencing. After the SBE products have been resolved by gel electrophoresis, the fluorophores associated with the primers in the gel are excited by light of the appropriate wavelengh and fluorescence emission detected and analyzed according to the knowledge of the skilled artisan. Alternatively, unincorporated dideoxynucleotides can be removed prior to analysis of the SBE products by gel electrophoresis.

According to another embodiment, fluorescently labeled dideoxterminator nucleotides incorporated into SBE extension products are detected using fluorescence polarization (FP) according to the knowledge of the skilled artisan. With this technique, polarized light is used to stimulate emission from the fluorophores. Unincorporated fluorophores are small and therefore emit depolarized light upon fluorescent excitation, whereas fluorophores incorporated into the much larger SBE extended primers emit polarized light. Preferential detection of polarized fluorescent emission can therefore be used to infer the incorporation of particular fluorophores, and therefore bases, into the extended primers. Use of FP permits analysis without prior removal of unincorporated dideoxyterminators. FP as applied to detection of SNPs is discussed in additional detail in U.S. Pat. Nos. 6,326,605; 6,310,687; 6,297,018; 6,187,267; 6,097,025; and 6,071,748, each of which is incorporated herein by reference in its entirety.

Template can be obtained, according to techniques well known in the art, from a variety of sources, including, but not limited to genomic DNA obtained from eukaroytic cells, prokaryotic cells, or viruses; episomal DNA, including plasmids; and messenger, or other types of RNA. Template can be single stranded DNA or RNA, double stranded DNA or RNA, or DNA-RNA hybrids. If template is substantially comprised of RNA, the DNA polymerase to be used to extend the primer is a reverse transcriptase (RT), including thermostable versions thereof.

According to one embodiment, the template is a PCR product obtained from genomic DNA. In this embodiment, prior to effecting the single base extension reaction, a PCR reaction is performed, using methods well known in the art, using primers that specifically recognize genomic DNA which serves as the template for PCR. Thereafter, the DNA fragment generated by PCR serves as the template for SBE. Amplified template from genomic DNA or other nucleic acid can also be obtained by a linear amplification process, or an exponential amplification process functionally equivalent to PCR.

SBE reactions have traditionally been performed in large, so-called "full volume" reaction volumes, as described in greater detail in Example 22, below. According to these methods, PCR is performed in multiple microliter reaction volumes using genomic DNA template to generate the template to be used in subsequent SBE reactions. Thereafter, the PCR products are treated with ExoI and SAP to degrade single stranded DNA and excess dNTPs, respectively. Subsequently, SBE is performed using a portion of the template generated by PCR, after which the SBE reaction products are treated with CIAP and then analyzed by capillary electrophoresis, e.g., using MegaBACE™.

Full volume reactions are performed in volumes of up to about 10, 15, 20, 25, 50, 75, 100 or 200 microliters, and as in volumes as low as about 100, 75, 50, 25, 20, 15, 10, or 5 microliters.

Although the full volume methods just described have proved efficacious, they are also wasteful of reagents and other materials because the mass of SBE product necessary to obtain high quality data is very small relative to the actual amount generated using the full volume approach. Additionally, the full volume approach demands considerable time to effect the various thermal cycling steps in PCR and SBE and to transfer fluid volumes between steps.

In contrast, application of the methods and apparatus of the instant invention to SBE and its antecedent steps can advantageously reduce use of reagents, reduce the time necessary to complete the enzymatic reactions and reduce the number of fluid transfer steps. An additional advantage is provided by template normalization which renders it unnecessary to predetermine, prior to PCR or SBE, the concentration of template in whatever solution provides its source.

As a result, use of the present invention with SBE, or other methods of SNP detection, greatly facilitates detection of SNPs in the context of high throughput methods.

In part, the advantages of the present invention as applied to SBE and other techniques of SNP detection are an effect of performing one or more enzymatic reactions in nanoliter volume (also called "nanovolume") reactions using the capillaries of the instant invention. In particular, use of nanovolume reactions reduces the quantity of reagents used, which translates to saved costs as compared full volume reactions. Nanovolumes also reduces the time necessary to proceed from one temperature to another during thermal cycling of reactions because the total mass of the reaction mixture is lower, and the surface area per unit volume of the reaction is greater when using capillary tubes as compared to the reaction tubes used for full volume reactions. Both effects increase the rate of heat transfer and thereby reduce the time necessary to perform an entire series of thermal cycles. Lastly, as discussed in more detail below, template capture, i.e., the reversible binding of template to the internal surface of the capillary in the presence of a chaotrope, permits elimination of one or more steps necessary to perform SBE, further reducing reagents, costs, and time associated with performing the assay.

As used throughout, nanoliter volume reactions are performed in volumes of up to about 25, 50, 100, 250, 500, 750, 1000, 1500, 2000, 2500, 5000, or more nanoliters, and in volumes as low as about 2500, 2000, 1500, 1000, 750, 500, 250, 100, 50, 25, 10, or fewer nanoliters.

According to an embodiment of the present invention, template dissolved in chaotrope solution is withdrawn into a capillary of the present invention by capillary action, or other method as described herein, and contacts the inner surface until a predetermined approximate mass of such template is caused to bind reversibly thereto. After binding is complete excess template in chaotrope is removed and the bound template washed as explained elsewhere herein. After a futher optional drying step, SBE reaction mixture, containing all ingredients necessary to effect SBE, including buffers, salts, water, SBE primer, fluorescently labeled ddNTPs, and DNA polymerase, is drawn into the capillary by capillary action, or other method described herein. Subsequently, the capillary containing the template and SBE reaction mixture is exposed to thermal cycling as necessary to effect SBE.

According to an alternative embodiment, SBE template may be reversibly bound to the inner surface of a capillary in the presence of chaotrope until an amount of template, as determined by the skilled artisan, is bound which is sufficient to yield detectable SBE product after conducting the reaction. That is, it is not necessary that a predetermined approximate mass of SBE template be reversibly bound inside the capillary for the usefulness of the present invention to be realized.

After the reaction is completed, SBE product is typically expelled from the capillary, as described elsewhere herein, for subsequent processing, including removal of unincorporated ddNTPs, e.g., by treatment with calf intestinal alkaline phosphatase (CIAP), according to methods known in the art. As understood by the skilled artisan, CIAP treatment removes phosphate groups from ddNTPs, rendering the dephosphorylated ddNTPs uncharged. As a result, during electrophoresis, e.g., using MegaBACE™, the treated ddNTPs are not induced to move by the strong electric field that causes the charged SBE products to enter the sieving gel. This approach facilitates separation of unincorporated ddNTPs from the SBE products.

CIAP treatment may be effected in full volume reactions, or alternatively, in nanovolume reactions. Full volume CIAP treatment is conveniently performed in the wells of microtiter plates, e.g., 96, 384, 1536, or higher numbers of wells per plate. In contrast, nanovolume CIAP treatment is performed within a capillary of the present invention after having mixed the SBE product with CIAP reaction mixture, e.g., within a well of a microtiter plate.

As an alternative to treatment of SBE products with CIAP, excess unincorporated ddNTPs may be removed by contacting the SBE reaction products with a gel filtration media for sufficient time to separate ddNTPs from SBE products. Complete separation is not necessary; the extent of separation which is sufficient is within the knowledge of the skilled artisan. Gel filtration media is chosen with properties that ensures that ddNTPs can enter the pores of the media whereas SBE products are substantially excluded. In this manner ddNTPs are contained in the total volume, whereas SBE product is contained within the void volume. Examples of media suitable for use in the present invention include, but are not limited to superdex, superose, sephacryl, and sephadex.

Finally, the SBE products are analyzed to identify the incorporated bases. As described elsewhere herein, one such method is capillary electrophoresis using the MegaBACE™ system. Electrophoretic methods coupled with a microfluidic platform can also be used to resolve extension products of SBE. Such methods are discussed in more detail in U.S. Pat. Nos. 6,316,201; 6,306,659; 6,306,590; 6,303,343; 6,287,774; 6,274,337; 6,267,858; 6,235,471; 6,235,175; 6,174,675; 6,153,073; 6,107,044; 6,068,752; 6,042,710; 5,976,336; 5,965,410; 5,958,694; and 5,948,227, each of which is incorporated herein by reference in its entirety.

Alternatively, SBE products can be analyzed using mass spectrometric techniques, including matrix-assisted laser desorption/ionization (MALDI) or surface-enhanced laser desorption/ionization (SELDI).

According to an alternative embodiment, SBE template can be drawn into the capillary of the instant invention having already been mixed with the SBE reaction mixture, in which case template normalization does not occur.

According to another embodiment of the instant invention, template for SBE is prepared by PCR, according to methods well known in the art.

PCR may be effected in full volume reactions. After PCR is completed, the reaction can be treated to remove primers and dNTPs, as described in further detail below. Then, according to one embodiment, the PCR products are mixed with chaotrope and used to fill a capillary of the instant invention for template normalization of the SBE template, followed by the extension reaction, as described above. In an alternative embodiment, a portion of the PCR products, after treatment, are added to SBE reaction mixture and used to fill a capillary of the instant invention for subsequent performance of the extension reaction, as described above.

PCR may also be performed in a capillary of the instant invention using nanoliter volume reactions, in which case PCR may be preceded by template normalization of the genomic DNA, or other PCR template, to be used in the reaction, similarly as described above for SBE template. Alternatively, PCR template may be added to the PCR reaction mixture prior to filling the capillary, in which case template normalization does not occur.

Following PCR, the reaction product typically is expelled from the capillary, as described elsewhere herein, and treated to remove primers and dNTPs, as described in further detail below. As in the case of full volume PCR, treated PCR products may then be mixed with chaotrope and used for template normalization of the SBE template, or added to SBE reaction mixture. Extension reactions are then performed as described elsewhere herein.

As mentioned above, after PCR is completed, PCR product is typically expelled from the capillary, as described elsewhere herein, and treated to remove excess unincorporated PCR primers and dNTPs by, for example, using a single stranded Dnase, e.g., exonuclease I (Exo I), and a phosphatase, e.g., shrimp alkaline phosphatase (SAP), respectively, according to methods known in the art. PCR product, as SBE template, may then be normalized, or added directly to SBE reaction mixture, and used in SBE in a capillary of the present invention, as described above.

ExoI/SAP treatment may be effected in full volume reactions, or alternatively, in nanovolume reactions. Full volume ExoI/SAP treatment is conveniently performed in the wells of microtiter plates, which plates may comprise 96, 384, 1536, or higher numbers of wells per plate. In contrast, nanovolume ExoI/SAP treatment is performed within a capillary of the present invention after having mixed the PCR product with ExoI/SAP reaction mixture, e.g., within a well of a microtiter plate.

According to an alternative embodiment, after PCR, whether conducted in full volume or nanovolume reactions, the PCR product treatment step is exluded. Rather, to effect removal of excess unincorporated primers and dNTPs, the PCR products are added directly to chaotrope, after which the solution is used to fill a capillary of the instant invention until such time that a predetermined approximate mass of template, or a mass of template sufficient to yield detectable SBE products, is reversibly bound to the inner surface of the capillary. Thereafter, excess unbound PCR product (i.e., SBE template), primers, and dNTPs are removed by washing, as described elsewhere herein. After an optional drying step, SBE reaction mixture is then drawn into the capillary for subsequent performance of the extension reaction, as described elesewhere herein.

At each stage of the procedure that uses nanovolume reactions in capillaries of the instant invention, a new capillary may be used. Alternatively, the same capillary from one or more previous steps may be reused, with, or without first having washed the interior of the capillary, or otherwise treat the capillary, to remove or inactivate traces of reagents, reactants or products deposited therein from the previous step. Methods of washing or treating capillaries of the instant invention are discussed elsewhere herein.

In a preferred embodiment, a plurality of the capillaries of the present invention are provided arranged in a spatially addressable array to facilitate high-throughput processing of multiple samples in parallel. Typically, the number and pattern of capillaries in an array and the dimensions of an array of capillaries corresponds to the number, pattern and dimensions of wells in one or more types of microtiter plates such that an capillary array and wells of a plate can be mated, preferably in the context of an automated or semi-automated robotic work flow system. Often, but not necessarily, arrays are rectangular, but may be circular, triangular, etc. The number of capillaries in an array may include 2, 4, 8, 12, 16, 24, 32, 48, 64, 96, 128, 192, 288, 384, 480, 576, 672, 768, 864, 960, 1536 capillaries, or higher number of capillaries. Methods of arranging capillaries into arrays of chosen number, pattern and dimension are described elsewhere herein, or are otherwise known to the skilled artisan. Multiple PCR and SBE reactions can be performed in parallel using arrays of capillaries using an apparatus for performing high-throughput reactions, such as that disclosed in application U.S. Ser. No. 09/577,199, now U.S. Pat. No. 6,432,536, which is hereby incorporated by reference in its entirety.

Another application whereby parallel processing using capillaries in cassettes will prove useful is the confirmation of the sequence of DNA, often PCR products, intended to be spotted on to a substrate to create a microarray. Such microarrays are finding increased use in basic and applied research and are typically comprised of a rectangular array of spots of DNA on a glass slide, with a different, known DNA sequence at each spot. The experimenter then takes a labeled sample, either RNA or DNA and detects hybridization events between the labeled nucleic acid and the DNA spotted to the array. In this way, the experimenter can infer the identity and/or partial or complete sequence of the labeled nucleic acid.

To ensure the integrity of the data generated using microarrays, it is necessary that the identity of the sequence of the spotted DNA be known with high confidence. Rearraying and other sample handling procedures introduce formatting errors that must be detected. Furthermore, PCR is often used to generate the DNA to be spotted. As is well known in the art, Taq and other thermostable polymerases introduce a certain number of erroneous base pairs per thousand as it amplifies the template. If errors have been introduced, they must be detected, and the amplified product discarded. Usually, this requires numerous processing steps separate from those associated with spotting the PCR product. However, use of an embodiment of the present invention greatly increases the efficiency of sequence determination and confirmation.

The DNA sample to be spotted is usually dissolved at a predetermined concentration in a solution comprising chaotropic ions, for example sodium thiocyanate. The DNA is so dissolved because it is to be immobilized to the surface of the glass microarray slide in a manner similar to that by which nucleic acid is immobilized inside capillary tubes. Typically the different DNA-chaotrope solutions are aliquoted into wells of 384-well capacity microtiter dishes for storage until ready to be spotted onto a microarray. Prior to spotting the dish is picked up by a robot associated with a automated spotting system and manipulated into a position whereby the spotting styli or pens can be dipped into multiple wells, usually 12, at one time.

The present invention can be adapted to sample and sequence the DNA in multiple wells of the same 384-well dish used as the DNA source for the spotting pens. It will be apparent that it can also be adapted to sample from dishes with more than 384 wells. Because the DNA to be sequenced is from the same sample to be spotted, numerous processing steps associated with sequencing the DNA from different samples are obviated. This results in substantial savings of time and material costs. According to this embodiment of the present invention, glass capillaries are arranged into a cassette in the same pattern and inter-capillary dimensions as that of the wells in one or more rows or columns of the dish. For maximal capacity, a total of 384 capillaries are arranged into a pattern with dimensions identical to that of the dish itself. Prior to spotting, the capillary cassette is filled with DNA-chaotrope solution (usually sodium thiocyanate) according to the methods of the present invention. After the DNA samples are immobilized and processed, they are sequenced. If any of the templates fails to give the correct sequence, the operator of the spotting apparatus knows not to spot that DNA, or if spotted, that data associated with hybridization at the corresponding spot is to an unwanted sequence and should be removed from the resulting data set.

Alternative Biochemical Reactions with Reversibly Immobilized Nucleic Acids

The present reaction mixture assembly may be used for assembly of numerous types of reactions. The same basic method used to assemble the PCR reaction mixture may be adapted to assembly of a cycle sequencing mixture, rolling circle amplification reaction mixture, enzymatic assays, chemical reactions, or other reaction mixtures.

Dispensing a Predetermined Quantity of a Nucleic Acid

As will be readily apparent, the experimenter is not obligated to carry out a reaction with the nucleic acid immobilized inside of a capillary tube. For a variety of reasons, it may be preferable to elute the immobilized nucleic acid from the inner surface of the capillary and either perform a reaction with it in a different reaction chamber, or to process the nucleic acid in some other way outside of the capillary. In such circumstances, it is possible to use the capillary as a pipettor to dispense a predetermined approximate mass of the nucleic acid in a fixed volume of liquid, and therefore at a predetermined approximate concentration, onto a substrate of the experimenter's choosing. To do so, the capillary is filled with elution fluid that elutes essentially all the reversibly immobilized nucleic acid. Thereafter, the solution of the elution fluid and nucleic acid is dispensed, usually onto or into a substrate. The substrate onto which the reaction mixture is transferred may be the wells of a multiwell microtiter plate, locations on a planar substrate, or wells that lead into an analytical chip. The reaction may also be dispensed into a solution for further chemical or biochemical reaction.

If multiple capillaries are arranged into a cassette, as described above, the cassette becomes a multichannel parallel pipettor, and it becomes possible to dispense a large number of normalized nucleic acid samples simultaneously. The dispensing can be into microtiter wells, microchips, and other chambers for further reactions. In addition, the nucleic acid can be dispensed directly into the reservoirs of a capillary array electrophoresis microchip or onto a MALDI or SELDI target, or onto or into a substrate adapted to be used in other analytical modalities.

Different methods may be used to expel or dispense liquid from capillary tubes. As will be appreciated by the skilled artisan, these methods can be employed to dispense not just an eluted nucleic acid solution, but also for removing the liquid from a filled capillary regardless of purpose, such as to remove reaction product after a reaction, or to remove washing solutions.

One method to dispense the contents of a single capillary tube or multiple similar capillaries arranged into a cassette format uses a centrifuge to dispense the fluid by centrifugal force. The centrifugal force is applied evenly to all of the capillaries in the capillary cassette such that capillaries independently dispense their contents onto a substrate situated below the orifice to the capillary from which fluid is expelled. If the substrate is a well of a microtiter dish, the dispensed liquid will be drawn by centrifugal force to the bottom of the wells. The design for a centrifuge and associated rotor and buckets to hold a cassette is disclosed in application U.S. Ser. No. 09/577,199, now U.S. Pat. No. 6,423,536, herein incorporated by reference in its entirety.

A second method of dispensing the liquid contained in a capillary tube is through the use of an air displacement device. The design for an air displacement device designed to dispense the liquid contents of multiple capillaries arranged into a cassette is disclosed in application U.S. Ser. No. 09/577,199, now U.S. Pat. No. 6,423,536, herein incorporated by reference in its entirety.

Alternatively, the contents of a capillary could be dispensed directly into a well, or sample port (FIG. 3E 76) of an analytical device (FIG. 3E 70), such as an electrophoresis chip. As shown in FIG. 3E, such an analytical chip would have an array of analytical lanes 78 in fluid communication with their respective sample inlets or ports 76. Multiple capillaries may be arranged into a cassette format such that the spacing of the capillaries matches the spacing of the sample inlets 76 in the chip. For example, a capillary cassette having 16 capillaries in two parallel rows of eight may dock with 16 wells in an analytical chip.

As an example, the capillary cassette illustrated in FIG. 3C includes capillaries 12 extending through flexible strip 11. Flexible strip 11 may be used alone or in combination with other such strips. The orientation of the capillaries in an essentially straight line may be altered by bending strip 11 to form an arc. FIG. 3D illustrates strip 11 bent to allow capillaries 12 to mate with input ports that are disposed on a substrate in a circular pattern. The liquid in capillaries 12 may then be electrokinetically injected or otherwise dispensed from capillaries 12 into ports 76 of an analytical chip 70 if an appropriate electrode array or other dispensing methods are used. Strip 11 may be positioned in the curved orientation by pressing strip 11 against a curved form, such as a curved metal block. This may be done by an automated strip mover incorporated into an automated sample preparation system.

The capillary cassette could be dispensed by air displacement or other dispensing means preferably selected to minimize splattering and bubble formation. Prior to dispensing the prepared reaction mixture into the wells 76 for analysis, a small amount of a diluent could be added to each analytical microchip well 76. When the capillary cassette is dispensed, the diluent will dilute the samples in the sample wells 76. The submicroliter volume reaction mixtures prepared in the capillary cassette, such as a DNA sequencing reaction product mixture, can readily be integrated with the analytical chip for sequencing or other analysis methods.

The elution fluid is preferably an aqueous solution of low ionic strength, more preferably water or a low ionic strength buffer at about a pH at which the nucleic acid material is stable and substantially intact, usually between pH 6.5 and 8.5. TE Buffer at 1× concentration (10 mM Tris-HCl, 1 mM ethylenediamine-tetraacetic acid (EDTA), pH 8.0) and distilled or deionized water are particularly preferred elution solutions for use in the present invention. The low ionic strength of the preferred forms of the elution solution described above will tend to disrupt the salt-bridges established between the nucleic acid and the material comprising the inner surface of the capillary, ensuring that the nucleic acid is eluted into the solution. Other elution solutions suitable for use in the methods of this invention will be readily apparent to one skilled in this art.

According to the methods of the present invention, nucleic acid binding to the inner surface of the glass capillary tube is saturable. Under appropriate conditions, it is possible to control, with a high degree of accuracy, the quantity of nucleic acid immobilized inside any particular capillary. Thus, if the nucleic acid is eluted into an aqueous solution and dispensed, the concentration of the nucleic acid in the solution can be known, as well as the total quantity of nucleic acid in any particular volume of that solution. For example, if a capillary's binding capacity is 10 ng DNA, and this is eluted into 500 nl of elution fluid, the concentration of the solution is 0.02 grams per liter, with the molar concentration dependent on the molecular mass of the DNA molecules. If all 500 nl is dispensed, that droplet contains 10 ng DNA.

As will be understood by the skilled artisan, due to small variations among different capillary tubes, the amount of nucleic acid that can be immobilized and eluted, although highly consistent, is not identical between capillary tubes, or even between repeated use of the same tube. For this reason, the predetermined quantity or mass of nucleic acid eluted into the elution fluid is an approximate quantity or mass. Preferably, in this context, predetermined approximate mass shall mean that between similar capillaries, or repeated use of the same capillary, all other conditions being equal, the error between the mass expected to be immobilized or dispensed and actually immobilized or dispensed is not greater than 10%, more preferably 5%, more preferably 2%, and most preferably not more than 1% error.

Usually, the dispensing function of the present invention will be utilized by immobilizing a saturating quantity of nucleic acid in a particular capillary and dispensing the entire volume. Thus, to control the quantity and concentration of dispensed nucleic acid, the experimenter will choose a capillary with a predetermined binding capacity and volume. However, as discussed above, the experimenter can empirically determine conditions under which a predetermined non-saturating quantity of immobilized nucleic acid is bound. Accordingly, using these conditions, a non-saturating predetermined quantity of nucleic acid can be immobilized and then eluted from a capillary, allowing the experimenter to dispense any given amount of nucleic acid at will.

Under both circumstances, where a capillary has reversibly bound a predetermined quantity of nonsaturating, or saturating nucleic acid, if the experimenter, using methods familiar to the skilled artisan, controls the amount of nucleic acid-elution fluid expelled from the capillary, then knowledge of that volume permits dispensing precise amounts of nucleic acid. For example, controlled amounts of the fluid can be expelled by mechanical pumping, or electrokinetic pumping.

A Highly Parallel Submicroliter System for Enzymatic Reactions

In another aspect, the invention provides methods and apparatus for performing enzymatic reactions—particularly, but not limited to, isothermal reactions—in small volumes, particularly submicroliter volumes. The reactions can be performed in highly parallel fashion, and can readily be interfaced, in parallel, and without substantial loss of reactants to high resolution electrophoresis instrumentation for analysis.

The enzymes include any that are commonly used in larger-scale assays, including proteases, such as trypsin, chymotrypsin, proteinase K, papain, pepsin, endoproteinase Glu-C, Arg-C, Lys-C, Pro-C, V8 protease, glycosidases, such as β-galactosidase, lipases, oxidases and oxygenases, such as glucose oxidase, cholesterol oxidase, and lactate monooxygenase, ligases, including DNA and RNA ligases, methylases, polymerases, such as DNA-dependent DNA polymerase enzymes, terminal transferase enzymes, RNA-dependent DNA polymerase enzymes, DNA-dependent RNA polymerase enzymes, phosphatase enzymes, kinase enzymes, DNA gyrase, topoisomerases, nucleases, including exonucleases, such as S1, or mung bean nucleases, and endonucleases, such as restriction endonucleases, other nuclease enzymes, and ribonuclease enzymes, and urease.

The submicroliter protein reactions are not limited to use of enzymes, and thus catalysis of chemical reactions. For example, proteins can be used for their ability to bind other molecules, and thus capture them from solution. For example, proteins can be antibodies or antigen-binding fragments thereof, such as IgG, IgE, IgM; protein G and Protein A; and streptavidin, to name a few.

Where the protein is an enzyme, the substrates are dictated by the chosen enzyme and are, accordingly, as varied as the enzymes, and include nucleic acids, including DNA and RNA, carbohydrates, lipids, and other biological and chemical substrates.

For demonstration purposes herein, submicroliter protease assays using trypsin protease—a sequence-specific protease commonly used in the art for mass spectral peptide mapping and sequencing—are used herein to demonstrate the usefulness of such a system in proteome research and as a drug discovery platform. Submicroliter protease assays using endoproteinase Asp-N as the enzymes are presented herein to demonstrate the usefulness of such a system in bioassay and drug discovery research. As would be understood, other enzymes, indeed other noncatalytic proteins, can be used in this multiplex submicroliter reaction system.

Homogeneous Assay in Small Volumes

In a first embodiment, capillaries (or channels) having submicroliter volumes are used as reaction chambers for small volume enzymatic assays, and can be usefully be used in cassettes, or arrays, to conduct such assays in highly parallel fashion without significant loss of reagent or reactants before analysis.

The capillary typically has an internal volume of not more than 5 µL, often no more than about 2 µL, frequently no more than 1 µL, typically no more than about 750 nL, 500 nL, 400 nL, and even no more than about 250 nL, 200 nL, even no more than 100 nL.

For example, Example 26 demonstrates trypsin digestion of cytochrome C in homogeneous solution. Mixtures of trypsin and cytochrome C are prepared in solution at various trypsin-protein ratios, with the concentration of cytochrome C fixed at 1 mg/mL. Aliquots of the mixture are drawn into the capillaries of a capillary cassette by capillary action, and incubated at 37° C. overnight to allow the protease reaction to complete. Digestion mixtures are then spun down in parallel to a 96-well microtiter plate, each of the wells of which contains fluorescein-5-isothiocyanate (FITC) labeling solution. After reaction in the dark, the resulting mixtures are subjected to capillary electrophoresis (CE) separation on the MegaBACE™ 1000 (Amersham Biosciences, Piscataway, N.J.), a high resolution and high throughput instrument.

Example 27 demonstrates homogeneous assay with Asp-N, further demonstrating the multiplexing capacity of the current methods. In addition, Example 27 demonstrates that analysis can be conducted in parallel using scanners.

Figure 36:
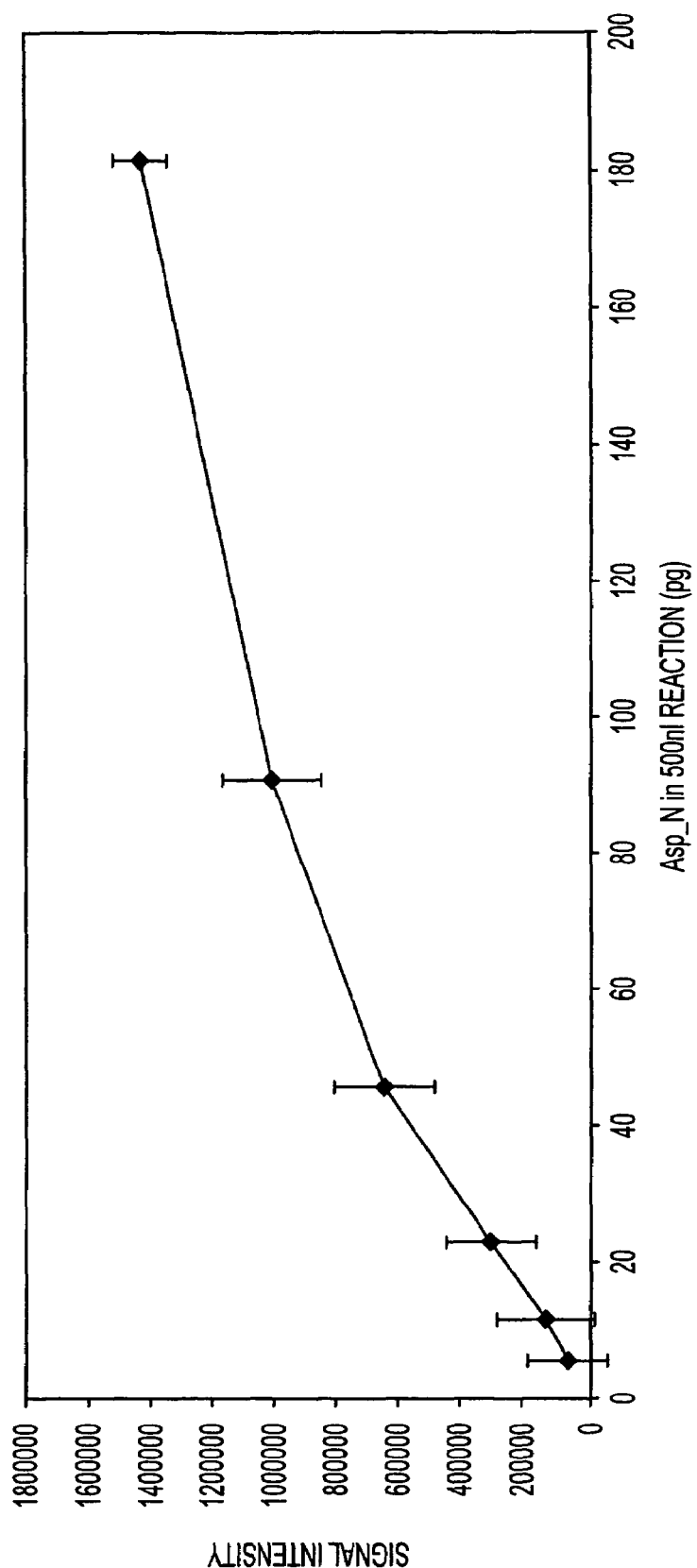
FIG. 36 presents the relationship between Asp-N concentration and the amount of polypeptides digested, represented here by signal intensity of the Cy3 emission from the digested peptides.

Briefly, peptide Cy™5Q-YVADAPVK-Cy3 (SEQ ID NO:1) is reconstituted in assay buffer, then mixed with endoproteinase Asp-N of various concentrations. 500 nL aliquots of the mixture are captured by a capillary cassette system due to capillary action, and incubated at room temperature to allow the reaction to complete. Digestion mixtures were then spun down to a 384 clear scan plate of which each well contains 10 uL of buffer. The resulting mixtures were scanned on Typhoon™ (Amersham Biosciences, Piscataway, N.J.) to detect Cy3 emission. The signal intensity of the Cy3 emission increases linearly as the Asp-N concentration increases, up to 50 picogram per 500 nL reaction. Beyond that, Cy3 signal intensity continues to increases with the Asp-N concentration, up to 180 picogram per 500 nL reaction (FIG. 36).

Bead-Immobilized Enzyme in a Multiplexed Capillary Reaction

In a second embodiment, the enzyme is immobilized on a particle, or bead, so dimensioned as removably to fit within a capillary or channel, such as those present in multicapillary cassettes, such as that shown in FIG. 3.

Preferably, the capillary or channel has a small internal volume, desirably from about 1–1000 nanoliters (nl), more desirably from about 10–500 nl, most desirably from about 100–500 nl; the bead is dimensioned itself to fill no more than about 75%, typically no more than about 50%, often no more than about 40%, 30%, 20% and even as little as 10% of the capillary volume. Often, the bead or particle is sufficiently small as to be movable solely by entrainment in the reaction volume, and thus to be of such size as to be suitable for uptake into the capillary solely by capillary action.

Beads suitable for surface immobilization of enzymes are known and are available commercially from a variety of vendors, such as Dynal, Miltenyi Biotec, and others.

Beads can usefully be magnetic or superparamagnetic, and can usefully be derivatized to permit the ready attachment of proteins or other moieties thereto.

In addition, the beads can usefully include a scintillant, permitting scintillation proximity assay (Amersham Biosciences, Inc., Piscataway, N.J.). In such assays, the polymer beads contain scintillant that can be stimulated to emit light, stimulation occurring only when radiolabelled molecules of interest are bound to the surface of the bead.

The enzyme can be immobilized on the external surface of the bead or, if the bead is porous and the pores are of sufficient size to permit enzymatic substrate to diffuse therewithin, within the bead itself.

In one set of experiments further described in the Examples, below, trypsin immobilized on the surface of magnetic beads are used. Introduction of small magnetic beads eliminates the need for separating the enzyme from the reaction mixture prior to analysis, minimizes contamination by the proteolytic enzyme, and provides high binding surface area per unit volume for optimal accessibility of target molecules. Beads are prepared by incubating streptavidin-coated magnetic beads M280 (Dynal, Oslo, Norway) with biotin-conjugated trypsin (Sigma, St. Louis, Mo.). These trypsin immobilized magnetic beads were then mixed with cytochrome C for tryptic digestion using the capillary cassette. After incubation in an oven at 37° C. overnight, the digestion mixtures are separated from beads, and labeled by FITC fluorescent dye. The resulting protein fragments are analyzed by MegaBACE™ 1000 (Amersham Biosciences, Piscataway, N.J.).

Figure 31A:
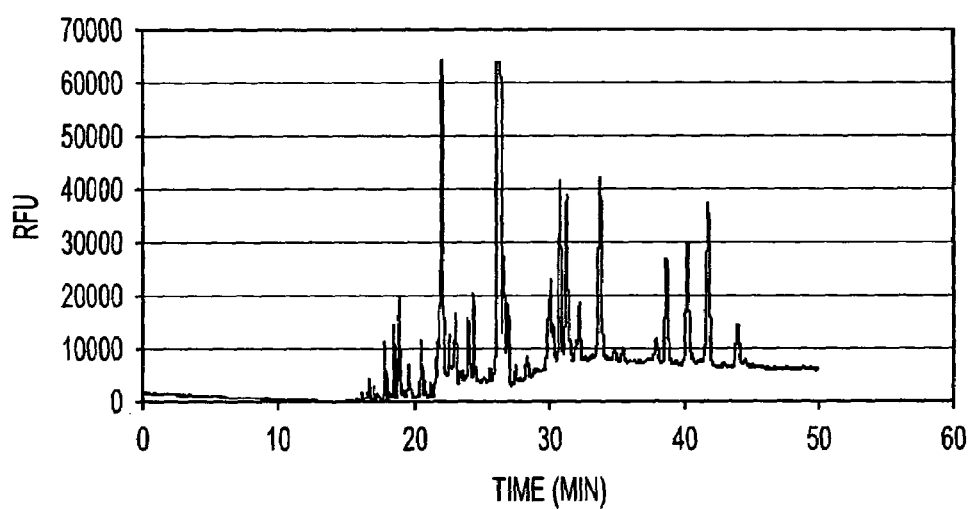
FIG. 31 illustrates a representative peptide profile of cytochrome C, after protease digestion by trypsin in a capillary cassette. The profile was generated by MegaBACE™ analysis. Trypsin is either in solution (FIG. 31A) or immobilized on magnetic beads (FIG. 31B)
Figure 31B:
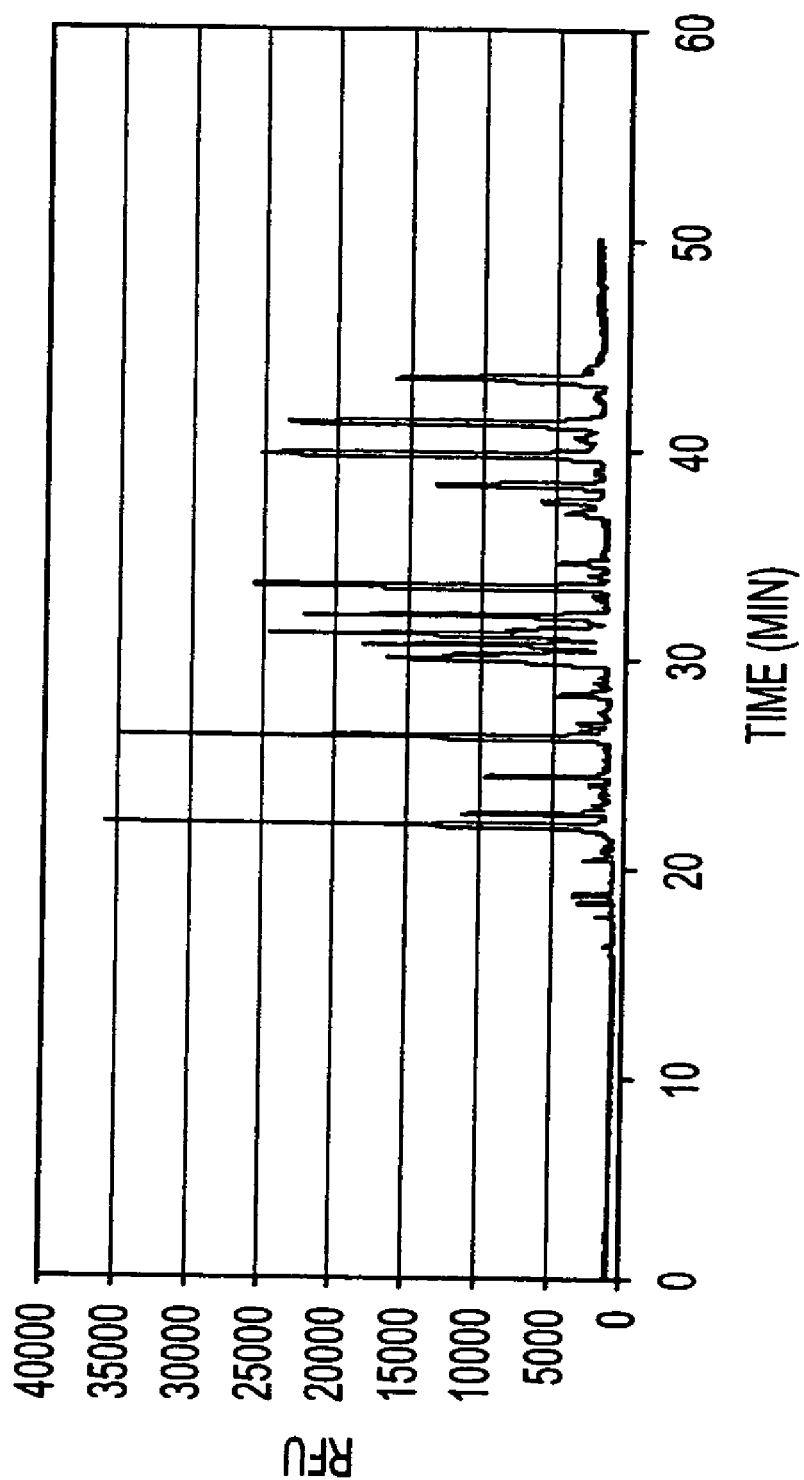

Capillary electrophoresis separation of tryptic digestion products of cytochrome C on the MegaBACE™ shows that the peptide profiles obtained from the two approaches are consistent and reproducible. A representative electropherogram of cytochrome C digestion from a capillary cassette reaction is illustrated in FIG. 31B.

The nanoscale enzymatic reaction systems offer unique advantages over the full volume reaction systems. The small reaction volume (nanoliter range) greatly reduces the quantity of samples (picomole range) and reagents required, as well as the sample preparation time. It also offers enhanced reaction sensitivity. The concurrent multiplex format makes it possible to integrate it in a fully automated system for high throughput analysis and identification of biomolecules, as well as using it in a manual format. All these can be translated into shortened running time per assay, and reduced consumption of reagents and samples, resulting in substantial cost savings.

Immobilization of Protein in a Reaction Chamber for Enzymatic Reaction

In a third embodiment, the enzyme is immobilized to an interior surface of the reaction chamber, usefully a channel or capillary having submicroliter volume.

Nonspecific immobilization of enzyme can be achieved by simple adsorption onto a relatively hydrophobic solid phase. The passive adsorption of the enzyme is through its exposed hydrophobic sites. Such a process, however, is not completely general, and the optimal conditions for binding often have to be found by trial and error. Enzymes bound to the solid phase via multiple amino acid groups risk deformation of the active site and hence reduced reactivity.

Accordingly, there is typically a need to modify the attachment surface with specific functional groups to tether enzyme molecules.

In one approach, silanization with aminoalkylsilane reagents gives a surface that is functionalized with amino groups to which a wide variety of affinity ligands can subsequently be attached.

Thus, capillaries of capillary cassettes such as those shown in FIG. 3 and described above, or other kinds of reaction chambers having small volumes, can be treated, e.g., by 3-aminopropyltriethoxy silane, followed by N-succinimidyl 3-(2-pyridyldithio) propionatel. The pyridyldithio functional group provides a convenient way to bind proteins, such as enzymes, through specific —S—S— and —SH exchange reactions. Furthermore, if needed the immobilized enzyme can be released by adding an excess amount of thiopyridone, regenerating the derivatized surface for tethering fresh trypsin to ensure high enzyme reactivity.

Another surface immobilization approach is based on a specific streptavidin-biotin reaction. Streptavidin modification enables the surface to bind biotinylated enzymes. In this approach, capillary cassettes can be derivatized, e.g., with 3-aminopropyltriethoxy silane, and then reacted with a bifunctional linker, such as disuccinimidyl suberate, which in turn tethers streptavidin; the streptavidin thereafter can bind any biotinylated enzyme to the reaction chamber (typically capillary) interior surface. If the enzyme is biotinylated at a unique site—e.g., by enzymatic biotinylation of a biotin-binding site engineered into the enzyme—the high affinity, high specificity streptavidin and biotin interaction results in uniformly oriented enzymes on the inner surfaces of the capillary.

These protein immobilization techniques offer high surface reactivity and minimized nonspecific binding. In addition, as further described in the Examples, below, we have found that proteins immobilized by such approaches remain bound, and functional, even after completing a reaction; the capillary can thus be used serially for a plurality of reactions without requiring recharging with enzyme.

Other surface immobilization approaches can also be utilized. Reaction with γ-glycidoxylpropylsilane introduces oxirane groups to the solid surfaces that allow coupling enzyme at lysine sites. This modification is expected to provide more hydrophilic surfaces to reduce unspecific protein uptake. Conjugating enzyme with surface-active hydrogels offers yet another convenient means to produce enzyme immobilized surfaces (Caldwell, Carlsson and Li, U.S. Pat. No. 5,516,703). An advantage of this approach is that it provides protein-compatible environments and reusable surfaces.

To evaluate the reactivity of the enzymes immobilized by the above protocols, protein digestion reactions were conducted by contacting a model protein, cytochrome C, to trypsin-coated capillaries of a capillary cassette. The reactions were carried out at 37° C. overnight. Protein fragments were then labeled with fluorescein isothiocyanate (FITC), and analyzed using a MegaBACE™ 1000 machine. Capillary cassettes coated with trypsin through nonspecific immobilization were used as the control.

Figure 32:
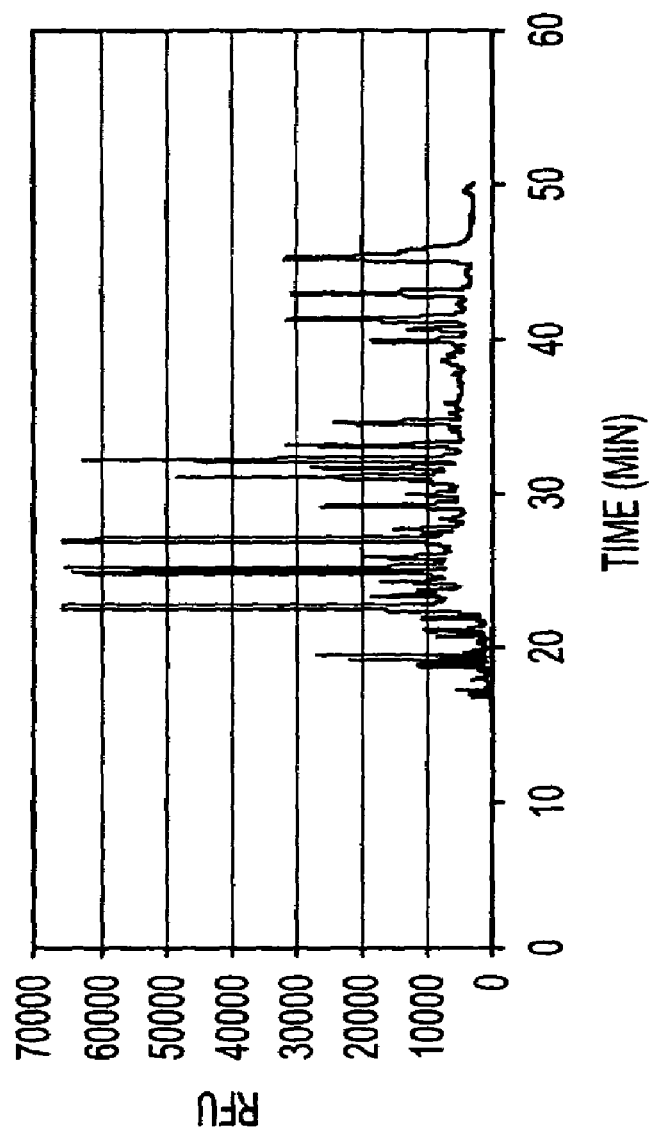
FIG. 32 presents a representative first run of a peptide profile of cytochrome C, after protease digestion by trypsin that is covalently coated onto an internal surface of a capillary in a multi-capillary cassette. The internal capillary surface was modified by either aminoalkylsilane reagent or streptavidin modification. The profile was generated by MegaBACE™ analysis.
Figure 33:
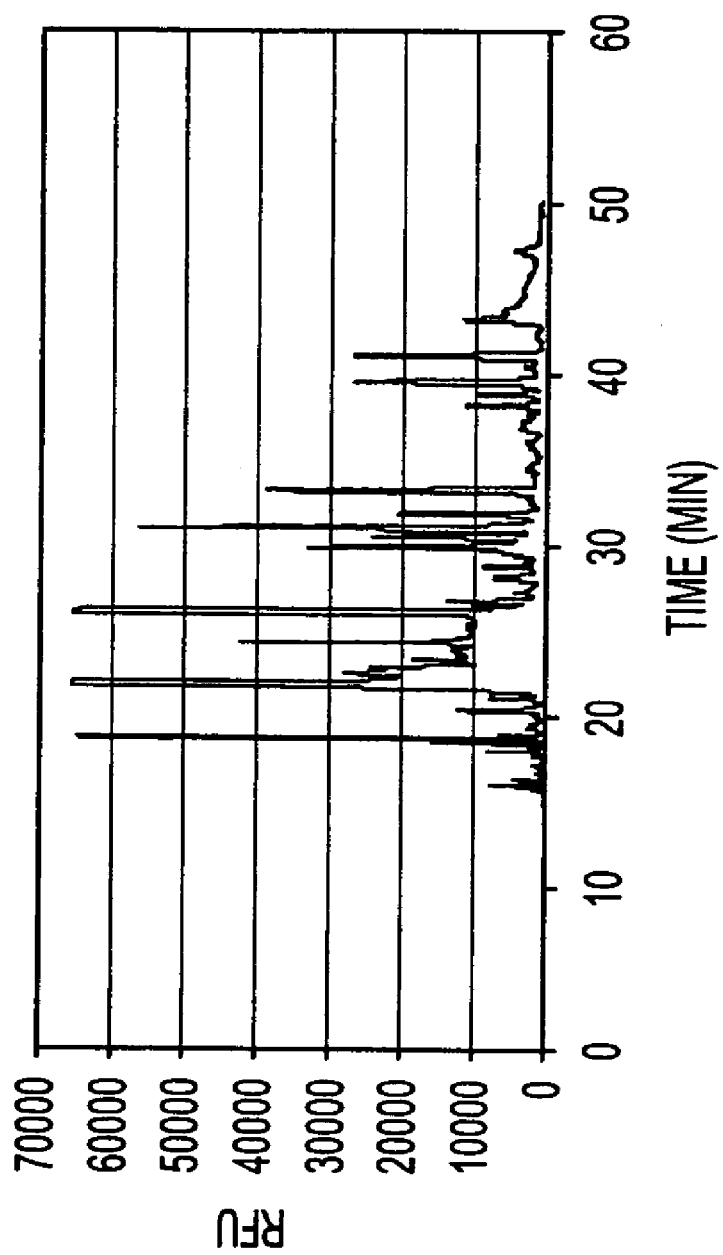
FIG. 33 presents a representative second run of a peptide profile of cytochrome C, after protease digestion by covalently surface-coated trypsin. The capillary surface was modified by either aminoalkylsilane reagent or streptavidin modification. The profile was generated by MegaBACE™ analysis.
Figure 34:
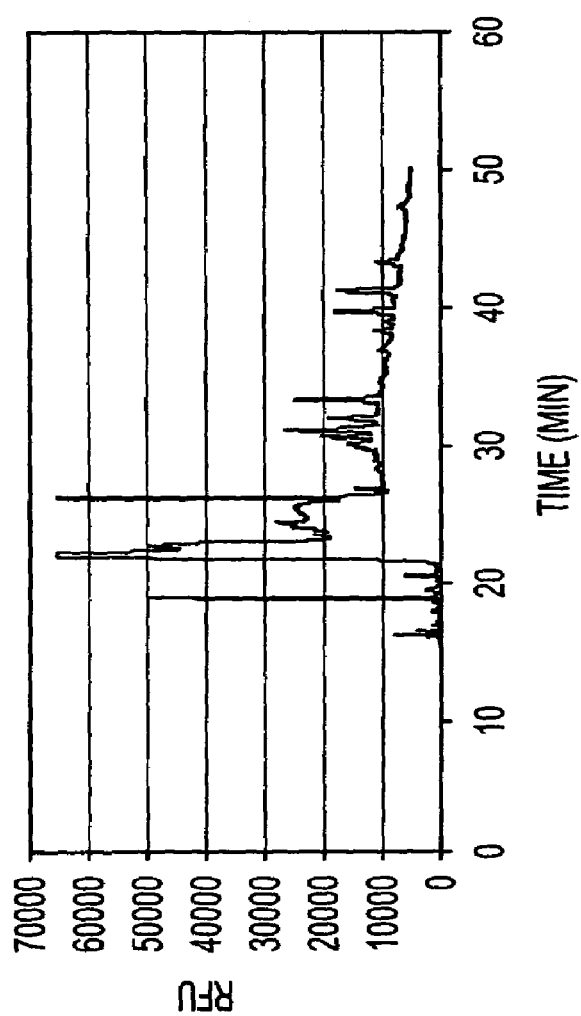
FIG. 34 presents a representative third run of a peptide profile of cytochrome C, after protease digestion by covalently surface-coated trypsin. The capillary surface was modified by either aminoalkylsilane reagent or streptavidin. The profile was generated by MegaBACE™ analysis.
Figure 35:
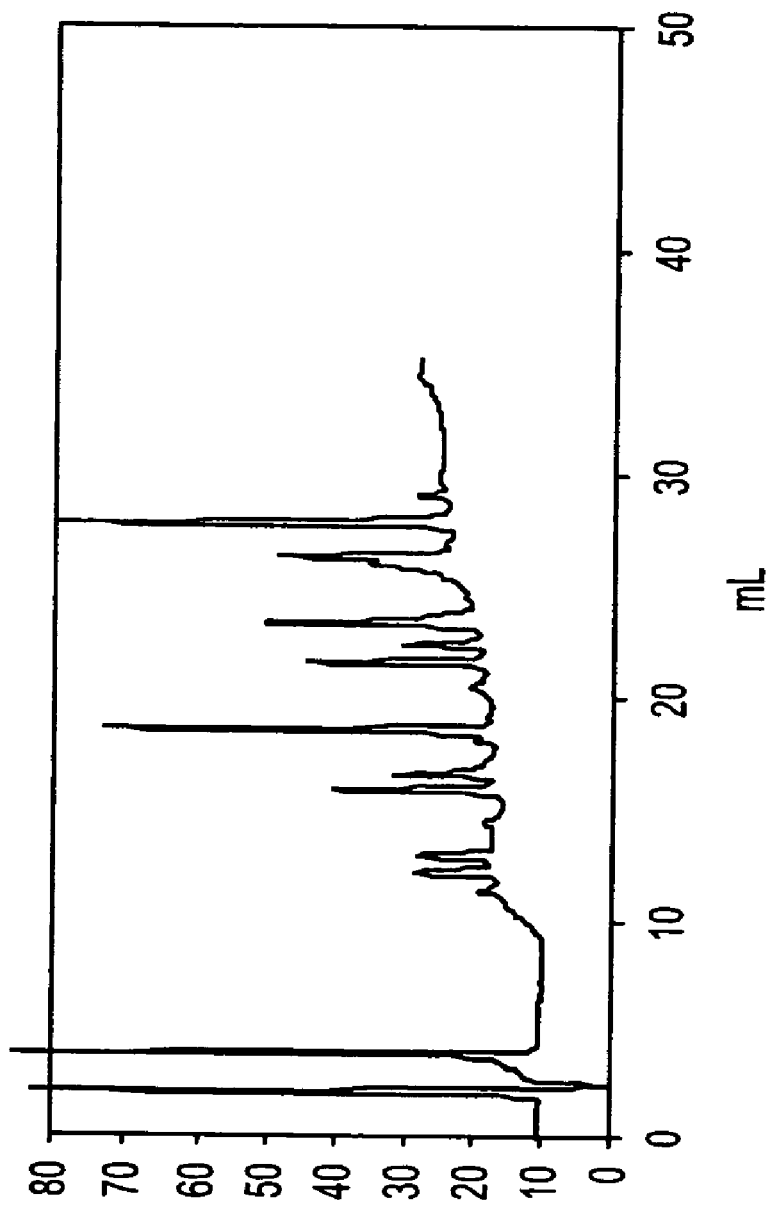
FIG. 35 presents a representative HPLC profile of cytochrome C, after protease digestion by covalently surface-coated trypsin. The capillary surface was modified by either aminoalkylsilane reagent or streptavidin modification.

For a given immobilized-trypsin cassette, three protein digestion reactions were performed over a period of two weeks. Fresh cytochrome C solutions were applied in each digestion reaction, and immobilized-trypsin capillary cassettes were stored in 0.15 M phosphate buffered saline at 4° C. between runs. Capillary electrophoresis separation obtained on MegaBACE™ demonstrated that all capillaries of these treated capillary cassettes have the same peptide maps across the three runs. Representative electropherograms of run1, run2 and run3 are shown in FIGS. 32, 33 and 34, respectively. On the contrary, the control capillary cassette showed some protein digestion only in the first run, but no protein digest in the second or the third run. As a result, such adsorbed enzymes do not have efficient capacity to carry out repeated digestion reactions. A high performance liquid chromatography (HPLC) was utilized to further characterize these protein digests. A representative HPLC chromatogram is shown in FIG. 35. The peptide profile of the protein digests obtained on covalently-coated capillary cassettes are in agreement with literature results (Neue et al., HPLC Columns: Theory, Technology, and Practice, VCH Publishing, 1997).

EXAMPLES

The following examples illustrate uses of the methods and apparatus of the present invention, and are representative of the many different types of biochemical or enzymatic reactions that can be effected with the disclosed methods. These reactions include 1) dye-primer DNA sequencing; 2) dye-terminator DNA sequencing; 3) PCR amplification; 4) PCR amplification, enzymatic purification, and DNA sequencing; and 5) enzymatic reactions. The following examples are offered by way of illustration and not by way of limitation.

Example 1

Dye-Primer DNA Sequencing Analyzed by Capillary Electrophoresis

Dye-primer sequencing reactions were performed within a capillary cassette comprised of 96 uncoated 2.8 cm long, 150 μm I.D., 360 μm O.D. fused-silica capillaries. Dye-primer sequencing reactions were performed by amplifying template DNA with emission-specific primers corresponding to ddT, ddA, ddC, and ddG terminated reactions. The amplification of template was performed as single reactions in each capillary and pooled into a common well for post-reaction processing and analysis.

The color-specific primers were based on the M13-40 FWD primer (5'-FAM-GTTTTCCCAGT*CACGACG-3') SEQ ID NO:2, with 5-carboxyfluorescein (FAM) as the donor dye, and a termination-specific fluor attached to the indicated thymine (T*) as the acceptor dye. The thymine was labeled with FAM for ddC-terminated reactions (C-FAM), 6-carboxyrhodamine for ddA reactions (A-REG), N,N,N',N'-tetramethyl-5-carboxyrhodamine for ddG reactions (G-TMR), and 5-carboxy-X-rhodamine for ddT reactions (T-ROX). A master mix for 100 dye-primer sequencing reactions was prepared by combining 65 μL reaction buffer (220 mM Tris-HCl, pH 9.5, 33.2 mM $MgCl_2$), 100 μL dye-primer solution (either 1 μM T-ROX, 1 μM G-TMR, 0.5 μM A-REG, or 0.5 μM C-FAM), 100 μL of the corresponding deoxy- and dideoxynucleotide mix (0.94 mM dATP, dCTP, dTTP, 7-deaza-dGTP, with 3.1 μM dideoxynucleotide), 10 μL of enzyme (32 units/μL ThermoSequenase), and 225 μL filtered demonized water. This solution was aliquoted into a 96-well reagent plate prior to mixing with template DNA. The general mixing scheme required the use of two capillary cassettes and a 384-well "mix plate." The first capillary cassette (transfer cassette) was dipped in a solution of template DNA (20 ng/μL M13mp18), and then inverted onto the top of a 384-well "mix plate" with the short ends of the capillaries inserted into the wells. The inverted transfer cassette and mix plate were placed inside a bench top centrifuge. A balance plate was added to balance the rotor and the centrifuge brought to 3,000×g for 5 seconds. The centrifugation uniformly dispensed the contents of the transfer cassette into individual wells of the 384-well plate. After the centrifuge step, the transfer cassette was transferred to the capillary cassette washer 410 for cleaning, and the mix plate was used for a subsequent centrifuge step for reagent addition.

To add reagents, a second capillary cassette (the reaction cassette), was dipped into the wells containing sequencing reagents (prepared as described in the preceding paragraph) and inverted over the same wells of the same 384-well plate. The reaction cassette and mix plate were placed in the centrifuge, spun at 3,000×g for 5 seconds, and removed from the centrifuge. At this point each well contained 500 nL of template DNA and 500 nL of sequencing reagents to form the final reaction mixture. The second capillary cassette (used to add reagents) was then dipped into the 1 μL mixture contained in the mix plate, filling the capillaries of the reaction cassette with 500 nL.

The capillary cassette was inserted into the internal chamber of an air-based thermal cycler, as described herein in FIGS. 7A–C, where the ends of the capillary segments are sealed by depressing the ends of the capillaries against deformable membranes 264a and 264b. After 30 cycles of 95° C. for 2 seconds, 55° C. for 2 second, and 72° C. for 60 seconds, the thermal cycler was opened, removing the ends of the capillaries from contact with the deformable membranes. The capillary cassette was removed and placed on top of a 96-well "pooling plate" with the short ends of the capillaries inserted into the wells. The capillary cassette and mix plate were placed into a centrifuge, with a balance plate. The reaction products were dispensed by centrifugal force (~2500×g) into a microtiter plate containing 40 μL of 80% isopropyl alcohol. After an initial reaction, the capillaries were washed as described herein. After the four dye-primer reactions had been performed in four individual capillary cassettes and the four sets products pooled into the wells of the 96 well pooling microtiter plate, the samples were subsequently centrifuged at 3000×g for 30 minutes. The alcohol was decanted by a gentle inverted spin, and the samples were resuspended in 5 μL of $ddH_2O$ for electrokinetic injection and analysis by MegaBACE™ capillary array electrophoresis.

Analysis of the DNA sequencing fragments was performed with MegaBACE™, a 96-capillary array electrophoresis instrument (Amersham Biosciences, Sunnyvale, Calif.) using scanning confocal laser-induced fluorescence detection. Separations were performed in 62 cm long, 75 μm I.D., 200 μm O.D. fused-silica capillaries with a working separation distance of 40 cm. Electroosmotic flow was reduced by Grignard coupling of a vinyl group to the capillary surface and acrylamide polymerization. The capillaries were filled with a fresh solution of 3% linear polyacrylamide (LPA) (MegaBACE™ Long Read Matrix, Amersham Life Sciences, Piscataway, N.J.) which was pumped through the capillaries under high pressure from the anode chamber to individual wells of a 96-well buffer plate contained in the cathode chamber. Each well was filled with 100 μL of Tris-TAPS running buffer (30 mM Tris, 100 mM TAPS, 1 mM EDTA, pH 8.0). The matrix was equilibrated for 20 minutes followed by pre-electrophoresis for 5 minutes at 180 V/cm. Prior to sample injection, the cathode capillary ends and electrodes were rinsed with double distilled water ($ddH_2O$) to remove residual LPA prior to sample injection.

DNA sequencing samples were electrokinetically injected at constant voltage from a 96-well microtiter plate according to the specified conditions; one preferred injection condition for 500 nL samples is 40 seconds of injection at an applied voltage of 2 kV. After injection, the capillary ends were rinsed with water, the buffer plate was placed in the cathode chamber, and the electrophoresis run was commenced. Separations were typically for 120 minutes at 8 kV. Computer controlled automation of the instrument and data collection was performed using LabBench software (Amersham Biosciences, Sunnyvale, Calif.). Specific injection and run conditions were tailored to the reaction mixture to be analyzed.

The reproducibility of the described method for submicroliter dye-primer cycle sequencing is shown in FIG. 9. This histogram shows the percent of samples in different read length bins and shows that the method is highly reproducible. Over 80 percent of the sequenced DNA inserts had read lengths over 600 bases. Overall, this plate of 96 samples yielded 55,000 high quality "Phred 20" bases, with an average read length of 605 bases.

Example 2

Dye-Primer DNA Sequencing Analyzed by a Capillary Electrophoresis Microchip

In another analysis example, dye-primer reactions performed in the same capillary cassette were analyzed by direct injection into a 16 channel microfabricated "chip-based" analyzer described in detail in S. Liu, H. Ren, Q. Gao, D. J. Roach, R. T. Loder Jr., T. M. Armstrong, Q. Mao, I. Blaga, D. L. Barker, and S. B. Jovanovich, Proc. Natl. Acad, Sci. USA, 5-00. The 16-channel chip is formed by bonding two glass wafers, the top wafer has 50 um deep by 100 um wide channels etched into it by standard microfabrication methods. The pattern etched has a combination of two 8-channel groups, each with a common anode reservoir Sixteen cathode reservoirs were evenly spaced at 4.5-mm intervals in a line, as were sixteen sample and sixteen waste reservoirs. The reservoirs were formed by the drilled access holes through the top etched wafer. Sixteen 250-μm long twin-T injectors were formed by the offset of channels from the sample and waste reservoirs joining the main separation channel. The distance between adjacent channels (center-to-center) was 600 μm in the detection region. The two alignment holes were used to align the chip to the detector.

In this example, a dye-primer reaction terminated by ddT was performed as described and dispensed into the sample wells of a microchip containing 1.5 μL of ddH$_2$O. Sample injection was performed by applying voltages of 50 and 10 volts respectively to the waste and cathode reservoirs, typically for 60 s, while the sample and anode reservoirs were grounded. Separations were carried out immediately after sample injection by applying 2,000 volts to the anode reservoir, 140 volts to sample and waste reservoirs, while grounding the cathode reservoir. The corresponding separation field strength was ca. 227 V/cm. The laser-induced fluorescence was collected, digitized, and processed into the electropherogram shown in FIG. 10. The electropherogram demonstrates microchip analysis of the reactions performed in the described capillary cassette system.

Example 3

Dye-Terminator Cycle Sequencing with Alcohol Precipitation Purification

Dye-terminator cycle sequencing was demonstrated using the capillary cassette system and alcohol precipitation for cleanup prior to capillary array electrophoresis. In this example, the sequencing reaction mix was prepared by mixing 400 μL of sequencing reagents (Dynamic ET terminator kit, Amersham Pharmacia Biotech, Part 81600) with 100 μL of 5 pmol/μL of M13-28 FWD primer (5'-TGT AAA ACG ACG GCC AGT-3') SEQ ID NO:3. The reaction mix was distributed in 5 μL aliquots to a 96-well "reagent" plate. Mixing of template DNA and sequencing reagents was performed in the same series of steps described in Example 1, using a transfer cassette was used to transfer 500 nL of DNA samples and a reaction cassette to transfer 500 nL of sequencing reagents from the reagent plate to the wells of the mix plate. This same reaction cassette was then filled by capillary action with the template/reagent mixture.

The capillary cassette was transferred to the air-based thermal cycler where the capillaries were sealed between the deformable membranes within the thermal cycler. Thermal cycling was achieved with 30 cycles of 95° C. for 2 seconds, 55° C. for 2 seconds, and 60° C. for 60 seconds. After the thermal cycling, the cassette was removed from the cycling chamber and the contents of the capillaries dispensed by centrifugal force (3000×g) into a 96-well plate containing 40 μL of 80% ethanol. The samples were centrifuged at 3000×g for 30 minutes. The alcohol was decanted by a gentle inverted spin, and the samples were resuspended in 5 μL of ddH$_2$O for electrokinetic injection and analysis by MegaBACE™ capillary array electrophoresis. The cleanup of dye-terminator reactions by alcohol precipitation, the reproducibility of the technique, and the application to "real-world" templates is represented as a histogram of percent success versus read length in FIG. 11. FIG. 11 demonstrates excellent read lengths and success rates with M13 subclone inserts prepared from a subclone library of a mouse bacterial artificial chromosome.

Example 4

Dye-Terminator Cycle Sequencing with Size-Exclusion Purification

In another example, dye-terminator reactions were performed in 500 nL capillaries as described in Example 3, and the reaction products dispensed into 15 μL of ddH$_2$O by centrifugal force. The 15 μL samples were transferred to a filter plate containing 45 μL of hydrated Sephadex G-50. The samples were centrifuged through the Sephadex matrix at 910×g for 5 minutes and the fluent collected in a clean 96-well injection plate. The samples were electrokinetically injected without further dehydration or processing into MegaBACE™. For 16 samples, an average read length of 650 bases was obtained demonstrating the compatibility of sub-microliter dye-terminator sequencing with size-exclusion purification.

Example 5

Pcr Amplification of Plasmid Insert DNA

The present technology uses the disclosed system for the PCR amplification of insert DNA (e.g. subclone inserts from a DNA library). The PCR reaction mixture was prepared by mixing 5 μL of 10 μM of M13-40 FWD primer (5' GTT TTC CCA GTC ACG AC 3') SEQ ID NO:4 and 5 μL of 10 μM –40 REV primer (5' GGA TAA CAA TTT CAC ACA GG 3') SEQ ID NO:5 with 25 μL of 10× GeneAmp buffer, 15 μL of 25 mM MgCl$_2$, 5 μL of AmpliTaq Gold, 2.5 μL of 1 mg/mL bovine serum albumin (BSA), and 67.5 μL of ddH$_2$O. This mix was aliquoted in equal volumes to sixteen 0.20 mL tubes.

The reaction was initiated by mixing template DNA with the PCR cocktail using the two-capillary cassette and mix-plate method described. The transfer cassette was dipped into the glycerol stock solutions of a subclone library and dispensed by centrifugal force into the wells of a 384-well plate. A second "reaction" cassette was used to transfer 500 nL of PCR cocktail to the same wells by centrifugal force. The capillaries of the reaction cassette were subsequently dipped into the combined mixture of template DNA and PCR reagents, filling the capillaries by capillary action. Amplification was effected by placing the capillaries into the cycling chamber and thermally cycling with an activation step of 95° C. for 12 minutes followed by 30 cycles of 64° C. for 4.5 minutes and 95° C. for 5 seconds.

The PCR products were analyzed by agarose gel electrophoresis and compared with the same subclones amplified by full volume (25 μL) reactions performed in 0.20 mL tubes. Nanoscale capillary cassette samples were dispensed into 4.5 μL of ddH$_2$O by centrifugal force. Equivalent volume aliquots of full volume reactions were transferred manually using a low volume pipettor. To each 5 μL sample, 1 μL of 6× loading dye was added and the sample quantitatively transferred to the wells of an agarose gel. Agarose gel electrophoresis was performed using a 0.7% agarose gel with 1× Tris-acetate-EDTA buffer, pH 8.0. Samples were separated for 40 minutes at 15 V/cm, stained with Sybr Green II (Molecular Probes, Eugene, Oreg.), and imaged using a two-dimensional fluorescence scanner (FluorImager, Amersham Biosciences, Sunnyvale, Calif.). The scanned gel image is shown in FIGS. 12A and 12B. It can be seen that samples prepared at full volume (FIG. 12A) and 500 nL volume (FIG. 12B) have the same molecular weight distribution. This example demonstrates nanoscale sample preparation can be used for PCR reactions and that the products can be analyzed by traditional macro-scale analysis methods such as agarose gel electrophoresis.

Example 6

PCR Amplification and Cycle-Sequencing

A preferred mode of preparing cycle sequencing samples using the present invention is to prepare nanoscale PCR samples in the capillary cassette and related instrumentation, perform macroscale ExoI/SAP reactions, and then perform the cycle sequencing in the capillary cassette and related instrumentation. Nanoscale PCR template preparation for DNA sequencing was demonstrated by performing PCR amplification from glycerol stock subclones. Glycerol stock subclones were PCR amplified in the capillary cassette and related hardware as described in Example 5. After PCR amplification, the contents of the capillaries were dispensed by centrifugation into the wells of a 96-well plate containing 4.5 µL of 7.5 mU of shrimp alkaline phosphatase (SAP) and 37.5 mU of exonuclease I (ExoI). The PCR products and ExoI/SAP solution were allowed to incubate at 37° C. for 5 minutes to digest the unincorporated primers and to dephosphorylate the unincorporated nucleotides. After an initial incubation, the enzymes were deactivated by heating the solution to 72° C. for 15 minutes.

The ExoI/SAP treated PCR products were aliquoted to a fresh 384-well mix plate with a transfer capillary cassette and centrifugal dispensing. An equal aliquot of dye-terminator sequencing reagents were added to the 500 nL of purified PCR products using another capillary cassette, the reaction cassette, and centrifugal dispensing. The capillaries of the reaction cassette were then filled by dipping the capillary cassette into the 1 µL reaction mixture. The template was amplified according to Example 3, dispensed into 40 µL of 80% ethanol and purified as described. Analysis of the sequencing reactions was performed by MegaBACE™ using electrokinetic injection. Portions of six base called sequencing electropherograms from subclone templates prepared by nanoscale PCR amplification from glycerol stock solutions and by nanoscale cycle sequencing are shown in FIG. 13. By performing PCR in a capillary cassette and subsequently transferring the reaction mixture to a microplate, the present system allows a simplified transition from nanoscale (less than 1 µL volumes) to greater than nanoscale reaction volumes. The present system also allows a simplified transition from macroscale (more than 1 µL volumes) to nanoscale reaction volumes, as shown by utilizing the Exo I/SAP reactions for cycle sequencing in the capillary cassette.

Example 7

Isothermal Enzyme Performed in Sub-Microliter Capillary Cassette

The use of the described system for performing enzyme reactions was demonstrated with a fluorogenic enzymatic assay of β-galactosidase hydrolysis of β-D-β-galactosidase to the fluorophore resorufin. The β-galactosidase catalyzed hydrolysis of resorufin-β-D-galactosidase (RBG) was performed within the capillaries of a 96-capillary cassette and in control full volume reactions in which β-Gal hydrolyzes RBG.

A stock solution of 35 µM RBG was prepared in 5 mL of buffer (100 mM Tris-HCL, 20 mM KCl, and 2 mM $MgCl_2$) to 5 mg of RBG, vortexing vigorously, and filtering the solution through a 0.40 micron filter and then adding an equal volume of buffer. A dilution curve of RBG was then prepared from the stock solution. To each 10 µL of RBG solution prepared in 0.20 mL tubes, 200 ug of β-galactosidase was added and after briefly mixing, filled into a capillary cassette by capillary action. The cassette was placed in air cycler and after 2 minutes at 37° C., the capillary cassette was removed and the contents centrifuged out of the capillaries into a 384-well scan plate containing 5 µL of 1 M sodium carbonate. The wells of the scan plate were subsequently filled with 50 µL of $ddH_2O$. In parallel, the 0.2 mL tubes were incubated at 37° C. for 2 minutes and the ful volume reactions stopped by adding 1 M sodium carbonate. A control aliquot from the enzyme reactions performed in the 0.20 mL tubes was added to the scan plate.

Solid-phase capture of the β-galactosidase was also demonstrated with this system by simply filling the cassette with a 20 µg/mL solution of β-galactosidase to bind to the capillary surface followed by removing the excess liquid and drying the cassette using the described cassette wash-manifold. After β-galactosidase binding the capillaries were filled with RBG solution by capillary action. The reaction was performed for 2 minutes at 37° C. and analyzed by dispensing into 1 M sodium carbonate, and diluting with water in the scan plate.

Once all three sets of reactions (full volume, capillary cassette, and capillary cassette with solid phase capture) had been added to the scan plate, the plate was read by a fluorescent plate reader (Typhoon, Amersham Biosciences, Sunnyvale, Calif.). The results of the standard curve performed in 0.2 mL tubes (tube rxn), a reaction performed in the capillary cassette without solid phase capture (capillary reaction), and in the capillary cassette with solid phase capture (capillary with binding reaction) are summaries in FIG. 14. FIG. 14 shows the expected signal versus substrate concentration for the tube reactions, and data points of signal for the pre-mixed enzyme reaction performed in the capillary cassette, and for the capillary-binding β-galactosidase assay.

This example serves to illustrate the compatibility of the described system for performing a range of general enzyme activity and inhibition assays. In addition, it demonstrates that solid phase capture can be applied to proteins and enzymes as well as DNA. Finally, it shows the described system can be applied to isothermal reactions.

Example 8

Template Purification

This example demonstrates the effectiveness with which the methods of the instant invention can be used to purify template DNA of contaminants that interfere with sequencing reactions and acquisition of high quality sequence data.

Figure 17A:
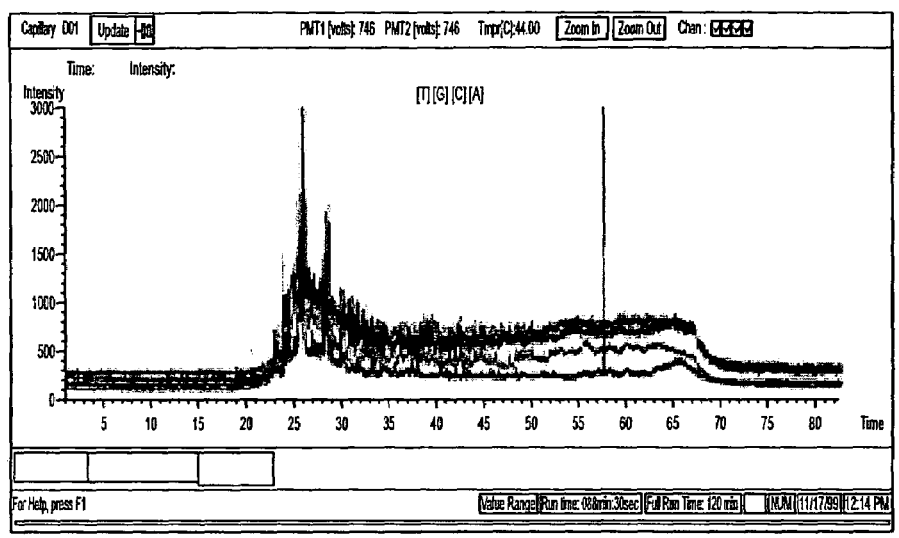
FIG. 17A shows the results of sequencing PCR products mixed with the reaction mixture prior to sequencing.
Figure 17B:
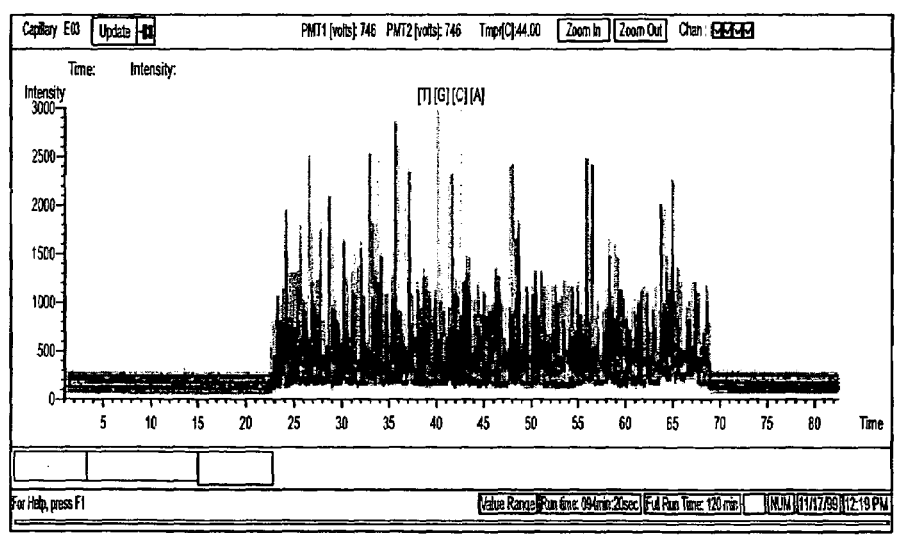
FIG. 17B shows the results of first mixing the PCR template with sodium thiocyanate, binding the DNA to the inner surface of the capillary, washing the DNA with 80% ethanol, followed by sequencing.

Template capture cleanup of PCR products as DNA sequencing template using direct reversible binding to the inner surface of a fused-silica capillary tube. A 500 nl volume sequence reaction, using the ET dye-terminator cycle sequencing method was carried out in a 150 µm inner diameter capillary tube and analyzed on MegaBACE™ using a 2 kv, 30 s injection. FIG. 17A shows the results of sequencing PCR products mixed with the reaction mixture prior to sequencing. FIG. 17B shows the results of first mixing the PCR template with sodium thiocyanate, binding the DNA to the inner surface of the capillary, washing the DNA with 80% ethanol, followed by sequencing.

Example 9

Template Normalization Effect for M13, Plasmid, and PCR Product DNA

This example, as do several of those following, demonstrates the usefulness and effectiveness of the methods of the present invention for normalizing the quantity of nucleic acid directly and reversibly immobilized inside capillary tubes.

Figure 18:
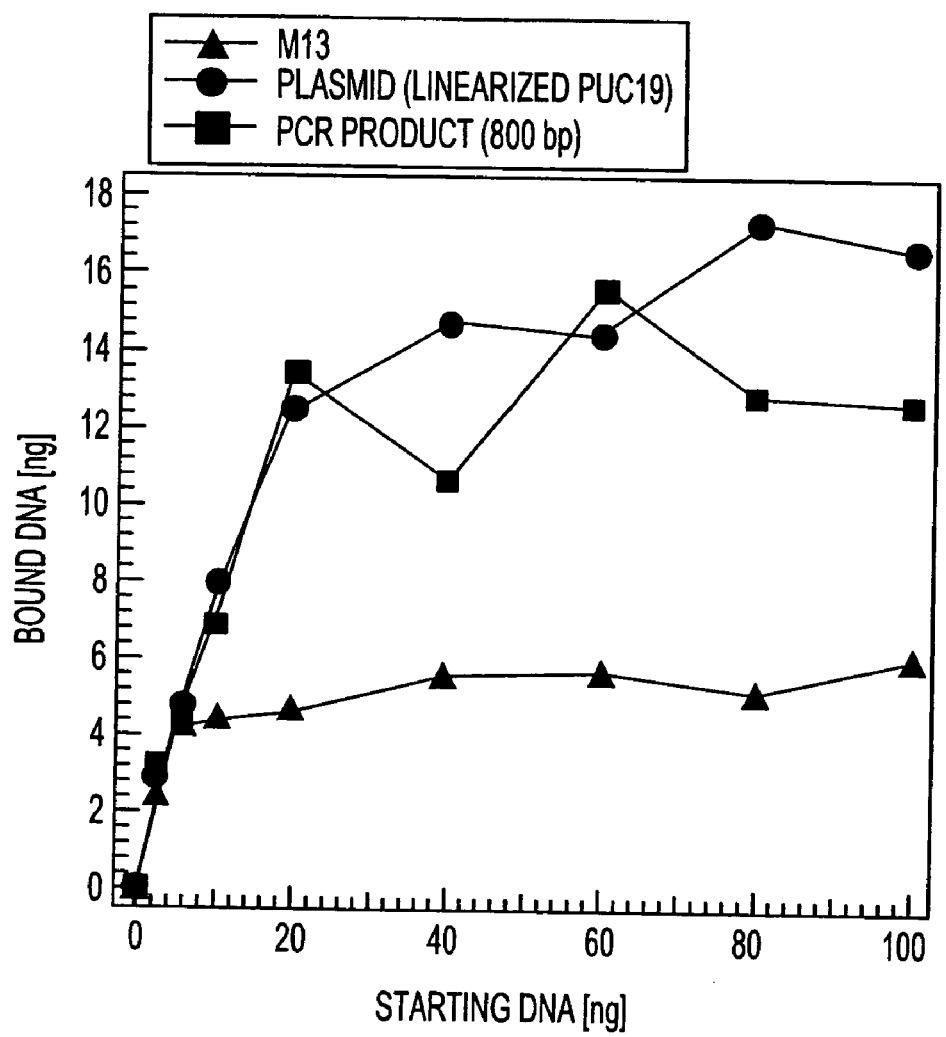
FIG. 18 represents the retained mass of DNA following a template capture protocol.

FIG. 18 represents the retained mass of DNA following a template capture protocol. The amount of DNA bound remains constant above 40 ng starting template for M13 (▲), plasmid (●), and PCR product (■).

Template DNA was prepared by a restriction digest of M13mp18 and PUC19 DNA to form linear single and linear double stranded DNA respectively. These templates, along with a 800 bp PCR product (standard amplification conditions) were end labeled with $^{32}P$ using [γ-32P]ATP and T4 polynucleotide kinase. The labeled DNA was seeded into unlabeled template of the same type and a calibration curve was generated for the seeded DNA solution. Template binding was performed by mixing stock DNA with 10 M sodium thiocyanate and loading into 500 nl fused-silica capillaries. After 10 minute incubation and 80% ethanol washing, the capillaries were placed in scintillation fluid and quantified. FIG. 18 shows definitive normalization for three sources of template DNA.

Example 10

Template Capture Normalization Effect on Read Length

Figure 19:
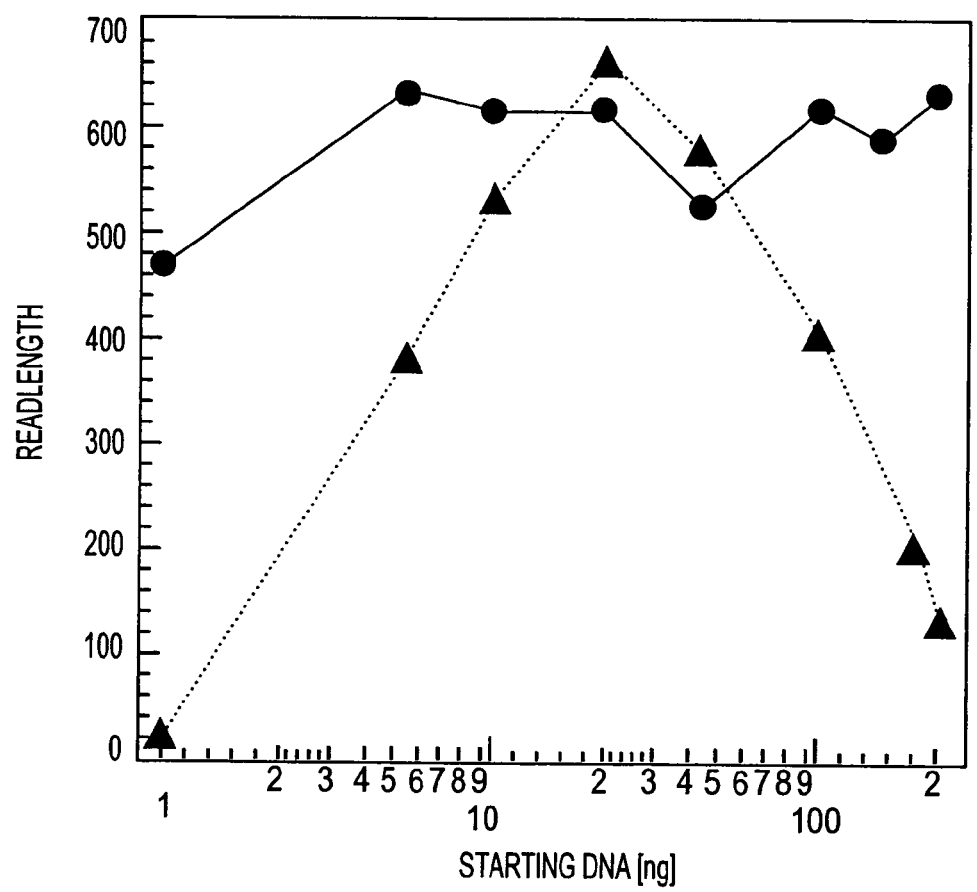
FIG. 19 shows a plot of read length versus starting DNA mass for samples prepared by premixing DNA and sequencing reagents (▲) compared to samples prepared by template capture (●)

FIG. 19 shows a plot of read length versus starting DNA mass for samples prepared by premixing DNA and sequencing reagents (▲) compared to samples prepared by template capture (●). The normalization effect is highlighted by a nearly constant read length obtained for the template capture samples, whereas for premixed samples, template overloading and reduction in read length occurs above 20 ng starting DNA.

Template binding was performed by mixing stock M13mp18 DNA with 10 M sodium thiocyanate and loading into 500 nL fused-silica capillaries. After 10 minute incubation and 80% ethanol washing, the capillaries were placed filled with ET terminator premixed with M13-40FWD sequencing primer. Premixed reagents were prepared in a 10 μl volume and loaded into clean sample preparation capillaries. The air-based cycle sequencing was performed as previously described followed by ethanol precipitation and MegaBACE™ analysis at 2 kV, 30 second injection, 8 kV, 120 minute run time.

Example 11

Template Capture Polymerase Chain Reaction with Normalization

Figure 20:
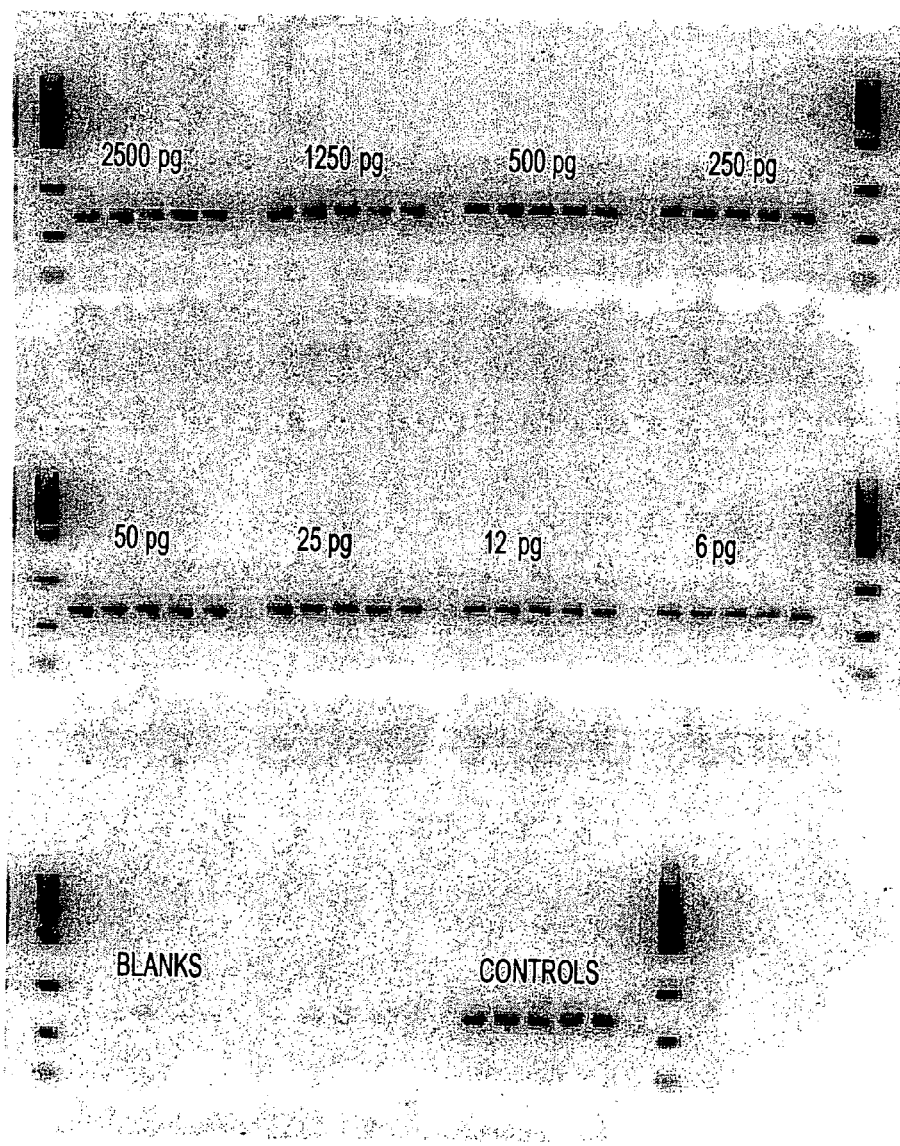
FIG. 20 shows products of PCR reactions after template binding of the indicated starting amount o M13mp18, electrophoresed through a 1.5% agarose gel, stained with SYBR Green dye and imaged with a Fluorimager apparatus.

PCR reactions were performed after template binding of indicated starting amount of M13mp18. Standard PCR amplification reactions with M13-100 FWD and M13-400 REV primers were performed in 500 nl capillary cassette with 10 s at 95° C., 10 s at 55° C., and 120 s at 72° C. Reaction products were dispensed by centrifuge into loading buffer, and transferred to a 1.5% agarose gel. The products were stained with SYBR Green dye and imaged with a Fluorimager apparatus, as shown in FIG. 20.

Example 12

Figure 21:
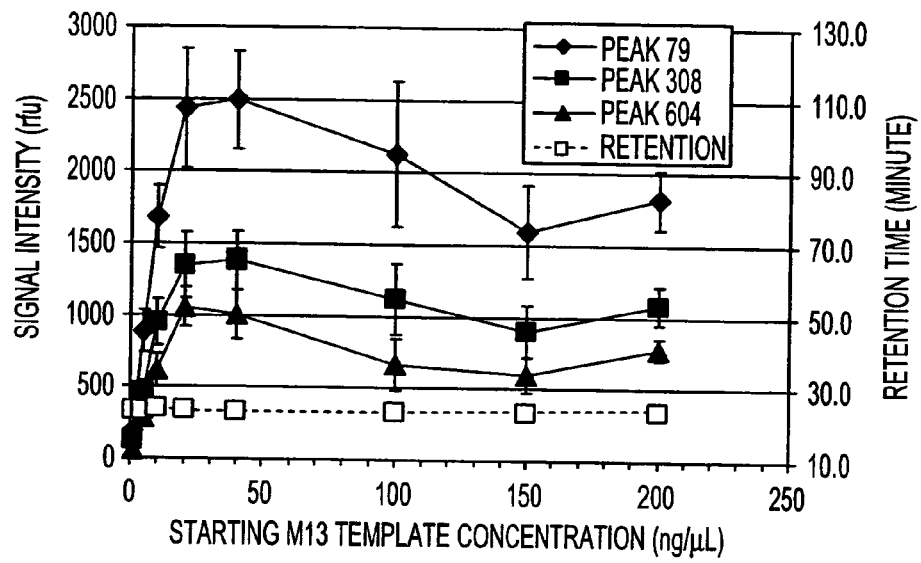
FIG. 21 represents the relative signal intensity obtained with increasing template concentration.

Template Capture Normalization Effect on Peak Height and Migration Time and Peak Height and Migration Time for Pre-Mixed Samples Template capture normalization effect on peak height and migration time. FIG. 21 represents the relative signal intensity obtained with increasing template concentration represented by the intensity of peak 79, peak 308, and peak 604 (ddT-terminated peaks early, middle, and late in the electrophoresis chromatogram). The peak intensity increases to 40 ng/μl and levels off, confirming by peak height the normalization effect and saturation level of the template capture technique. The migration time of the first peak is relatively constant across template concentrations.

Figure 22:
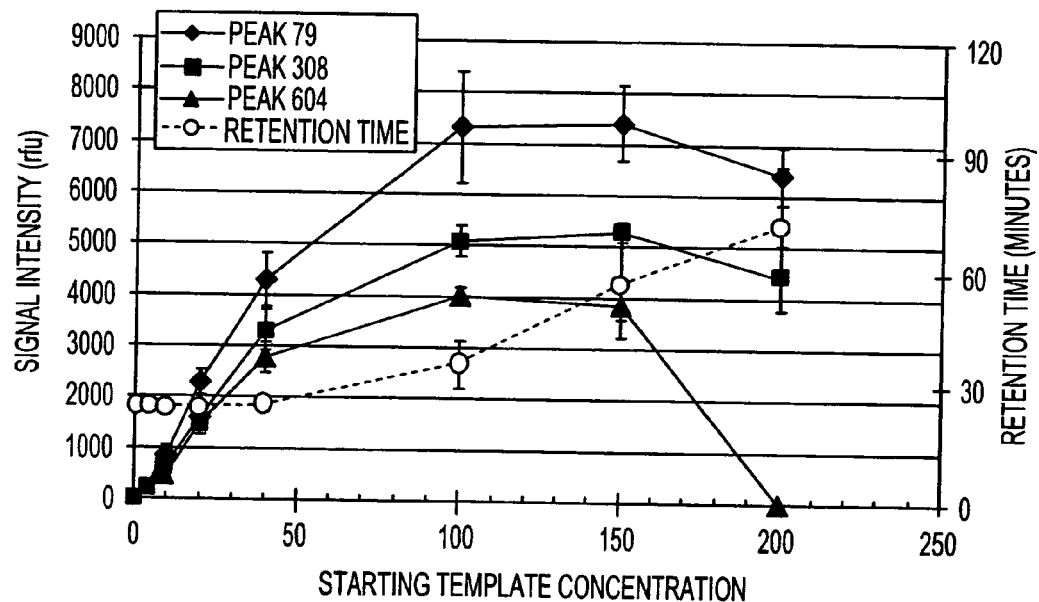
FIG. 22 represents the relative signal intensity obtained with increasing template concentration, showing peak height increasing with increasing template concentration.

Peak height and migration time for pre-mixed samples. FIG. 22 shows peak height increasing with increasing template concentration, reaching a maximum due to overloading of the sequencing sample. An excess of template DNA inhibited the electrokinetic injection, reducing the current in the sample run, consequently increasing the migration time of the sample through the capillary.

Example 13

Nanoscale Direct Cycle Sequencing from Glycerol Stocks of Clone

Figure 23A:
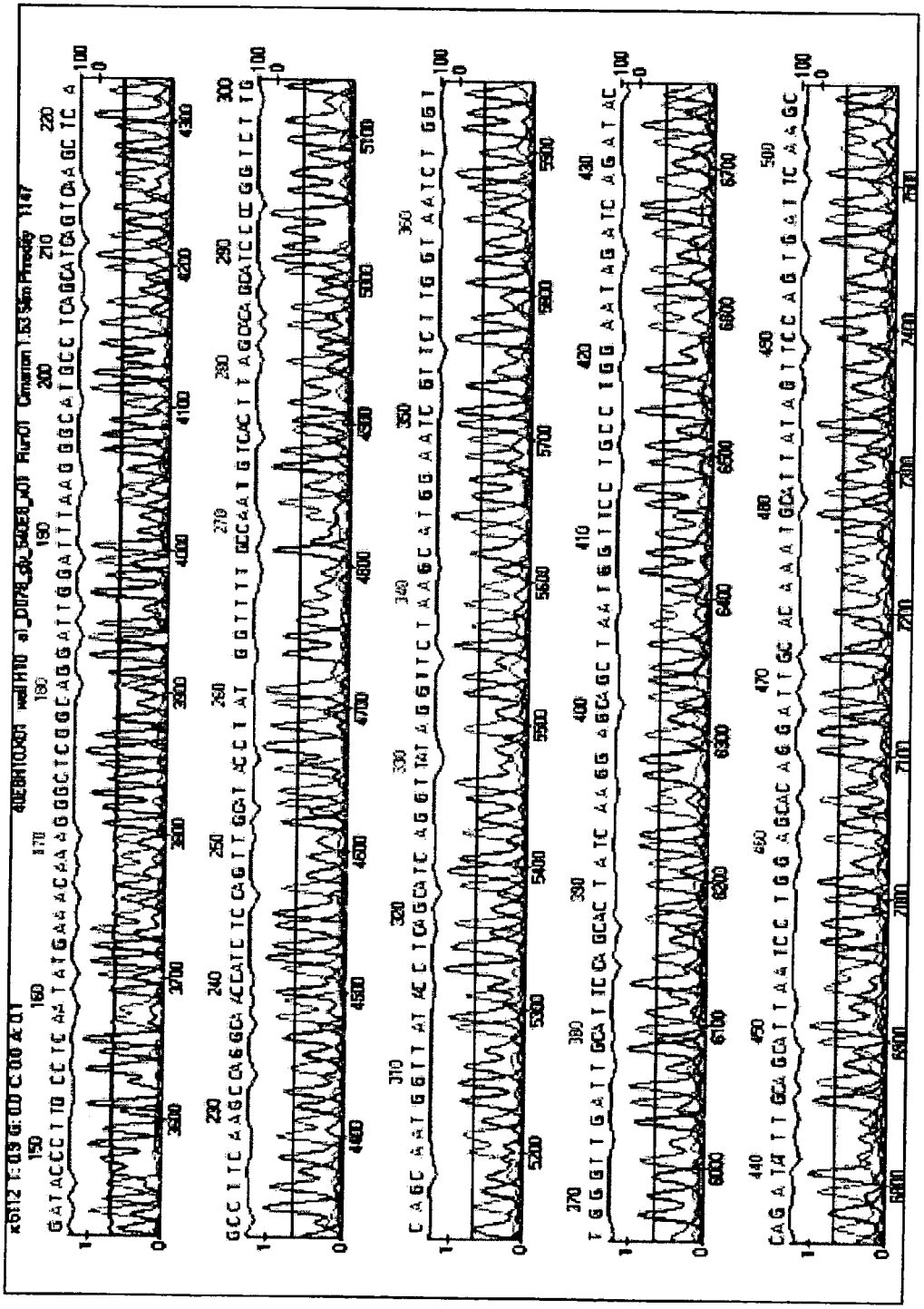
FIGS. 23A and 23B show a trace that had a Phred 20 score of 561 bases obtained by nanoscale direct cycle sequencing from glycerol stocks.
Figure 23B:
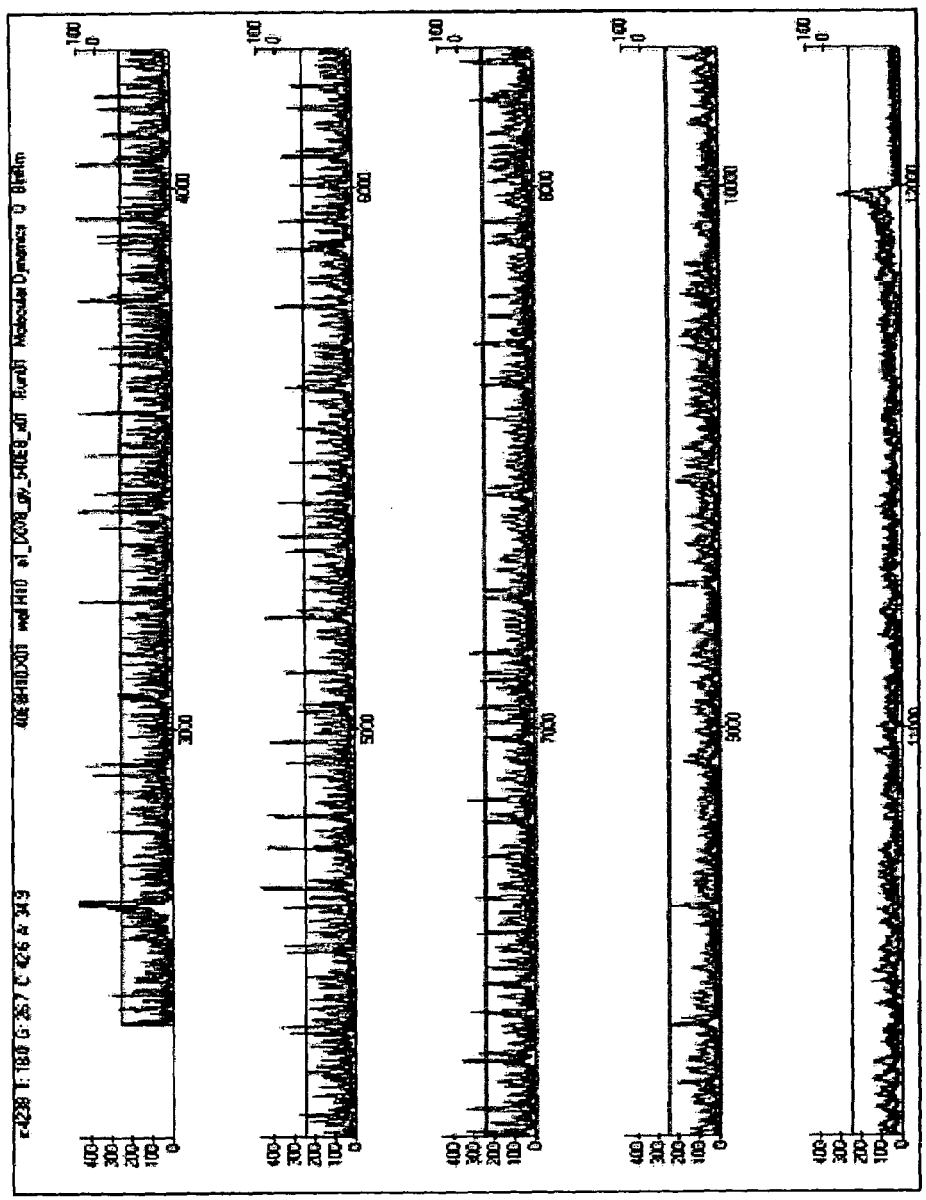

Sample preparation for DNA sequencing could be simplified if some of the many steps involved in preparing sequencing samples from cloned DNA in bacterial cells could be eliminated. Typically for capillary electrophoresis analysis, bacterial cells are grown and lysed, PCR amplification is performed, followed by ExoI/SAP cleanup and then cycle sequencing. The instant invention provides a method to simplify the workflow by cycle sequencing directly from glycerol stocks of clones. Equal volumes of glycerol stock and 10 M NaSCN were pulled into a 96 channel 500 nl capillary cassette. A five minute binding was performed at 60° C. in the air cycler disclosed in application U.S. Ser. No. 09/577,199, now U.S. Pat. No. 6,423,536, herein incorporated by reference in its entirety. The capillary cassette was washed with an 80% ethanol rinse and dried with flowing nitrogen in the capillary cassette washer disclosed in application U.S. Ser. No. 09/577,199, now U.S. Pat. No. 6,423, 536. The cassette was then filled by capillary action with a 1:4:5 mixture of primer, ET terminator premix and water and cycled in the air cycler. The cycling protocol was for ET terminators as described in Example 1, above. The samples were ethanol precipitated by being dispensed by centrifugation (3220 g for 30 minutes at 4° C.) into a microtiter plate containing 80% ethanol. After decanting and 30 seconds of inverted spinning at 50 g to remove ethanol, the samples were resuspended in 5 ul water. The samples were then injected into MegaBACE™ with a 2 kV, 30 second injection followed by a 8 kV, 140 minute separation. The data were analyzed with Sequence Analyzer software (Amersham Biosciences) and then processed to determine Phred 20 base calling scores. FIGS. 23A and B show a trace obtained by this method that had a Phred 20 score of 561 bases. This example demonstrates the application of the instant invention to direct sequencing from frozen glycerol stocks of bacteria. It will be apparent to the skilled artisan that this method can be applied to the sequencing of bacterial colonies grown on agar plates, or similar solid growth media, regardless whether the plates are fresh or desiccated.

Example 14

Genotyping with Nanoscale Single Base Extensions of Nucleic Acids

The instant invention can be applied to perform nanoscale genotyping reactions.

Single-base extension (SBE) reactions were performed in the 96 channel capillary cassette. The single base extension analysis consists of the single base extension of a DNA primer that terminates immediately before the base to be interrogated. PCR reactions of 25 ul were prepared containing 5 ng/ul of genomic human DNA, 1 μM of forward and reverse primers, buffer, $MgCl_2$ and AmpliTaq Gold. The PCR cycling was 96° C. for 12 min, 35 cycles of 94° C. for 20 sec, 60° C. for 20 sec, and 72° C. for 30 sec, followed by 72° C. for 2 min. An Exo I/SAP cleanup was performed by adding 9 units of SAP and 45 units of Exo I to the 25 μl of PCR products. The reaction was incubated at 37° C. for 45 min and then the ExoI/SAP enzymes denatured by heating to 95° C. for 15 min.

For full volume control reactions, 9 μl of SBE premix containing fluorescently labeled dideoxyterminators, a DNA polymerase, buffer solution and 1 μl of 2 μM primer was added to 10 μl of the ExoI/SAP treated PCR products. For reactions in the 500 nl capillary cassette, samples were loaded by capillary action.

The single base extension reactions were performed by 25 cycles of 96° C. for 10 sec, 50° C. for 5 sec, 60° C. for 30 sec. The thermal cycling was carried out in either MJ Research tetrads (a type of thermal cycling machine) for the full volume controls, or for the capillary cassette samples, in the air cycler disclosed in application U.S. Ser. No. 09/577,199, now U.S. Pat. No. 6,423,536, herein incorporated by reference in its entirety. The samples were dispensed into water and injected into MegaBACE™ for analysis.

Figure 24:
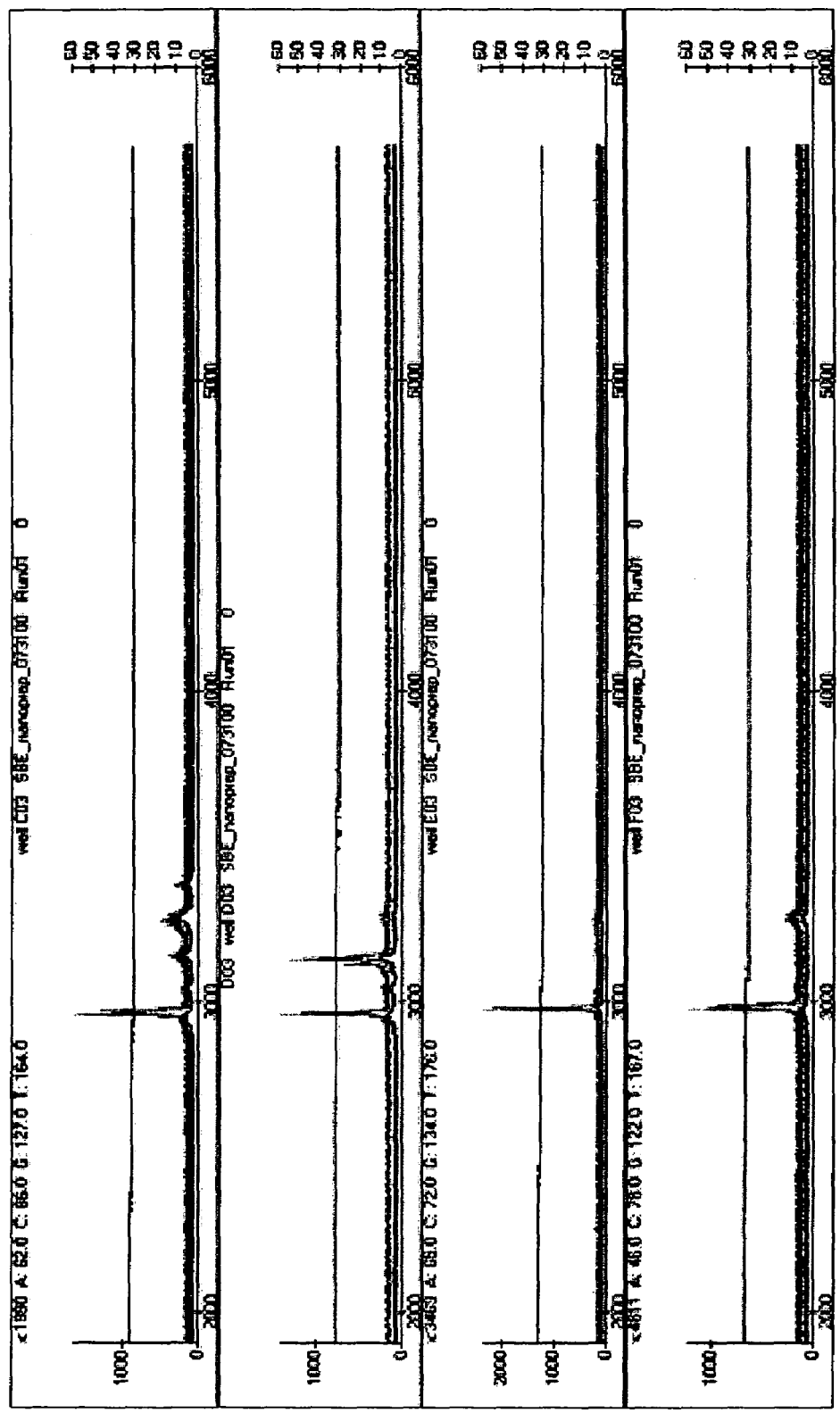
FIG. 24 are MegaBACE™ traces from four nanoscale single base extension reactions, without template capture, demonstrating heterozygosity in trace 2.

FIG. 24 demonstrates that the capillary-based reactions could correctly identify single nucleotide polymorphisms. Traces 1, 3, and 4 were obtained from samples homozygous at the interrogated base. Trace 2 was obtained from a sample heterozygous at the interrogated base and demonstrates that allelic polymorphism can be detected using nanoscale reactions. Signal is essentially the same as that obtained with the full volume reactions.

The entire process, from PCR to SBE, was accomplished using the capillary cassette.

Template capture in the capillary, as described in this application, is used in an improved version of this nanoscale single base extension reaction and provides even better results.

It will also be apparent to the skilled artisan that single base extension of messenger RNA using reverse transcriptase and fluorescently-labeled ribonucleotides permits genotyping using mRNA as an alternative to genomic DNA.

Example 15

Nanoscale Genotyping with Amplified Fragment Length Polymorphism

The methods of the instant invention can be used to perform AFLPs (amplified fragment length polymorphism) in nanoliter volumes. To perform AFLP reactions, genomic DNA is digested with pairs of restriction enzymes. The fragments are either ligated to a linker and amplified to amplify fragments of a certain length, in a certain orientation, as determined by the two restriction enzymes used, or alternatively, amplified by PCR directly using degenerate primers. The amplified fragments are analyzed by capillary electrophoresis. The AFLP analysis method is used to generate a "representation" of a genome, also called an amplicon, with variable fragments as well as constant ones. The amplicon is used to assess the diversity of populations of organisms or to make genome maps in organisms where little sequence and marker information is available.

Example 16

Nanoscale Genotyping with Direct Display Analysis

The methods of the present invention can be used to perform direct display analysis in nanoliter volumes. To perform direct display analysis reactions, complementary DNA is digested with pairs of restriction enzymes. The fragments are either ligated to a linker and amplified to amplify fragments of a certain length, in a certain orientation depending on the two restriction enzymes used, or alternatively, amplified by PCR directly using degenerate primers. The amplified fragments are analyzed by capillary electrophoresis. The direct display analysis method is used to generate a "representation" of a transcriptosome, with variable fragments as well as constant ones. Direct display analysis is used to assess the quantitative change in the level of expression between organisms, or differences due to environmental or physiological effects.

Example 17

Nanoscale Genotyping by Microsatellite Analysis

The methods of the present invention can be used to perform genotyping by microsatellite analysis in nanoliter volumes. To perform genotyping by microsatellite analysis reactions, genomic DNA is PCR amplified with marker panels such as PE Applied Biosystems Linkage Mapping Sets. For example, 96 human samples are analyzed with respect to panels of 12 genotypes in about 30 minutes using a four-color analysis. Three of the colors are used with four primer sets, while the fourth color provides internal size standards.

PCR set-up and thermocycling is performed as recommended by the manufacturer of the primer panel.

An example of a polymerase chain reaction mixture is as follows:

| Ingredient | Volume |
| --- | --- |
| 10X Gold Buffer | 1.50 μl |
| $MgCl_2$ (25 mM) | 1.50 μl |
| dNTPs Mix (2.5 mM) | 1.50 μl |
| Primer mix | 1.00 μl |
| AmpliTaq Gold | 0.12 μl |
| Sterile distilled water | 1.38 μl |
|  | 7.00 μl |
| DNA (5 ng/μl) | 8.00 μl |
|  | 15.0 μl per well |

The primer mix contains both forward and reverse primers, each at a final concentration of 5 μM.

An example of a thermal cycler program is as follows:

| Temp | Time | Cycle No. |
|---|---|---|
| 95° C. | 12 mins | 1 cycle |
| 94° C. | 15 sec | |
| 55° C. | 15 sec | |
| 72° C. | 30 sec | 10 cycles |
| 89° C. | 15 sec | |
| 55° C. | 15 sec | |
| 72° C. | 30 sec | 20 cycles |
| 72° C. | 10 mins | 1 cycle |

Pooling.

Sealed PCR sample trays are stored at −20° C.

Initially, 1 μl of each PCR product is pooled, after which the final volume is brought up to about 15 to 20 μl with water. Then, samples are dialyzed. Dialysis is done in 0.1X TE for 15 minutes, after which the pooled PCR samples are loaded into the MegaBACE™.

Loading.

Samples are prepared for loading into the MegaBACE™ as follows:

| Ingredient | Volume |
|---|---|
| Desalted PCR pools | 2.00 ul |
| ET400-R Size Standard | 0.25 ul |
| Formamide loading solution | 2.75 ul |
| Total loading volume | 5.00 ul |

Example 18

Nanoscale Enzymatic Reactions with Nucleic Acids

The present invention is advantageously applied to performing nanoscale enzymatic reactions with nucleic acids in nanoliter volumes. The nucleic acids are immobilized in a reaction chamber, such as a glass capillary, prepared according to the methods of the instant invention. The capillaries are filled with reaction mixtures that comprise one or more of different enzymes, such as a restriction enzyme.

A typical restriction enzyme digest is performed in a total volume of 20 μL that includes 0.2 to 1.5 μg of substrate DNA and a 2–10 fold excess of restriction enzyme over DNA. Reaction buffer, enzyme, water, and DNA are mixed in a reaction tube and incubated at 37° C. for 1 to 4 hours. According to the instant invention template DNA is bound to the inner surface of a capillary tube. Then, a premix of restriction enzyme (e.g. Hind III) in a 1× KGB buffer (100 mM potassium glutamate, 25 mM Tris-acetate, pH 7.5, 10 mM magnesium sulfate, 50 μg/ml bovine serum albumin, and 1 mM β-mercaptoethanol) is drawn into the capillary by capillary action. The reaction is incubated at 37° C. for an allotted time, after which the contents are dispensed in gel-loading buffer for agarose gel sizing, or into a solution containing 10 mM EDTA.

Other reactions comprising different enzymes are also possible. These enzymes include, but are not limited to methylation enzymes, DNA-dependent DNA polymerase enzymes, terminal transferase enzymes, RNA-dependent DNA polymerase enzymes, DNA-dependent RNA polymerase enzymes, phosphatase enzymes, kinase enzymes, exonuclease enzymes, such as S1, or mung bean nucleases, other nuclease enzymes, ribonuclease enzymes, or DNA or RNA ligase enzymes. For most of these reactions, control over the ratio of nucleic acid to enzyme is crucial to the success of the reaction process.

Use of the present application beneficially reduces the error associated with concentration dependent enzymatic reactions with nucleic acids, as well as reducing the consumption of valuable enzymes. Furthermore, through washing, use of the methods of the present invention is effective for eliminating residual ions, such as ammonium acetate, EDTA, and lithium chloride, and other contaminants, such as polysaccharides that interfere with enzymatic activity.

Example 19

Direct Sequencing from a Microarray Spotting Plate

To ensure the integrity of the data generated using microarrays, it is necessary that the identity of the sequence of the spotted DNA be known with high confidence. PCR is often used to generate the DNA to be spotted, and as is well known in the art, Taq and related thermostable polymerases introduces a certain number of erroneous base pairs per thousand as it amplifies the template. If errors have been introduced they must be detected, and the amplified product or data therefrom discarded. Usually, this requires numerous processing steps separate from those associated with spotting the PCR product. However, use of an embodiment of the present invention greatly increases the efficiency of sequence confirmation.

Confirmation of the sequence of a series of microarray spotting samples was achieved, using the methods of the present invention, as follows.

Microarray spotting samples were prepared from PCR products, average of 500 bp, from human genomic DNA template. The products were purified using standard guanidinium hydrochloride glass-filter plate processing and mixed with an equal volume of 10 M sodium thiocyanate. Samples were arrayed in a microtiter plate ("spotting plate") for subsequent spotting onto the microarray slide.

To confirm the PCR product sequence and positional arrangement on the microarray hybridization slide, sequencing reactions were performed by dipping the ends of a 96-capillary cassette into the spotting plate and binding the DNA to the inside surface of the capillary. After a wash step with 80% ethanol, the capillaries were filled with sequencing mix containing buffer, polymerase, dye-labeled dideoxynucleotides, and sequencing primer at 1× concentration. After thermal cycling (30 cycles at 95° C. for 5 s, 55° C. for 5 s, and 60° C. for 60 s), the sequencing reactions were purified by ethanol precipitation and analyzed by MegaBACE™.

In this example, 60 samples yielded confirmatory sequence, with an average read length of 335 bases (450 bp maximum). By directly sequencing from the same preparation and source as was spotted on the array, we resolved ambiguities in position or identity of the PCR product.

Example 20

Direct Sequencing of PCR Products without Preliminary Removal of PCR Nucleotides and Primers The methods of this invention have been used to simplify the purification of PCR products prior to sequencing. Typically, an enzymatic purification of the PCR product using exonuclease I (ExoI) and arctic shrimp alkaline phosphatase (SAP) to remove primer and excess dNTPs is required prior to cycle sequencing. Because template binding is size dependent, however, the unincorporated primers and remaining nucleotides can instead be removed from the template by differential binding of the template to the capillary, followed by removal of nucleotides and primer by washing. This approach obviates enzymatic cleanup of the PCR product and greatly simplifies the overall workflow.

As a demonstration, 96 PCR products of M13 DNA containing a mouse subclone insert were directly sequenced without enzymatic purification after PCR amplification.

The PCR amplification reactions were performed using M13 templates containing a subclone insert (ca. 2000 bp) of mouse genomic DNA. The M13 templates had previously been prepared by polyethylene glycol precipitation and detergent salvation (Thermomax), diluted 200 fold and rearrayed into a 96-well microtiter plate.

A 2 µL aliquot of this solution was transferred to a PCR amplification mix prepared with 2.5 µL 10× GeneAmp buffer, 0.2 µL of 25 mM each dNTPs, 0.5 µL of 10 µM M13-40FWD (GTT TTC CCA GTC ACG AC) SEQ ID NO:4, 0.5 µL of 10 µM M13-40REV primer (GGA TAA CAA TTT CAC ACA GG) SEQ ID NO:5, 1.5 µL of 25 mM magnesium chloride, 0.5 µL of 5 U/µL AmpliTaq polymerase, and 17.3 µL water. After mixing and sealing the plate, the reactions were thermally cycled at 95° C. for 10 s, 55° C. for 10 s, and 72° C. for 2 minutes for thirty cycles. After PCR amplification, a 5 µL aliquot was removed and mixed with 5 µL of 10 M sodium thiocyanate in a separate 96-well plate.

The capillaries of a 96-capillary cassette were dipped into the chaotrope-PCR product mixture, thus filling the cassette. After a 5 minute incubation at 60° C., the residual chaotrope, unbound buffer components and DNA were removed with an 80% ethanol wash applied by pulling the ethanol through the capillaries under vacuum. After drying the inside surface with a 1 minute flow of air, the capillaries were dipped into a sequencing mixture containing a 1× solution of ET terminator reaction mix and forward sequencing primer, M13-21FWD (TGT AAA ACG ACG GCC AGT) SEQ ID NO:3.

Cycle sequencing was performed by sealing the ends of the capillaries in the air-thermal cycle. The reaction was cycled 30 times at 95° C. for 5 s, 55° C. for 5 s, and 60° C. for 60 s. The cycle-sequencing products were dispensed into a microtiter plate containing 40 µL of 80% ethanol using centrifugal force. After a 30 minute centrifugation at 3000× g, the alcohol was decanted, the pelleted DNA resuspended in 5 µL of ddH2O, and the samples were analyzed by MegaBACE™.

For these 96 samples, an average read length of 550 bases was achieved with 83% pass rate and a sum of 44000 bases. This procedure has been repeated for over 5000 samples with demonstration of improvements over full-volume and enzymatically purified reactions.

Example 21

Comparison of Nanovolume and Full Volume PCR

PCR premixture is prepared by mixing template specific primer pairs with 10× GeneAmp buffer, MgCl2, AmpliTaq Gold, bovine serum albumin (BSA), dNTPs and double-distilled water. Fifteen microliters of the premix is then aliquoted into 24 wells of microtiter plate. To each well containing PCR premix, 10 ul of genomic DNA (5 ng/ul) is added as template for the reaction. Each of 23 wells receives genomic DNA isolated from a different individual, and one well receives no template as a negative control. For nanovolume PCR, the capillaries of a reaction cassette are filled by capillary action with about 500 nl of reaction mixture by dipping the ends of the capillaries into wells of the microtiter plate. The capillary cassette is then placed into the thermal air cycler, disclosed in application U.S. Ser. No. 09/577,199, now U.S. Pat. No. 6,423,536, herein incorporated by reference in its entirety, and the capillary ends are sealed. Amplification is then effected by air driven thermal cycling using the following program: 30 cycles of 93° C. for 10 sec; 60° C. for 10 sec, and 72° C. for 60 sec. For full volume PCR, the remaining PCR reaction mixture is transferred to 0.2 ml PCR tubes and amplification effected by thermal cycling using the following program: 35 cycles of 94° C. for 20 sec; 60° C. for 20 sec; 72° C. for 30 sec, and one cycle of 72° C. for 2 min.

After PCR is completed, the contents of the capillaries are expelled into 7.5 ul 1× loading dye by centrifugal force. An equivalent volume from each full volume PCR reaction is manually transferred using a low volume pipettor into the same amount of loading dye. PCR products are then loaded into the wells of a 1.5% agarose gel and subjected to electrophoresis for 40 minutes at 15 V/cm in 1×Tris-acetate-EDTA buffer at pH 8.0. After electrophoresis is completed, the gel is stained with the DNA dye Sybr Green II (Molecular Probes, Eugene, Oreg.), and is imaged using a two-dimensional fluorescence scanner (FluorImager, Amersham Biosciences, Sunnyvale, Calif.).

Figures 25A, 25B:
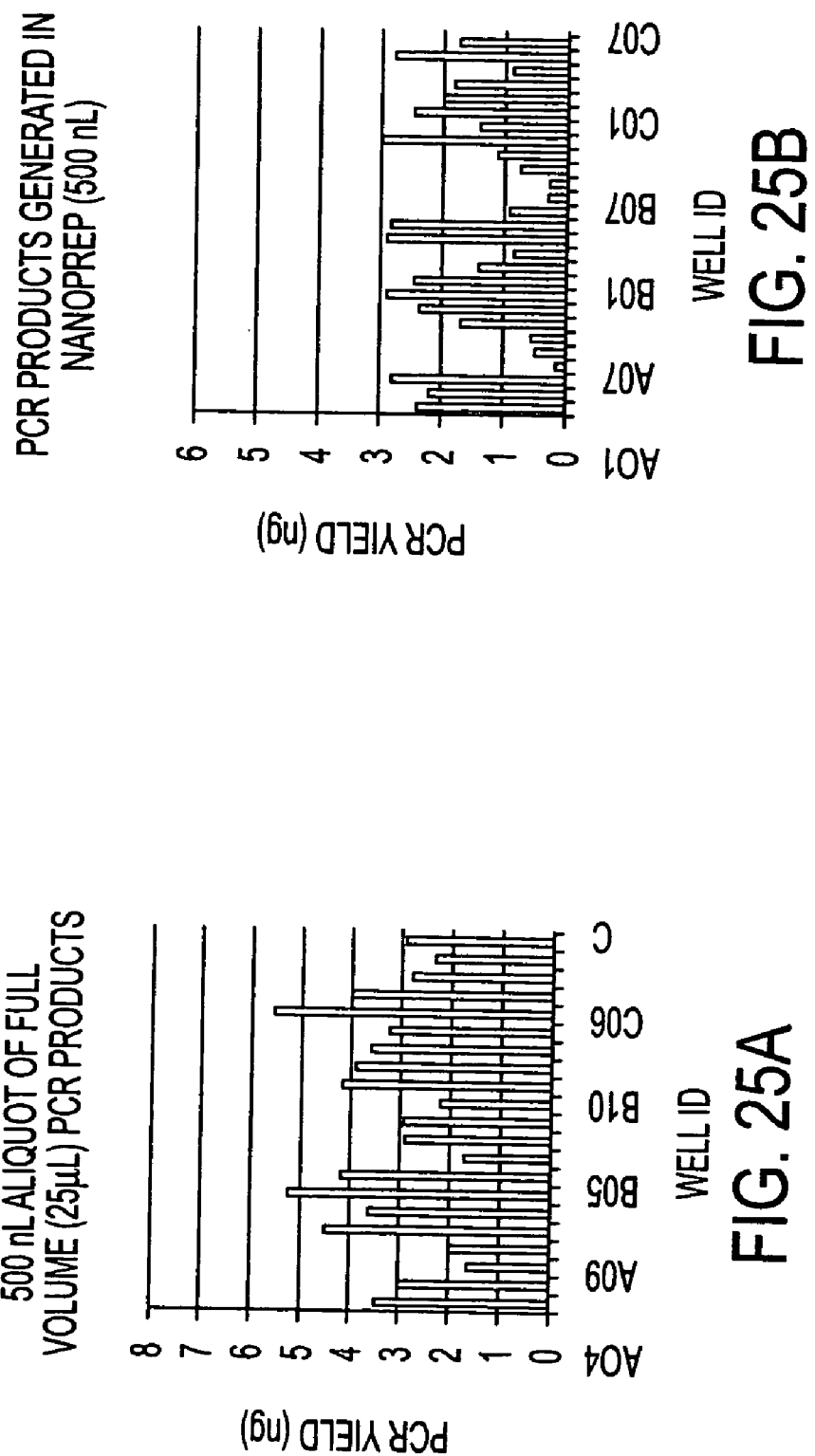
FIG. 25 shows the results of quantitative analysis of nanovolume PCR products (FIG. 25B) in comparison with that of full volume PCR products (FIG. 25A)

Fluorescence signal intensity from each band of PCR product is converted to DNA mass and displayed graphically. The results of this experiment are shown in FIG. 25, which demonstrates that PCR of genomic DNA in nanovolume reactions in capillary cassettes (FIG. 25A) yields a comparable amount of product as full volume PCR reactions (FIG. 25B).

Example 22

Comparison of Nanovolume and Full Volume SBE

Full volume and nanovolume SBE reactions are performed using PCR products generated from genomic DNA, which serve as the template for SBE. PCR is performed in full volume reactions as described in Example 21. After PCR is completed, excess PCR primers are digested with Exo I and unincorporated dNTPs are inactivated by treatment with SAP. To the 25 ul PCR volume is added and mixed 14 ul of ExoI/SAP solution (consisting of 9 ul of SAP at 1.0 U/ul and 5 ul of Exo I at 10 U/ul), after which the mixture is incubated at 37° C. for 45 min to effect the reactions, followed by 95° C. for 15 min to heat inactivate the enzymes.

For full volume SBE, to 10 µl of the ExoI/SAP treated PCR products are added 9 µl of SBE premix, and 1 µl of 2 µM SBE primer solution (primer NCBI 422 or primer NCBI 425) in the wells of a microtiter plate. SBE premix is similar to PCR premix, except that primer pairs are excluded and dNTPs are replaced with fluorescently labeled dideoxyterminators. After the ingredients are mixed, the reaction mixture is transferred to 0.2 ul tubes and SBE is performed by thermal cycling, as for PCR, using the following program: 25 cycles of 96° C. for 10 sec; 50° C. for 5 sec; 60° C. for 30 sec.

After full volume SBE is completed, unincorporated ddNTPs are dephosphorylated by CIAP treatment. Ten microliters of each SBE reaction product is transferred to the well of a microtiter plate and mixed with 25 ul of CIAP solution, containing 0.1 U/ul of CIAP and 1× CIAP buffer. The mixture is then incubated at 37° C. for 60 min to effect the reaction and then at 72° C. for 15 min to heat inactivate the CIAP enzyme.

Five microliters of each CIAP-treated full volume SBE reaction is then mixed with 5 uL of MegaBACE™ loading solution, denatured at 95° C. for 1 minute, and analyzed using MegaBACE™ (Injection: 6 kV for 15 sec. Run: 6 kV for 60 min).

Results from four samples analyzed by full volume SBE are shown in FIG. 26. FIG. 26A and FIG. 26C show heterozygous nucleotide polymorphisms at the interrogated base, whereas FIG. 26B shows a homozygous polymorphism. FIG. 26D shows that a negative control, which contained no DNA, produced no single nucleotide signal.

For nanovolume SBE, capillary tubes are dipped into the same SBE primer-premix solution reaction mixture prepared for full volume SBE, and filled by capillary action with about 500 nanoliters of the mixture. Thereafter, the capillary cassette is transferred to the air thermal cycler apparatus and SBE is performed, as for PCR, using the following program: 30 cycles of 95° C. for 5 sec; 55° C. for 5 sec; 60° C. for 30 sec.

After nanovolume SBE is completed, reaction products are expelled from the capillary tubes by centrifugation into the wells of a microtiter dish containing 20 ul of the CIAP solution described above. The reaction products are treated with CIAP by incubation at 37° C. for 60 min to effect the reaction and then at 72° C. for 15 min to heat inactivate the CIAP enzyme.

Five microliters of each CIAP-treated nanovolume SBE reaction is then mixed with 5 uL of water, and analyzed using MegaBACE™ (Injection: 2 kV for 45 sec. Run: 6 kV for 60 min).

FIG. 27 shows the results of an experiment comparing full volume (FIG. 27A) and nanovolume SBE (FIG. 27B) of the same heterozygous sample. The results demonstrate that nanovolume SBE produces similar quality data as full volume SBE.

Using both full volume and nanovolume SBE, 23 different samples were analyzed using two distinct primers (NCBI 422 and NCBI 425) with 100% accuracy of detection of the polymorphic nucleotide.

Example 23

Nanovolume SBE Coupled with Template Capture

Nanovolume PCR is performed similarly as described in Example 21, except that 5 ul of genomic DNA template are mixed with 7.5 ul PCR premix in the wells of a microtiter plate and then drawn into the capillary tubes by capillary action. After the reaction is completed, PCR product is expelled from the capillaries by centrifugation into the wells of a microtiter plate containing 500 nanoliters of 9.7M sodium thiocyanate (NaSCN). After mixing, about 500 nanoliters of the solution is drawn into new capillaries by capillary action, and incubated at 60° C. for 5 min to allow the SBE product to bind to the inner surface of the capillaries. Thereafter, the solution is expelled by centrifugation, the capillaries washed with 80% ethanol/20% double distilled water and dried with flowing nitrogen. Treatment of the nanovolume PCR product with ExoI/SAP is not performed.

Nanovolume SBE and CIAP treatment of the SBE products is then performed as described in Example 22, followed by analysis of the products using MegaBACE™, also as described.

FIG. 28 shows the results of an experiment comparing full volume PCR treated with ExoI/SAP, followed by full volume SBE (FIG. 28A) and nanovolume PCR with template capture, followed by nanovolume SBE (FIG. 28B) of the same heterozygous sample. The results demonstrate that nanovolume SBE coupled with template capture produces similar quality data as full volume SBE coupled with ExoI/SAP treatment of the PCR product that serves as SBE template.

Example 24

Comparison of SBE Product Cleanup Methods

Figure 29A:
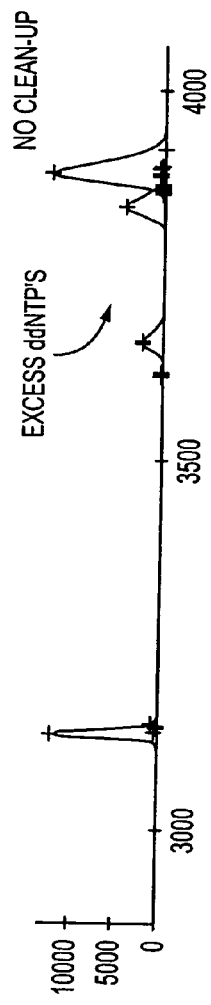
FIG. 29 presents the MegaBACE™ traces of (A) a nanovolume single base extension reaction, from nanovolume PCR and template capture of the PCR product, but with no subsequent cleanup of the SBE products; (B) a nanovolume SBE reaction with CIAP cleanup and injected into MegaBACE™ with MegaBACE™ loading solution; (C) a nanovolume SBE reaction with CIAP cleanup and injected into MegaBACE™ with deionized water; and (D) a nanovolume SBE reaction with Sephadex cleanup and injected into MegaBACE™ with deionized water.
Figure 29B:
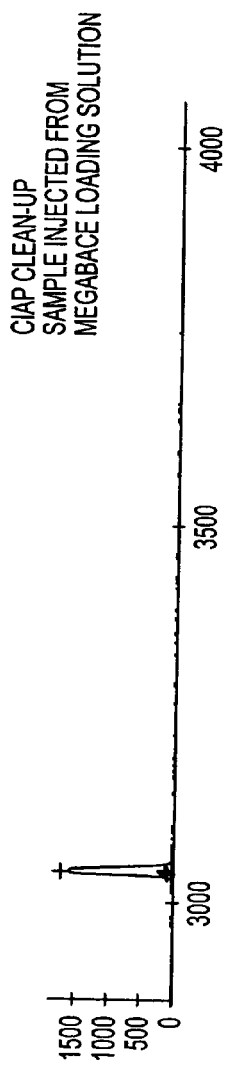
Figure 29C:
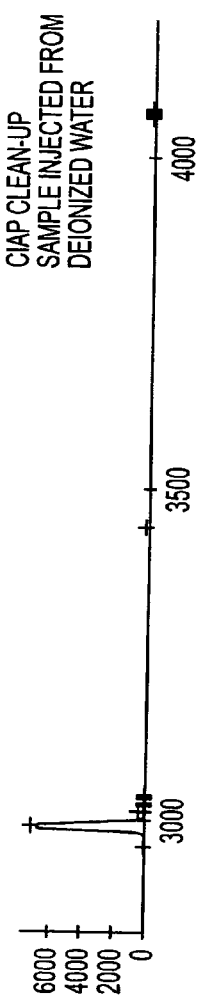

Nanovolume SBE is performed as described in Example 23 and different methods of treating the SBE products to remove or inactivate unincorporated ddNTPs prior to analysis using MegaBACE™ are compared for efficacy. Injection into MegaBACE™ is performed at 2 kV for 45 sec, and running of samples is performed at 6 kV for 60 min. As shown in FIG. 29A, if ddNTPs are not removed or inactivated prior to injection they produce a strong signal. FIG. 29B and FIG. 29C demonstrate the effectiveness of CIAP treatment in preventing the ddNTPs from entering the MegaBACE™ gel bed. Denaturation of SBE products in deionized water at 95° C. for 1 minute prior to injection results in about 4 fold greater signal intensity (FIG. 29C) as compared to denaturing the products in MegaBACE™ loading solution (FIG. 29B).

Figure 29D:
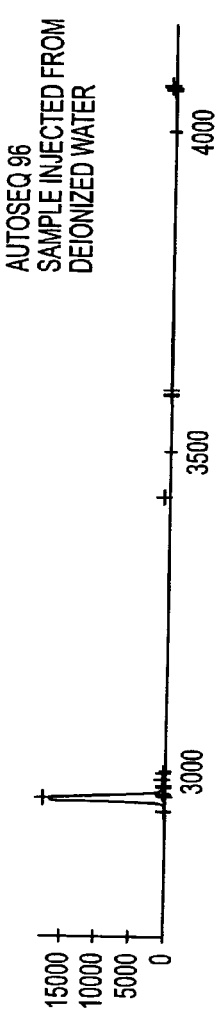

Most effective in removing ddNTPs and increasing signal intensity however, is purifying the SBE products using Sephadex (FIG. 29D) which results in a further 2 fold increase in signal intensity. Sephadex aliquoted into the wells of a microtiter plate is prewashed four times with 150 ul deionized water. Between washes, sephadex is pelleted in the well by centrifugation at 910 g for 5 min. Nanovolume SBE reactions are expelled by centrifugation into 20 ul of water, after which the diluted reactions are transferred to wells of the microtiter plate containing the sephadex. After incubation for time sufficient for ddNTPs to enter the pores of the sephadex, the sephadex is pelleted by centrifugation. A sample from each well is then injected directly into MegaBACE™.

Example 25

Validation of Nanovolume SBE

Nanovolume SBE is performed as described in Example 23 using 23 unrelated human genomic DNA samples, and 12 no-DNA negative controls. Different base positions are interrogated using 12 primers. SBE product is purified with sephadex as described in Example 24. Full volume SBE using the same samples and primers is performed as described in Example 22.

FIG. 30 compares the results of nanovolume and full volume SBE and shows the results for 9 of the primers. Average accuracy of nanovolume SBE (98%) is comparable to that of full volume SBE (99%).

The following examples demonstrate the usefulness and effectiveness of the methods of the present invention for performing a range of general enzyme activity and inhibition assays. In addition, they demonstrate that solid phase immobilization can be applied to proteins and enzymes as well as DNA. Finally, they show the described system can be applied to isothermal reactions. A multiplex capillary system used in the following examples contains 16, 96 or 384 capillaries.

Example 26

In Solution Protein Digestion Using Trypsin

The use of the described multiplex system for processing submicroliter protein-containing solutions was demonstrated with a trypsin digest of cytochrome C. The digestion was performed in homogeneous solutions within the capillaries of a capillary cassette.

A mixture of trypsin (Sigma, St. Louis, Mo.) and cytochrome C (Sigma, St. Louis, Mo.) were prepared with a tris-HCl buffer (10 mM, pH 8) at a trypsin-protein ratio of 1:10, 1:20, 1:50 and 1:100, and protein concentrations were kept at 1 mg/mL. 500 nL aliquots of the mixture were loaded into the capillary cassettes by capillary action, and incubated at 37° C. overnight. Digestion mixtures were then spun down (by centrifugation at 2700 G for 1 minute) to a 96-well Robbins plate of which each well contains fluorescein-5-isothiocyanate (FITC) (Molecular Probes, Eugene, Oreg.), 1 mg/mL in dimethyl sulfoxide. The plates were kept in dark at room temperature for 4 hours. The resulting mixtures were then diluted 20 to 2000 times with tris-HCl buffer, and subjected to capillary electrophoresis (CE) separation on MegaBACE™ 1000 (Amersham Biosciences, Piscataway, N.J.) using the MegaBACE LPA buffer and the long read matrix. Samples were injected at 1 KV for 5 sec, and separated at 9 KV for 50 min.

The above experimental conditions were run at least 16 times. A representative electropherogram of protein digest is illustrated in FIG. 31A. The obtained peptide profiles of digested cytochrome C are consistent and reproducible between each run and comparable to data obtained with full volume reactions.

Example 27

Protease Assay Using Endoproteinase Asp-N

Endoproteinase Asp-N digestion of polypeptides is illustrated here as an additional Example. It further demonstrates the use of the described multiplex system for processing submicroliter enzymatic reactions. An enzyme-product relationship for endoproteinase Asp-N digestion was established, as well as an optimal enzyme concentration.

Peptide Cy™5Q-YVADAPVK-Cy3 SEQ ID NO:1 (Amersham Biosciences, Piscataway, N.J.) was used as the reaction substrate. When the peptide is intact, Cy5Q efficiently quenches Cy3 and the excitation at Cy3 wavelength results in only a residual background signal. Once the peptide is cleaved (Asp-N cleaves the peptide at N-terminal side of aspartic acid residue), the dyes are no longer in close proximity, and excitation at Cy3 wavelength results in Cy3 emission. The signal intensity of Cy3 emission is in linear proportion to the amount of peptide being cleaved.

The endoproteinase Asp-N reaction was performed in homogeneous solutions. Five micrograms of the peptide was reconstituted with 20 uL dimethyl sulfoxide, then mixed with 980 uL of assay buffer (50 mM Tris, pH 8.0, +0.005% Tween 20™). The endoproteinase Asp-N (Amersham Biosciences, Piscataway, N.J.) was reconstituted with 500 uL glass distilled water, with a final concentration of 4 ug/mL. A series of dilutions were performed on the enzyme so that the final amount of Asp-N in a 500 nL reaction was between 5 and 180 picograms. Six concentrations of Asp-N were spun mixed with a 1:20 dilution of the peptide substrate in a 384 well microtiter plate. 500 nL aliquots of the mixture were loaded into a 384 capillary cassette system by capillary action, and incubated at room temperature for 10 minutes to allow reaction to complete. Digestion mixtures were then spun down into a 384-well clear plate (Nalge Nunc International, Rochester, N.Y.) of which each well contains 10 uL assay buffer. The plate was read by a fluorescent plate reader (Typhoon™, Amersham Biosciences, Piscataway, N.J.) at 532 nm and 650V with Cy3 555 BP 20 emission filter.

The reaction at each Asp-N concentration was repeated 24 times in parallel. FIG. 36 summarizes the result of these reactions. Signal intensity of Cy3 emission increases linearly as the Asp-N concentration increases, up to ~50 picogram Asp-N per 500 nL reaction. Beyond that, Cy3 signal intensity continues to increase—but at a slower pace—with the Asp-N concentration, up to 180 picogram per 500 nL reaction. The optimal amount of Asp-N in a 500 nL reaction volume is ~50 picogram. These results demonstrate the use of nanoprep for assaying potential drug targets in a high throughput nanoscale reaction and determining response curves. The application of nanoprep to high throughput drug screening will minimize the consumption of targets, compound libraries and natural product libraries.

Example 28

Protein Digestion with Trypsin Immobilized Beads

The use of the described multiplex system for processing submicroliter protein-containing solutions was demonstrated with a trypsin digest of cytochrome C. The digestion was performed with enzyme immobilized on magnetic beads within the capillaries of a capillary cassette. Introduction of small magnetic beads offers an efficient separation tool, and provides high binding surface area per unit volume for optimal accessibility of target molecules. As would readily be understood by those of skill in the art, beads can also be non-magnetic or scintillation proximity assay (Amersham Biosciences, Piscataway, N.J.), or have other surface properties.

Trypsin immobilized magnetic beads were prepared by incubating Streptavidin coated magnetic beads M280 (Dynal, Oslo, Norway) with biotin conjugated trypsin (Sigma, St. Louis, Mo.) in tris-HCl buffer at a bead-trypsin ratio of 10:1 (weight/weight). After 24 hours incubation under constant end-over-end shaking at room temperature, beads were cleaned on a Dynal MPC-96 magnet device by washing off unbound enzymes with tris buffer. These trypsin immobilized magnetic beads were then mixed with cytochrome C (Sigma, St. Louis, Mo.) at a bead-protein ratio of 10:1 (weight/weight). 500 nL aliquots of the mixture were then transferred to the capillary cassette by dipping the cassette into the bead solution with filling by capillary action. After incubation in an oven at 37° C. overnight, digestion mixtures were then spun down (by centrifugation at 2700 G for 1 minute) to a 96-well Robbins plate of which each well contains 1 mg/mL FITC labeling solutions. The mixtures were separated from beads by magnetic force, and the resulting supernatants which were free from beads were transferred to another plate. After reaction in the dark for 4 hours, the labeled protein fragments (peptides) were analyzed by MegaBACE™ 1000 (Amersham Biosciences, Piscataway, N.J.) as described in Example 26.

The above experimental conditions were run at least 16 times. Capillary electrophoresis characterization showed that the peptide profiles of digested cytochrome C obtained from this approach and the approach described in Example 26 are consistent and reproducible. A representative electropherogram of protein digest is illustrated in FIG. 31B.

Enzyme immobilized magnetic beads can also be applied to biochemical reactions where the substrate involves DNA or RNA molecules, proteins, glycoproteins, lipids, peptides, or other biomolecules in a capillary cassette format.

Example 29

Protein Digestion with Surface Modified Capillary Cassettes

Heterogeneous reactions using immobilized-enzyme reactors can eliminate the need for separating enzymes from the reaction mixtures, and minimize the contamination of the digest by the proteolytic enzymes. The current Example demonstrates that enzymes covalently bound to the inner surface of the capillary cassettes retain their activities and such a system can be used in enzymatic assays. As would be apparent to those skilled in the art, immobilized enzymes can also be used in many other reactions including sandwich assays, conversion of substrates to products, bioassays, or other reactions.

Silanization with aminoalkylsilane reagents gives an amino group functionalized surface to which a wide variety of affinity ligands can be subsequently attached. In this method, capillary cassettes (or other kind of reaction chambers) were treated by 3-aminopropyltriethoxy silane, followed by N-succinimidyl 3-(2-pyridyldithio) propionatel. The pyridyldithio functional group provides a convenient way to bind trypsin through specific —S—S— and —SH exchange reactions, and, if needed, the immobilized enzymes can be released by adding an excess amount of thiopyridone (Carlsson, J.; Drevin H.; Axen, R. Biochem. J. 1978, 173, 723). Thus, the same capillary surface can be regenerated for tethering fresh trypsin to ensure high enzyme reactivity.

Another surface immobilization approach is based on a specific streptavidin-biotin reaction. Streptavidin modification enables the surface to bind biotinylated enzymes. In this approach, capillary cassettes were derivatized with 3-aminopropyltriethoxy silane, and then reacted with a bifunctional linker, disuccinimidyl suberate, for tethering streptavidin that allows biotinylated trypsin to be thereafter linked to the capillary surfaces. The high specificity of streptavidin and biotin interaction was utilized to give uniformly oriented enzymes on the inner surfaces of the capillary (Wilchek, M.; Bayer, E. A. Methods in Enzymology, 1990, 184)

These two enzyme immobilization techniques are aimed to offer high surface reactivity and minimized nonspecific binding. As will be understood by the skilled artisan, other surface immobilization approaches can also be utilized. For example, reaction with γ-glycidoxylpropylsilane introduces oxirane groups to the solid surfaces that allow coupling enzyme at lysine sites. This modification is expected to provide more hydrophilic surfaces to reduce unspecific protein uptake. Conjugating enzyme with surface-active hydrogels offers a convenient means to produce enzyme immobilized surfaces (Caldwell, Carlsson and Li, U.S. Pat. No. 5,516,703, 1996). Advantage of this approach is to provide protein compatible environment and reusable surfaces.

Protein digestion reactions were conducted by directly introducing cytochrome C (1 mg/mL) to the streptavidin-biotin immobilized-trypsin capillary microreactors by capillary action, followed by incubation at 37° C. overnight. Protein fragments were then spun out, labeled with fluorescein-5-isothiocyanate (FITC), and the labeled protein digests subsequently subjected to MegaBACE™ analysis, all as described in Example 26. Two untreated capillary cassettes coated with trypsin (by simple adsorption) were used as the controls.

For a given immobilized-trypsin capillary cassette, three protein digestion reactions were performed during a period of two weeks using fresh cytochrome C solutions. The first reaction was performed on day 0, the second on day 7 and the third reaction on day 14. The immobilized-trypsin capillary cassettes were stored in 0.15 M phosphate buffered saline at 4° C. between runs. Capillary electrophoresis separation obtained on MegaBACE™ demonstrates that all capillaries of the treated cassettes have the same peptide maps in the three runs, as shown in the representative electropherograms of run1 (day 0), run2 (day 7) and run3 (day 14) (FIGS. 32, 33 and 34), respectively. On the contrary, the control capillary cassette showed some protein digestion only in the first run, but no protein digestion in the second or the third run. This is as expected, since nonspecific binding via physical adsorption probably reduces enzyme activity, and the binding is not as stable as covalent binding. As a result, such immobilized enzymes do not have sufficient capacity to carry out repeated digestion reactions. This example demonstrates that enzymes may be coupled to the surface of a high throughput nanoscale reactor and used to perform repeated enzymatic reactions, e.g., a proteolytic digestion, as described hereabove.

In addition to CE technique described above, high performance liquid chromatography (HPLC) was utilized to further characterize these protein digests. Experiments were performed on a ÄKTAexplorer chromatography system 10 with a fraction collector Frac-950 and an autosampler A900 (Amersham Biosciences, Piscataway, N.J.). A tryptic digest sample of cytochrome C prepared on the streptavidin-biotin immobilized trypsin capillary cassette was injected into a reversed phase column SOURCE 5RPC ST 4.6/150 (Amersham Biosciences, Piscataway, N.J.), and eluted out by a gradient (eluent A: 0.05% trifluoroacetic acid in 2% acetonitrile; eluent B: 0.05% trifluoroacetic acid in 80% acetonitrile). A representative HPLC chromatogram is shown in FIG. 35. The profile of cytochrome C digests obtained on capillary cassettes is identical to literature results (Neue, U. D.; Zoubair, M.; Fallah El, HPLC Columns: Theory, Technology, and Practice, VCH Publishing, 1997).

All patents, patent publications, and other published references mentioned herein are hereby incorporated by reference in their entireties as if each had been individually and specifically incorporated by reference herein. While preferred illustrative embodiments of the present invention are described, one skilled in the art will appreciate that the present invention can be practiced by other than the described embodiments, which are presented for purposes of illustration only and not by way of limitation. The present invention is limited only by the paragraphs that follow.

What is claimed is:

1. A method of performing an enzymatic reaction in a capillary tube using a normalized quantity of a nucleic acid, comprising:

saturably binding a nucleic acid from an excess thereof directly on an inner surface of said capillary tube by contacting said inner surface with a solution comprising said nucleic acid and a chaotropic agent for a time sufficient for the nucleic acid to become saturably bound to said inner surface;

removing unbound excess of the nucleic acid therefore generating a normalized quantity of said nucleic acid;

introducing an enzymatic reaction mixture into said capillary tube having said normalized quantity of said nucleic acid;

wherein said reaction mixture comprises an oligonucleotide primer, a DNA polymerase, dNPTs, and at least one dideoxynucleotide triphosphate (ddNTP), performing said enzymatic reaction in said capillary tube using said normalized quantity of said nucleic acid.

2. The method of claim 1, further comprising subjecting said enzymatic reaction mixture to at least one thermal cycle.

3. The method of claim 1, further comprising, after said step of removing said excess of the nucleic acid, a step of washing said inner surface of said capillary tube.

4. The method of claim 3, further comprising, after said step of washing said inner surface of said capillary tube, a step of drying said inner surface of said capillary tube.

5. The method of claim 1, wherein said enzymatic reaction mixture is introduced into said capillary tube by capillary action.

6. The method of claim 1, further comprising, after said step of performing said enzymatic reaction, a step of expelling the product of said enzymatic reaction.

7. The method of claim 1, further comprising, after said step of performing said enzymatic reaction, a step of removing unincorporated dideoxynucleotide triphosphates (ddNTPs).

8. The method of claim 7, wherein said unincorporated ddNTPs are removed by contacting the product of said enzymatic reaction with gel filtration media.

9. The method of claim 1, further comprising, after said step of performing said enzymatic reaction, a step of inactivating unincorporated dideoxynucleotide triphosphates (ddNTPs).

10. The method of claim 9, wherein said unincorporated ddNTPs are inactivated by treating the product of said enzymatic reaction with calf intestinal alkaline phosphatase (CIAP).

11. The method of claim 1, wherein the dideoxynucleotide triphosphates (ddNTPs) included in said enzymatic reaction mixture are selected from the group consisting of ddATP only; ddCTP only; ddGTP only; ddTTP only; ddATP and ddCTP; ddATP and ddGTP; ddATP and ddTTP; ddCTP and ddGTP; ddCTP and ddTTP; ddGTP and ddTTP; ddATP, ddCTP, and ddGTP; ddATP, ddCTP, and ddTTP; ddATP, ddGTP, and ddTTP; ddCTP, ddGTP, and ddTTP; and ddATP, ddGTP, ddCTP, and ddTTP.

12. The method of claim 1, wherein said dideoxynucleotide triphosphate (ddNTP) is conjugated to a fluorophore.

13. The method of claim 12, wherein said fluorophore is base-specific.

14. The method of claim 12, wherein said fluorophore is selected from the group consisting of: fluorescein, 5-carboxy-fluorescein, 6-carboxy-rhodnmine, N,N,N',N'-tetramethyl-5-crboxyrhodamine, 5-carboxy-x-rhodamine, rhodamine 110, rhodamine-6-G, tetramethyl rhodamine and rhodamine X.

15. The method of claim 12, wherein said fluorophore is an energy-transfer fluorophore.

16. The method of claim 1, further comprising analyzing a product of said enzymatic reaction to determine the identity of a ddNTP incorporated at the 3'-end of the primer.

17. The method of claim 16, wherein said step of analyzing a product of said enzymatic reaction to determine the identity of a ddNTP present in said nucleic acid is effected using a technique or an apparatus selected from the group consisting of gel electrophoresis, capillary electrophoresis, mass spectroscopy, MALDI mass spectroscopy, SELDI mass spectroscopy, fluorescence emission detection, scanning confocal laser-induced fluorescence detection, fluorescence polarization (FP) and analytical microchip analysis.

18. The method of claim 16, further comprising inferring the identity of said ddNTP incorporated at the 3'-end of said primer from the emission spectrum of a fluorophore conjugated to said ddNTP.

19. The method of claim 18, further comprising inferring the identity of a nucleotide present in said nucleic acid from the identity of said ddNTP incorporated at the 3'-end of said primer.

20. The method of claim 19, wherein the identity of said nucleotide present in said nucleic acid defines a single nucleotide polymorphism (SNP) in said nucleic acid.

21. The method of claim 20, wherein the identity of said nucleotide is stored as data in a computer data structure.

22. The method of claim 21, wherein said computer data structure is embodied in a computer readable medium.

23. The method of claim 1, wherein said DNA polymerase is thermostable.

24. The method of claim 1, wherein said DNA polymerase is a DNA-dependent DNA polymerase.

25. The method of claim 1, wherein said DNA polymerase is an RNA-dependent DNA polymerase.

26. The method of claim 1, wherein said nucleic acid is selected from the group consisting of: DNA, double stranded DNA, single stranded DNA, DNA produced by polymerase chain reaction, DNA produced by reverse transcription reaction, DNA isolated from an eukaryotic cell, DNA isolated from a prokaryotic cell, DNA isolated from an archaea cell, DNA isolated from a fungal cell, DNA isolated from a plant cell, DNA isolated from a virus, DNA isolated from a bacteriophage, genomic DNA, plasmid DNA, episomal DNA, RNA, messenger RNA, double stranded RNA, single stranded RNA, RNA isolated from an eukaryotic cell, RNA isolated from a prokaryotic cell, RNA isolated from an archaea cell, RNA isolated from a fungal cell, RINA isolated from a plant cell, RNA isolated from a virus, DNA-RNA hybrid, nucleic acid obtained from frozen glycerol stocks of bacteria and nucleic acid obtained from bacterial colonies grown on solid growth media.

27. The method of claim 1, wherein said nucleic acid is DNA; and further comprising the step of preparing said DNA by polymerase chain reaction (PCR).

28. The method of claim 27, wherein said nucleic acid is genomic DNA.

29. The method of claim 27, further comprising, after said step of preparing said DNA by PCR, a step of removing unincorporated PCR primer using a DNase which can cut single stranded DNA.

30. The method of claim 27, further comprising, after said step of preparing said DNA by PCR, a step of removing unincorporated dNTPs using a phosphatase.

31. The method of claim 27, further comprising, after said step of preparing said DNA by PCR, a step of treating said DNA with Exonuclease 1 (ExoI) and shrimp alkaline phosphatase (SAP).

32. The method of claim 1, further comprising, after said step of saturably binding said nucleic acid from the excess thereof directly on said inner surface of said capillary tube and removing said unbound excess of the nucleic acid therefrom, a step of removing unincorporated PCR primer and dNTPs by washing said inner surface of said capillary.

33. The method of claim 1, wherein said enzymatic reaction is performed in a reaction volume of about 10–5000 nanoliters.

34. The method of claim 1, wherein said capillary tube is present in a spatially addressable array of capillary tubes.

35. The method of claim 34, wherein said spatially addressable array of capillary tubes is an array having a number of capillaries selected from the group consisting of: 2, 4, 8, 12, 16, 24, 32, 48, 64, 96, 128, 192, 288, 384, 480, 576, 672, 768, 864, 960 and 1536 capillaries.

* * * * *

SEQUENCE LISTING

<160> NUMBER OF SEQ ID NOS: 5

<210> SEQ ID NO 1
<211> LENGTH: 8
<212> TYPE: PRT
<213> ORGANISM: ARTIFICIAL SEQUENCE
<220> FEATURE:
<223> OTHER INFORMATION: SYNTHETIC POLYPEPTIDE

<400> SEQUENCE: 1

Tyr Val Ala Asp Ala Pro Val Lys
1               5

<210> SEQ ID NO 2
<211> LENGTH: 18
<212> TYPE: DNA
<213> ORGANISM: ARTIFICIAL SEQUENCE
<220> FEATURE:
<223> OTHER INFORMATION: SYNTHETIC NUCLEOTIDE

<400> SEQUENCE: 2
gttttcccag tcacgacg                                                 18

<210> SEQ ID NO 3
<211> LENGTH: 18
<212> TYPE: DNA
<213> ORGANISM: ARTIFICIAL SEQUENCE
<220> FEATURE:
<223> OTHER INFORMATION: SYNTHETIC NUCLEOTIDE

<400> SEQUENCE: 3
tgtaaaacga cggccagt                                                 18

<210> SEQ ID NO 4
<211> LENGTH: 17
<212> TYPE: DNA
<213> ORGANISM: ARTIFICIAL SEQUENCE
<220> FEATURE:
<223> OTHER INFORMATION: SYNTHETIC NUCLEOTIDE

<400> SEQUENCE: 4
gttttcccag tcacgac                                                  17

<210> SEQ ID NO 5
<211> LENGTH: 20
<212> TYPE: DNA
<213> ORGANISM: ARTIFICIAL SEQUENCE
<220> FEATURE:
<223> OTHER INFORMATION: SYNTHETIC NUCLEOTIDE

<400> SEQUENCE: 5
ggataacaat ttcacacagg                                               20